US010337060B2

(12) United States Patent
Crawford et al.

(10) Patent No.: US 10,337,060 B2
(45) Date of Patent: Jul. 2, 2019

(54) METHOD FOR CHARACTERISING A DOUBLE STRANDED NUCLEIC ACID USING A NANO-PORE AND ANCHOR MOLECULES AT BOTH ENDS OF SAID NUCLEIC ACID

(71) Applicant: Oxford Nanopore Technologies Ltd., Oxford (GB)

(72) Inventors: Marion Louise Crawford, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 207 days.

(21) Appl. No.: 15/301,471

(22) PCT Filed: Mar. 31, 2015

(86) PCT No.: PCT/GB2015/050991
§ 371 (c)(1),
(2) Date: Oct. 3, 2016

(87) PCT Pub. No.: WO2015/150786
PCT Pub. Date: Oct. 8, 2015

(65) Prior Publication Data
US 2017/0204457 A1   Jul. 20, 2017

Related U.S. Application Data

(63) Continuation-in-part of application No. PCT/GB2014/052737, filed on Sep. 10, 2014.

(30) Foreign Application Priority Data

Apr. 4, 2014 (GB) .................................. 1406147.7
May 2, 2014 (GB) .................................. 1407815.8

(51) Int. Cl.
*C12Q 1/68* (2018.01)
*C07H 21/00* (2006.01)
*C12Q 1/6869* (2018.01)

(52) U.S. Cl.
CPC .... *C12Q 1/6869* (2013.01); *C12Y 306/04012* (2013.01); *C12Q 2565/631* (2013.01)

(58) Field of Classification Search
CPC ......... C12Q 1/68; C12Q 1/6869; C07H 21/00
See application file for complete search history.

(56) References Cited

U.S. PATENT DOCUMENTS

| | | | |
|---|---|---|---|
| 5,576,204 A | 11/1996 | Blanco et al. | |
| 5,712,126 A * | 1/1998 | Weissman | C12Q 1/6809 435/6.18 |
| 8,828,208 B2 | 9/2014 | Canas et al. | |
| 9,057,102 B2 | 6/2015 | Turner et al. | |
| 9,222,082 B2 | 12/2015 | Jayasinghe et al. | |
| 9,447,152 B2 | 9/2016 | Clarke et al. | |
| 9,546,400 B2 | 1/2017 | Turner et al. | |
| 9,556,480 B2 | 1/2017 | Turner et al. | |
| 9,678,056 B2 | 6/2017 | Turner et al. | |
| 9,738,929 B2 | 8/2017 | Turner et al. | |
| 2002/0192769 A1 * | 12/2002 | Park | C12Q 1/686 435/91.2 |
| 2010/0331194 A1 | 12/2010 | Turner et al. | |
| 2011/0229877 A1 | 9/2011 | Jayasinghe et al. | |
| 2012/0100530 A1 | 4/2012 | Moysey et al. | |
| 2014/0186823 A1 | 7/2014 | Clarke et al. | |
| 2014/0262784 A1 | 9/2014 | Clarke et al. | |
| 2017/0022557 A1 | 1/2017 | Clarke et al. | |
| 2017/0253910 A1 | 9/2017 | Brown et al. | |

FOREIGN PATENT DOCUMENTS

| | | |
|---|---|---|
| EP | 2682460 | 1/2014 |
| JP | 2009-519705 A1 | 5/2009 |
| WO | WO 2000/028312 | 5/2000 |
| WO | WO 2000/078668 A1 | 12/2000 |
| WO | WO 2000/079257 A1 | 12/2000 |
| WO | WO 2005/124888 | 12/2005 |
| WO | WO 2006/100484 | 9/2006 |
| WO | WO 2007/057668 A1 | 5/2007 |
| WO | WO 2008/092760 A1 | 8/2008 |
| WO | WO 2008/102120 | 8/2008 |
| WO | WO 2008/102121 | 8/2008 |
| WO | WO 2008/124107 | 10/2008 |
| WO | WO 2009/020682 A2 | 2/2009 |
| WO | WO 2009/035647 | 3/2009 |
| WO | WO 2009/077734 A2 | 6/2009 |
| WO | WO 2009/132124 A2 | 10/2009 |
| WO | WO 2010/004265 | 1/2010 |
| WO | WO 2010/004273 | 1/2010 |
| WO | WO 2010/086602 A1 | 8/2010 |
| WO | WO 2010/086603 | 8/2010 |

(Continued)

OTHER PUBLICATIONS

Feng et al., Genomics Proteomics Bioinformatics 13: 4-16 (Year: 2015).*
[No Author Listed] Lambda Exonuclease product. 2017. Last accessed at https://www.neb.com/products/m0262-lambda-exonuclease on Feb. 8, 2017.
Albrecht, Nanobiotechnology: A new look for nanopore sensing. Nat Nanotechnol. Apr. 2011;6(4):195-6. doi: 10.1038/nnano.2011.52.
Ali et al., Sequence-specific recognition of DNA oligomer using peptide nucleic acid (PNA)-modified synthetic ion channels: PNA/DNA hybridization in nanoconfined environment. ACS Nano. Dec. 28, 2010;4(12):7267-74. doi: 10.1021/nn102119q. Epub Nov. 17, 2010.

(Continued)

*Primary Examiner* — Ethan C Whisenant
(74) *Attorney, Agent, or Firm* — Wolf, Greenfield & Sacks, P.C.

(57) ABSTRACT

The invention relates to a method for method of characterizing, such as sequencing, a target double stranded polynucleotide. The polynucleotide is coupled to a membrane using at least two adaptors with different strengths of coupling to the membrane.

17 Claims, 18 Drawing Sheets

Specification includes a Sequence Listing.

(56) References Cited

FOREIGN PATENT DOCUMENTS

| WO | WO 2010/086622 A2 | 8/2010 |
|---|---|---|
| WO | WO 2010/122293 | 10/2010 |
| WO | WO 2011/067559 | 6/2011 |
| WO | WO 2012/033524 A2 | 3/2012 |
| WO | WO 2012/107778 A2 | 8/2012 |
| WO | WO 2012/164270 | 12/2012 |
| WO | WO 2013/014451 A1 | 1/2013 |
| WO | WO 2013/041878 | 3/2013 |
| WO | WO 2013/057495 | 4/2013 |
| WO | WO 2013/098561 | 7/2013 |
| WO | WO 2013/098562 | 7/2013 |
| WO | WO 2013/153359 | 10/2013 |
| WO | WO 2014/013259 | 1/2014 |
| WO | WO 2014/013260 | 1/2014 |
| WO | WO 2014/013262 | 1/2014 |
| WO | WO 2014/064443 | 5/2014 |
| WO | WO 2014/064444 | 5/2014 |
| WO | WO 2014/135838 | 9/2014 |
| WO | WO 2015/022544 | 2/2015 |
| WO | WO 2015/055981 | 4/2015 |
| WO | WO 2015/110777 | 7/2015 |
| WO | WO 2015/124935 | 8/2015 |
| WO | WO 2015/150786 A1 | 10/2015 |
| WO | WO 2015/150787 | 10/2015 |

OTHER PUBLICATIONS

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Andersson et al., Detection of single ion channel activity on a chip using tethered bilayer membranes. Langmuir. Mar. 13, 2007;23(6):2924-7. Epub Feb. 8, 2007.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Bayley et al., Stochastic sensors inspired by biology. Nature. Sep. 13, 2001;413(6852):226-30.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi:10.1038/nbt.1495.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Castellana et al., Solid supported lipid bilayers: From biophysical studies to sensor design. Surface Science Reports, vol. 61 :429-444 (2006).

Chandler et al., Membrane surface dynamics of DNA-threaded nanopores revealed by simultaneous single-molecule optical and ensemble electrical recording. Langmuir. Feb. 3, 2004;20(3):898-905.

Cheley et al., Stochastic sensing of nanomolar inositol 1,4,5-trisphosphate with an engineered pore. Chem Biol. Jul. 2002;9(7):829-38.

Chen et al., Electrical nanogap devices for biosensing. Materials today, vol. 13(11 ):28-41 (2010).

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Colas et al., Microscopical investigations of nisin-loaded nanoliposomes prepared by Mozafari method and their bacterial targeting. Micron. 2007;38(8):841-7. Epub Jul. 3, 2007.

Dekker, Solid-state nanopores. Nat Nanotechnol. Apr. 2007;2(4):209-15. doi:10.1038/nnano.2007.27. Epub Mar. 4, 2007.

Devereux et al., A comprehensive set of sequence analysis programs for the VAX. Nucleic Acids Res. Jan. 11, 1984;12(1 Pt 1):387-95.

Eliseev et al., Molecular Recognition of Nucleotides, Nucleosides, and Sugars by Aminocyclodextrins. J. Am. Chem. Soc., vol. 116:6081-6088 (1994).

Garaj et al., Graphene as a subnanometre trans-electrode membrane. Nature. Sep. 9, 2010;467(7312):190-3. doi:10.1038/nature09379. Epub Aug. 18, 2010.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Grant et al., A facile method for attaching nitroxide spin labels at the 5' terminus of nucleic acids. Nucleic Acids Res. 2007;35(10):e77. Epub May 21, 2007.

Gu et al., Interaction of the noncovalent molecular adapter, beta-cyclodextrin, with the staphylococcal alpha-hemolysin pore. Biophys J. Oct. 2000;79(4):1967-75.

Hoffmann et al., Molecular recognition in biotin-treptavidin systems and analogues at the air-water interface. Thin Solid Films. 1992;210/211:780-783.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Howorka et al., Nanopore analytics: sensing of single molecules. Chem Soc Rev. Aug. 2009;38(8):2360-84. doi: 10.1039/b813796j. Epub Jun. 15, 2009.

Ivanov et al., DNA tunneling detector embedded in a nanopore. Nano Lett. Jan. 12, 2011;11(1):279-85. doi: 10.1021/n1103873a. Epub Dec. 6, 2010.

Kang et al., Stochastic detection of enantiomers. J Am Chem Soc. Aug. 23, 2006;128(33):10684-5.

Kasianowicz et al., Characterization of individual polynucleotide molecules using a membrane channel. Proc Natl Acad Sci U S A. Nov. 26, 1996;93(24):13770-3.

Keyser, Controlling molecular transport through nanopores. J R Soc Interface. Oct. 7, 2011;8(63):1369-78. doi: 10.1098/rsif.2011.0222.

Kim et al., Elucidation of bacterial genome complexity using next-generation sequencing. Biotech Bioprocess Eng. Oct. 2012;17(50:887-899.

Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.

Langecker et al., Synthetic lipid membrane channels formed by designed DNA nanostructures. Science. Nov. 16, 2012;338(6109):932-6. doi: 10.1126/science.1225624.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

(56) References Cited

OTHER PUBLICATIONS

Maddox et al., Elevated serum levels in human pregnancy of a molecule immunochemically similar to eosinophil granule major basic protein. J Exp Med. Oct. 1, 1983;158(4):1211-26.

Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.

Merchant et al., DNA translocation through graphene nanopores. Nano Lett. Aug. 11, 2010;10(8):2915-21. doi: 10.1021/nl101046t.

Montal et al., Formation of bimolecular membranes from lipid monolayers and a study of their electrical properties. Proc Natl Acad Sci U S A. Dec. 1972;69(12):3561-6.

Movileanu et al., Interactions of peptides with a protein pore. Biophys J. Aug. 2005;89(2):1030-45. Epub May 27, 2005.

Nikolov et al., Behavior of giant vesicles with anchored DNA molecules. Biophys J. Jun. 15, 2007;92(12):4356-68. Epub Mar. 23, 2007.

Ohvo et al., Cyclodextrin-mediated removal of sterols from monolayers:effects of sterol structure and phospholipids on desorption rate. Biochemistry. Jun. 18, 1996;35(24):8018-24.

Pfeiffer et al., Bivalent cholesterol-based coupling of oligonucletides to lipid membrane assemblies. J Am Chem Soc. Aug. 25, 2004;126(33):10224-5.

Schmitz et al., Nonradioactive labeling of oligonucleotides in vitro with the hapten digoxigenin by tailing with terminal transferase. Anal Biochem. Jan. 1991;192(1):222-31.

Schneider et al., DNA translocation through graphene nanopores. Nano Lett. Aug. 11, 2010;10(8):3163-7. doi: 10.1021/nl102069z.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.

United States District Court for the District of Delaware Order. *Pacific Biosciences of California, Inc.* v. *Oxford Nanopore Technolgoies, Inc.* Civil Action No. 17-275-RGA. Nov. 9, 2017.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

Wang et al., Nanopore-based detection of circulating microRNAs in lung cancer patients. Nat Nanotechnol. Sep. 4, 2011;6(10):668-74. doi: 10.1038/nnano.2011.147.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wilson et al., Electronic control of DNA polymerase binding and unbinding to single DNA molecules. ACS Nano. Apr. 28, 2009;3(4):995-1003. doi: 10.1021/nn9000897.

Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.

Yoshina-Ishii et al., Arrays of mobile tethered vesicles on supported lipid bilayers. J Am Chem Soc. Apr. 2, 2003;125(13):3696-7.

Yusko et al., Controlling protein translocation through nanopores with bio-inspired fluid walls. Nat Nanotechnol. Apr. 2011;6(4):253-60. doi: 10.1038/nnano.2011.12. Epub Feb. 20, 2011.

Zidovetzki et al., Use of cyclodextrins to manipulate plasma membrane cholesterol content: evidence, misconceptions and control strategies. Biochim Biophys Acta. Jun. 2007;1768(6):1311-24.

\* cited by examiner (A)

(B)

SEQUENCE LISTING

```
<160> NUMBER OF SEQ ID NOS: 54

<210> SEQ ID NO 1
<211> LENGTH: 558
<212> TYPE: DNA
<213> ORGANISM: Artificial Sequence
<220> FEATURE:
<223> OTHER INFORMATION: Mycobacterium smegmatis porin A mutant
      (D90N/D91N/D93N/D118R/D134R/E193K)

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                    558

<210> SEQ ID NO 2
<211> LENGTH: 184
<212> TYPE: PRT
<213> ORGANISM: Artificial Sequence
<220> FEATURE:
<223> OTHER INFORMATION: Mycobacterium smegmatis porin A mutant
      (D90N/D91N/D93N/D118R/D134R/E139K)

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95
```

-continued

```
Pro Pro Phe Gly Leu Asn Ser Val Ile Thr Pro Asn Leu Phe Pro Gly
        100                 105                 110

Val Ser Ile Ser Ala Arg Leu Gly Asn Gly Pro Gly Ile Gln Glu Val
    115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
        180
```

<210> SEQ ID NO 3
<211> LENGTH: 885
<212> TYPE: DNA
<213> ORGANISM: Artificial Sequence
<220> FEATURE:
<223> OTHER INFORMATION: alpha-hemolysin mutant (E111N/K147N)

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaagtatttt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata tgaagtagc tcaaatatct    300
gattactatc caagaaattc gattgataca aaaaactata tgagtacttt aacttatgga    360
ttcaacggta atgttactgg tgatgataca ggaaaaattg gcggccttat tggtgcaaat    420
gtttcgattg tcatacact gactatgtt caacctgatt tcaaaacaat tttagagagc    480
ccaactgata aaaagtagg ctggaaagtg atatttaaca atatggtgaa tcaaaattgg    540
ggaccatacg atcgagattc ttggaacccg tatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata atggacaga tcgttcttca    840
gaaagatata aaatcgattg ggaaaaagaa gaaatgacaa attaa                    885
```

<210> SEQ ID NO 4
<211> LENGTH: 293
<212> TYPE: PRT
<213> ORGANISM: Artificial Sequence
<220> FEATURE:
<223> OTHER INFORMATION: alpha-hemolysin mutant (E111N/K147N)

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
```

```
        50                  55                  60
Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Asn Tyr
                100                 105                 110

Met Ser Thr Leu Thr Tyr Gly Phe Asn Gly Asn Val Thr Gly Asp Asp
                115                 120                 125

Thr Gly Lys Ile Gly Gly Leu Ile Gly Ala Asn Val Ser Ile Gly His
                130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
                275                 280                 285

Glu Glu Met Thr Asn
            290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
 1               5                  10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
                35                  40                  45

Ile Val Ala Gly Pro Gly Ala Asp Glu Phe Glu Gly Thr Leu Glu Leu
 50                  55                  60

Gly Tyr Gln Ile Gly Phe Pro Trp Ser Leu Gly Val Gly Ile Asn Phe
 65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
                100                 105                 110

Val Ser Ile Ser Ala Asp Leu Gly Asn Gly Pro Gly Ile Gln Glu Val
                115                 120                 125
```

```
Ala Thr Phe Ser Val Asp Val Ser Gly Pro Ala Gly Val Ala Val
        130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80
```

```
Tyr Thr Thr Pro Asn Ile Leu Ile Asp Gly Asp Ile Thr Gln Pro
             85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
            115                 120                 125

Thr Phe Ser Val Asp Val Lys Gly Ala Lys Gly Ala Val Ala Val Ser
            130                 135                 140

Asn Ala His Gly Thr Val Thr Gly Ala Ala Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 1830
<212> TYPE: DNA
<213> ORGANISM: Bacillus subtilis phage phi29

<400> SEQUENCE: 8
atgaaacaca tgccgcgtaa aatgtatagc tgcgcgtttg aaaccacgac caaagtggaa      60
gattgtcgcg tttgggccta tggctacatg aacatcgaag atcattctga atacaaaatc    120
ggtaacagtc tggatgaatt tatggcatgg gtgctgaaag ttcaggcgga tctgtacttc    180
cacaacctga aatttgatgg cgcattcatt atcaactggc tggaacgtaa tggctttaaa    240
tggagcgcgg atggtctgcc gaacacgtat aataccatta tctctcgtat gggccagtgg    300
tatatgattg atatctgcct gggctacaaa ggtaaacgca aaattcatac cgtgatctat    360
gatagcctga aaaactgcc gtttccggtg aagaaaattg cgaaagattt caaactgacg    420
gttctgaaag cgatattga ttatcacaaa gaacgtccgg ttggttacaa aatcaccccg    480
gaagaatacg catacatcaa aaacgatatc cagatcatcg cagaagcgct gctgattcag    540
tttaaacagg gcctggatcg catgaccgcg ggcagtgata gcctgaaagg tttcaaagat    600
atcatcacga ccaaaaaatt caaaaaagtg ttcccgacgc tgagcctggg tctggataaa    660
gaagttcgtt atgcctaccg cggcggtttt acctggctga cgatcgtttt caaagaaaaa    720
gaaattggcg agggtatggt gtttgatgtt aatagtctgt atccggcaca gatgtacagc    780
cgcctgctgc gtatggcga accgatcgtg ttcgaggta aatatgtttg ggatgaagat    840
tacccgctgc atattcagca catccgttgt gaatttgaac tgaaagaagg ctatattccg    900
accattcaga tcaaacgtag tcgcttctat aagggtaacg aatacctgaa aagctctggc    960
ggtgaaatcg cggatctgtg gctgagtaac gtggatctgg aactgatgaa agaacactac   1020
gatctgtaca cgttgaata catcagcggc ctgaaattta agccacgac cggtctgttc   1080 aaagatttca tcgataaatg gacctacatc aaaacgacct tgaaggcgc gattaaacag   1140 ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaaat acctgcgcca gaaaacctac   1500
```

-continued

```
atccaggata tctacatgaa agaagtggat ggcaaactgg ttgaaggttc tccggatgat      1560
tacaccgata tcaaattcag tgtgaaatgc gccggcatga cggataaaat caaaaaagaa      1620
gtgaccttcg aaaacttcaa agttggtttc agccgcaaaa tgaaaccgaa accggtgcag      1680
gttccgggcg gtgtggttct ggtggatgat acgtttacca ttaaatctgg cggtagtgcg      1740
tggagccatc cgcagttcga aaaggcggt ggctctggtg gcggttctgg cggtagtgcc      1800
tggagccacc cgcagtttga aaataataa                                       1830
```

<210> SEQ ID NO 9
<211> LENGTH: 608
<212> TYPE: PRT
<213> ORGANISM: Bacillus subtilis phage phi29

<400> SEQUENCE: 9

```
Met Lys His Met Pro Arg Lys Met Tyr Ser Cys Ala Phe Glu Thr Thr
 1               5                  10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
           100                 105                 110

Arg Lys Ile His Thr Val Ile Tyr Asp Ser Leu Lys Lys Leu Pro Phe
       115                 120                 125

Pro Val Lys Lys Ile Ala Lys Asp Phe Lys Leu Thr Val Leu Lys Gly
   130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320
```

Gly Glu Ile Ala Asp Leu Trp Leu Ser Asn Val Asp Leu Glu Leu Met
              325                 330                 335

Lys Glu His Tyr Asp Leu Tyr Asn Val Glu Tyr Ile Ser Gly Leu Lys
              340                 345                 350

Phe Lys Ala Thr Thr Gly Leu Phe Lys Asp Phe Ile Asp Lys Trp Thr
              355                 360                 365

Tyr Ile Lys Thr Thr Ser Glu Gly Ala Ile Lys Gln Leu Ala Lys Leu
              370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
              405                 410                 415

Gly Glu Glu Thr Lys Asp Pro Val Tyr Thr Pro Met Gly Val Phe
              420                 425                 430

Ile Thr Ala Trp Ala Arg Tyr Thr Thr Ile Thr Ala Ala Gln Ala Cys
              435                 440                 445

Tyr Asp Arg Ile Ile Tyr Cys Asp Thr Asp Ser Ile His Leu Thr Gly
              450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
              485                 490                 495

Gln Lys Thr Tyr Ile Gln Asp Ile Tyr Met Lys Glu Val Asp Gly Lys
              500                 505                 510

Leu Val Glu Gly Ser Pro Asp Asp Tyr Thr Asp Ile Lys Phe Ser Val
              515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
              565                 570                 575

Gly Gly Ser Ala Trp Ser His Pro Gln Phe Glu Lys Gly Gly Gly Ser
              580                 585                 590

Gly Gly Gly Ser Gly Gly Ser Ala Trp Ser His Pro Gln Phe Glu Lys
              595                 600                 605

<210> SEQ ID NO 10
<211> LENGTH: 1390
<212> TYPE: DNA
<213> ORGANISM: Escherichia coli

<400> SEQUENCE: 10
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccggga agtgtttat tgcaaaccgg ccgatgatta tctgccgcag      180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac ctgcattctg      300
ggctataaca atgtgcgctt cgatgatgaa gttacccgta atatctttta cgtaactttt     360
tatgatccgt atgcgtggag ctggcagcat gataacagcc gttgggatct gctggatgtg     420
atgcgcgcgt gctatgcgct cgcccccgaa ggcattaatt ggccggaaaa cgatgatggc     480

```
ctgccgagct tcgtctgga acatctgacc aaagccaacg gcattgaaca tagcaatgcc    540
catgatgcga tggccgatgt ttatgcgacc attgcgatgg cgaaactggt taaaacccgt    600
cagccgcgcc tgtttgatta tctgtttacc caccgtaaca acacaaaact gatggcgctg    660
attgatgttc cgcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta caaatgccc ggtgctggcc caggcgaaca ccctgcgccc ggaagatgcg    960
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca ttttccgggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taagaaaaaa    1380
gtggcgctgc                                                           1390
```

<210> SEQ ID NO 11
<211> LENGTH: 485
<212> TYPE: PRT
<213> ORGANISM: Escherichia coli

<400> SEQUENCE: 11

```
Met Met Asn Asp Gly Lys Gln Gln Ser Thr Phe Leu Phe His Asp Tyr
 1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205
```

-continued

```
Phe Thr His Arg Asn Lys His Lys Leu Met Ala Leu Ile Asp Val Pro
    210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
        275                 280                 285
Asp Leu Gly Asp Asn Ala Ala Val Pro Val Lys Leu Val His Ile Asn
    290                 295                 300
Lys Cys Pro Val Leu Ala Gln Ala Asn Thr Leu Arg Pro Glu Asp Ala
305                 310                 315                 320
Asp Arg Leu Gly Ile Asn Arg Gln His Cys Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
        355                 360                 365
Asn Gly Phe Phe Ser Asp Ala Asp Arg Ala Ala Met Lys Ile Val Leu
    370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gln Gly Tyr Ala Asp Glu Leu Gln
        435                 440                 445
Met Leu Val Gln Gln Tyr Ala Asp Asp Lys Glu Lys Val Ala Leu Leu
    450                 455                 460
Lys Ala Leu Trp Gln Tyr Ala Glu Glu Ile Val Ser Gly Ser Gly His
465                 470                 475                 480
His His His His His
            485

<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc      60
atcgtcgaaa agcaccaacc ggatgtgatt ggcctgcagg agacaaaagt tcatgacgat     120
atgtttccgc tcgaagaggt ggcgaagctc ggctacaacg tgttttatca cgggcagaaa     180
ggccattatg gcgtggcgct gctgaccaaa gagacgccga ttgccgtgcg tcgcggcttt     240
cccggtgacg acgaagaggc gcagcggcgg attattatgg cggaaatccc ctcactgctg     300
ggtaatgtca ccgtgatcaa cggttacttc ccgcagggtg aaagccgcga ccatccgata     360
aaattcccgg caaaagcgca gttttatcag aatctgcaaa actacctgga accgaactc     420 aaacgtgata tccggtact gattatgggc gatatgaata tcagccctac agatctggat     480
atcggcattg gcgaagaaaa ccgtaagcgc tggctgcgta ccggtaaatg ctctttcctg     540
```

```
ccggaagagc gcgaatggat ggacaggctg atgagctggg ggttggtcga taccttccgc    600
catgcgaatc cgcaaacagc agatcgtttc tcatggtttg attaccgctc aaaaggtttt    660
gacgataacc gtggtctgcg catcgacctg ctgctcgcca gccaaccgct ggcagaatgt    720
tgcgtagaaa ccggcatcga ctatgaaatc cgcagcatgg aaaaaccgtc cgatcacgcc    780
cccgtctggg cgaccttccg ccgc                                           804
```

```
<210> SEQ ID NO 13
<211> LENGTH: 268
<212> TYPE: PRT
<213> ORGANISM: Escherichia coli

<400> SEQUENCE: 13
```

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265

```
<210> SEQ ID NO 14
<211> LENGTH: 1275
<212> TYPE: DNA
<213> ORGANISM: Thermus thermophilus

<400> SEQUENCE: 14
atgtttcgtc gtaaagaaga tctggatccg ccgctggcac tgctgccgct gaaaggcctg    60
```

-continued

```
cgcgaagccg ccgcactgct ggaagaagcg ctgcgtcaag gtaaacgcat tcgtgttcac      120
ggcgactatg atgcggatgg cctgaccggc accgcgatcc tggttcgtgg tctggccgcc      180
ctgggtgcgg atgttcatcc gtttatcccg caccgcctgg aagaaggcta tggtgtcctg      240
atggaacgcg tcccggaaca tctggaagcc tcggacctgt ttctgaccgt tgactgcggc      300
attaccaacc atgcggaact gcgcgaactg ctggaaaatg gcgtggaagt cattgttacc      360
gatcatcata cgccgggcaa aacgccgccc cgggtctgg tcgtgcatcc ggcgctgacg       420
ccggatctga agaaaaaacc gaccggcgca ggcgtggcgt ttctgctgct gtgggcactg      480
catgaacgcc tgggcctgcc gccgccgctg aatacgcgg acctggcagc cgttggcacc       540
attgccgacg ttgccccgct gtggggttgg aatcgtgcac tggtgaaaga aggtctggca      600
cgcatcccgg cttcatcttg gtgggcctg cgtctgctgg ctgaagccgt gggctatacc       660
ggcaaagcgg tcgaagtcgc tttccgcatc gcgccgcgca tcaatgcggc ttcccgcctg      720
ggcgaagcgg aaaaagccct gcgcctgctg ctgacggatg atgcggcaga agctcaggcg      780
ctggtcggcg aactgcaccg tctgaacgcc cgtcgtcaga ccctggaaga agcgatgctg      840
cgcaaactgc tgccgcaggc cgacccggaa gcgaaagcca tcgttctgct ggacccggaa      900
ggccatccgg tgttatggg tattgtggcc tctcgcatcc tggaagcgac cctgcgcccg       960
gtctttctgg tgcccagggg caaaggcacc gtgcgttcgc tggctccgat tccgccgtc      1020
gaagcactgc gcagcgcgga agatctgctg ctgcgttatg gtggtcataa agaagcggcg     1080
ggtttcgcaa tggatgaagc gctgtttccg gcgttcaaag cacgcgttga agcgtatgcc     1140
gcacgttttcc cggatccggt tcgtgaagtg gcactgctgg atctgctgcc ggaaccgggc    1200
ctgctgccgc aggtgttccg tgaactggca ctgctggaac cgtatggtga aggtaacccg     1260
gaaccgctgt tcctg                                                      1275
```

<210> SEQ ID NO 15
<211> LENGTH: 425
<212> TYPE: PRT
<213> ORGANISM: Thermus thermophilus

<400> SEQUENCE: 15

```
Met Phe Arg Arg Lys Glu Asp Leu Asp Pro Pro Leu Ala Leu Leu Pro
1               5                   10                  15

Leu Lys Gly Leu Arg Glu Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
```

```
                145                 150                 155                 160
            His Glu Arg Leu Gly Leu Pro Pro Leu Glu Tyr Ala Asp Leu Ala
                            165                 170                 175

Ala Val Gly Thr Ile Ala Asp Val Ala Pro Leu Trp Gly Trp Asn Arg
                        180                 185                 190

Ala Leu Val Lys Glu Gly Leu Ala Arg Ile Pro Ala Ser Ser Trp Val
                        195                 200                 205

Gly Leu Arg Leu Leu Ala Glu Ala Val Gly Tyr Thr Gly Lys Ala Val
                    210                 215                 220

Glu Val Ala Phe Arg Ile Ala Pro Arg Ile Asn Ala Ala Ser Arg Leu
            225                 230                 235                 240

Gly Glu Ala Glu Lys Ala Leu Arg Leu Leu Thr Asp Asp Ala Ala
                            245                 250                 255

Glu Ala Gln Ala Leu Val Gly Glu Leu His Arg Leu Asn Ala Arg Arg
                        260                 265                 270

Gln Thr Leu Glu Glu Ala Met Leu Arg Lys Leu Leu Pro Gln Ala Asp
                        275                 280                 285

Pro Glu Ala Lys Ala Ile Val Leu Leu Asp Pro Glu Gly His Pro Gly
                    290                 295                 300

Val Met Gly Ile Val Ala Ser Arg Ile Leu Glu Ala Thr Leu Arg Pro
            305                 310                 315                 320

Val Phe Leu Val Ala Gln Gly Lys Gly Thr Val Arg Ser Leu Ala Pro
                            325                 330                 335

Ile Ser Ala Val Glu Ala Leu Arg Ser Ala Glu Asp Leu Leu Leu Arg
                        340                 345                 350

Tyr Gly Gly His Lys Glu Ala Ala Gly Phe Ala Met Asp Glu Ala Leu
                        355                 360                 365

Phe Pro Ala Phe Lys Ala Arg Val Glu Ala Tyr Ala Ala Arg Phe Pro
                    370                 375                 380

Asp Pro Val Arg Glu Val Ala Leu Leu Asp Leu Leu Pro Glu Pro Gly
            385                 390                 395                 400

Leu Leu Pro Gln Val Phe Arg Glu Leu Ala Leu Leu Glu Pro Tyr Gly
                            405                 410                 415

Glu Gly Asn Pro Glu Pro Leu Phe Leu
                        420                 425

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc      60
gggatcgatg tgagagctgt cgaacagggg gatgatgcgt ggcacaaatt acggctcggc     120
gtcatcaccg cttcagaagt tcacaacgtg atagcaaaac cccgctccgg aaagaagtgg     180
cctgacatga aaatgtccta cttccacacc ctgcttgctg aggtttgcac cggtgtggct     240
ccggaagtta acgctaaagc actggcctgg ggaaaacagt acgagaacga cgccagaacc     300
ctgtttgaat tcacttccgg cgtgaatgtt actgaatccc cgatcatcta tcgcgacgaa     360
agtatgcgta ccgcctgctc tcccgatggt ttatgcagtg acggcaacgg ccttgaactg     420
aaatgcccgt ttacctcccg ggatttcatg aagttccggc tcggtggttt cgaggccata     480
aagtcagctt acatggccca ggtgcagtac agcatgtggg tgacgcgaaa aaatgcctgg     540
```

```
tactttgcca actatgaccc gcgtatgaag cgtgaaggcc tgcattatgt cgtgattgag      600
cgggatgaaa agtacatggc gagttttgac gagatcgtgc cggagttcat cgaaaaaatg      660
gacgaggcac tggctgaaat tggttttgta tttggggagc aatggcgatc tggctctggt      720
tccggcagcg gttccgga                                                    738
```

<210> SEQ ID NO 17
<211> LENGTH: 226
<212> TYPE: PRT
<213> ORGANISM: Bacteriophage lambda

<400> SEQUENCE: 17

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

<210> SEQ ID NO 18
<211> LENGTH: 760
<212> TYPE: PRT
<213> ORGANISM: Methanococcoides burtonii

<400> SEQUENCE: 18

```
Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
                20                  25                  30

Glu Met Gly Leu Leu Glu Lys Lys Asn Leu Leu Ala Ala Ile Pro Thr
            35                  40                  45

Ala Ser Gly Lys Thr Leu Leu Ala Glu Leu Ala Met Ile Lys Ala Ile
```

```
                50                  55                  60
Arg Glu Gly Gly Lys Ala Leu Tyr Ile Val Pro Leu Arg Ala Leu Ala
 65                  70                  75                  80

Ser Glu Lys Phe Glu Arg Phe Lys Glu Leu Ala Pro Phe Gly Ile Lys
                     85                  90                  95

Val Gly Ile Ser Thr Gly Asp Leu Asp Ser Arg Ala Asp Trp Leu Gly
                100                 105                 110

Val Asn Asp Ile Ile Val Ala Thr Ser Glu Lys Thr Asp Ser Leu Leu
                115                 120                 125

Arg Asn Gly Thr Ser Trp Met Asp Glu Ile Thr Thr Val Val Asp
130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
                180                 185                 190

Ala Ala Leu Val Leu Ser Glu Trp Arg Pro Thr Asp Leu His Glu Gly
                195                 200                 205

Val Leu Phe Gly Asp Ala Ile Asn Phe Pro Gly Ser Gln Lys Lys Ile
                210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
                260                 265                 270

Asn Asp Ile Met Ile Lys Leu Ala Gly Ile Ala Glu Glu Val Glu Ser
                275                 280                 285

Thr Gly Glu Thr Asp Thr Ala Ile Val Leu Ala Asn Cys Ile Arg Lys
                290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
                340                 345                 350

Arg Ser Tyr Arg Arg Phe Asp Ser Asn Phe Gly Met Gln Pro Ile Pro
                355                 360                 365

Val Leu Glu Tyr Lys Gln Met Ala Gly Arg Ala Gly Arg Pro His Leu
                370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
                420                 425                 430

Ile Val Asn Gly Phe Ala Ser Thr Arg Gln Glu Leu Phe Asp Phe Phe
                435                 440                 445

Gly Ala Thr Phe Phe Ala Tyr Gln Gln Asp Lys Trp Met Leu Glu Glu
                450                 455                 460

Val Ile Asn Asp Cys Leu Glu Phe Leu Ile Asp Lys Ala Met Val Ser
465                 470                 475                 480
```

```
Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
            515                 520                 525

Asn Met Gly Ser Leu Glu Asp Asp Lys Gly Asp Asp Ile Thr Val Thr
            530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
                580                 585                 590

Asp Tyr Glu Trp Phe Met Gly Glu Val Lys Thr Ala Met Leu Leu Glu
                595                 600                 605

Glu Trp Val Thr Glu Val Ser Ala Glu Asp Ile Thr Arg His Phe Asn
            610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
                660                 665                 670

Asp Leu Met Glu Leu Val Gly Ile Arg Gly Val Gly Arg Val Arg Ala
            675                 680                 685

Arg Lys Leu Tyr Asn Ala Gly Phe Val Ser Val Ala Lys Leu Lys Gly
            690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
                740                 745                 750

Gln Lys Thr Phe Asn Asp Phe Gln
            755                 760

<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
            35                  40                  45

Ala Ser Gly Lys Thr Leu Ile Ala Ile Ala Met Ile Ser His Leu
            50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
```

```
                85                  90                  95
Gly Arg Pro Val Arg Val Gly Val Ser Thr Gly Asp Phe Glu Lys Ala
            100                 105                 110
Gly Arg Ser Leu Gly Asn Asn Asp Ile Leu Val Leu Thr Asn Glu Arg
            115                 120                 125
Met Asp Ser Leu Ile Arg Arg Pro Asp Trp Met Asp Glu Val Gly
    130                 135                 140
Leu Val Ile Ala Asp Glu Ile His Leu Ile Gly Asp Arg Ser Arg Gly
145                 150                 155                 160
Pro Thr Leu Glu Met Val Leu Thr Lys Leu Arg Gly Leu Arg Ser Ser
                165                 170                 175
Pro Gln Val Val Ala Leu Ser Ala Thr Ile Ser Asn Ala Asp Glu Ile
            180                 185                 190
Ala Gly Trp Leu Asp Cys Thr Leu Val His Ser Thr Trp Arg Pro Val
            195                 200                 205
Pro Leu Ser Glu Gly Val Tyr Gln Asp Gly Glu Val Ala Met Gly Asp
    210                 215                 220
Gly Ser Arg His Glu Val Ala Ala Thr Gly Gly Pro Ala Val Asp
225                 230                 235                 240
Leu Ala Ala Glu Ser Val Ala Glu Gly Gly Gln Ser Leu Ile Phe Ala
                245                 250                 255
Asp Thr Arg Ala Arg Ser Ala Ser Leu Ala Ala Lys Ala Ser Ala Val
            260                 265                 270
Ile Pro Glu Ala Lys Gly Ala Asp Ala Ala Lys Leu Ala Ala Ala
            275                 280                 285
Lys Lys Ile Ile Ser Ser Gly Gly Glu Thr Lys Leu Ala Lys Thr Leu
    290                 295                 300
Ala Glu Leu Val Glu Lys Gly Ala Ala Phe His His Ala Gly Leu Asn
305                 310                 315                 320
Gln Asp Cys Arg Ser Val Val Glu Glu Phe Arg Ser Gly Arg Ile
                325                 330                 335
Arg Leu Leu Ala Ser Thr Pro Thr Leu Ala Ala Gly Val Asn Leu Pro
            340                 345                 350
Ala Arg Arg Val Val Ile Ser Ser Val Met Arg Tyr Asn Ser Ser Ser
            355                 360                 365
Gly Met Ser Glu Pro Ile Ser Ile Leu Glu Tyr Lys Gln Leu Cys Gly
    370                 375                 380
Arg Ala Gly Arg Pro Gln Tyr Asp Lys Ser Gly Glu Ala Ile Val Val
385                 390                 395                 400
Gly Gly Val Asn Ala Asp Glu Ile Phe Asp Arg Tyr Ile Gly Gly Glu
                405                 410                 415
Pro Glu Pro Ile Arg Ser Ala Met Val Asp Asp Arg Ala Leu Arg Ile
            420                 425                 430
His Val Leu Ser Leu Val Thr Thr Ser Pro Gly Ile Lys Glu Asp Asp
            435                 440                 445
Val Thr Glu Phe Phe Leu Gly Thr Leu Gly Gly Gln Gln Ser Gly Glu
    450                 455                 460
Ser Thr Val Lys Phe Ser Val Ala Val Ala Leu Arg Phe Leu Gln Glu
465                 470                 475                 480
Glu Gly Met Leu Gly Arg Arg Gly Gly Arg Leu Ala Ala Thr Lys Met
                485                 490                 495
Gly Arg Leu Val Ser Arg Leu Tyr Met Asp Pro Met Thr Ala Val Thr
            500                 505                 510
```

-continued

Leu Arg Asp Ala Val Gly Glu Ala Ser Pro Gly Arg Met His Thr Leu
         515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Ser Gly Asp Val His Arg Met Val
        595                 600                 605

Glu Ser Ser Gly Trp Leu Leu Arg Cys Ile Trp Glu Ile Ser Lys His
610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
                660                 665                 670

Gly Pro Gly Asp Leu Ala Ala Val Pro Val Glu Arg Leu Ser Arg Val
            675                 680                 685

Glu Gly Ile Gly Ala Thr Leu Ala Asn Asn Ile Lys Ser Gln Leu Arg
690                 695                 700

Lys Gly Gly
705

<210> SEQ ID NO 20
<211> LENGTH: 720
<212> TYPE: PRT
<213> ORGANISM: Thermococcus gammatolerans

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser

```
                165                 170                 175
Ala Thr Val Gly Asn Ala Glu Glu Leu Ala Glu Trp Leu Asp Ala Ser
                180                 185                 190

Leu Val Val Ser Asp Trp Arg Pro Val Gln Leu Arg Arg Gly Val Phe
                195                 200                 205

His Leu Gly Thr Leu Ile Trp Glu Asp Gly Lys Val Glu Ser Tyr Pro
            210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
                260                 265                 270

Ala Leu Glu Ser Leu Ala Ser Gln Leu Glu Asp Asn Pro Thr Ser Glu
                275                 280                 285

Lys Leu Lys Arg Ala Leu Arg Gly Gly Val Ala Phe His His Ala Gly
290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Arg Asp Thr Lys Arg Tyr Ala Gly
                340                 345                 350

Phe Gly Trp Thr Asp Ile Pro Val Leu Glu Ile Gln Gln Met Met Gly
                355                 360                 365

Arg Ala Gly Arg Pro Arg Tyr Asp Lys Tyr Gly Glu Ala Ile Ile Val
370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
                420                 425                 430

Glu Leu Val Arg Phe Leu Glu Arg Thr Phe Tyr Ala His Gln Arg Lys
                435                 440                 445

Asp Leu Ser Ser Leu Glu Tyr Lys Ala Lys Glu Val Val Tyr Phe Leu
                450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
                500                 505                 510

Pro Phe Gly Ile Phe Gln Leu Ile Ala Ser Thr Pro Asp Met Ala Thr
                515                 520                 525

Leu Thr Ala Arg Arg Glu Met Glu Asp Tyr Leu Asp Leu Ala Tyr
                530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
                580                 585                 590
```

```
Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
        610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
                660                 665                 670

Ala Asn Ala Lys Pro Ala Glu Leu Leu Ala Val Glu Gly Ile Gly Ala
                675                 680                 685

Lys Ile Leu Asp Gly Ile Tyr Arg His Leu Gly Ile Glu Lys Arg Val
        690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
                20                  25                  30

Glu Lys Gly Leu Leu Glu Gly Lys Asn Leu Leu Ile Ser Ile Pro Thr
            35                  40                  45

Ala Ser Gly Lys Thr Leu Leu Ala Glu Met Ala Met Trp Ser Arg Ile
        50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
                100                 105                 110

Asp Ile Ile Val Ala Thr Ser Glu Lys Thr Asp Ser Leu Leu Arg Asn
            115                 120                 125

Arg Thr Pro Trp Leu Ser Gln Ile Thr Cys Ile Val Leu Asp Glu Val
        130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Gly Leu Ser
                165                 170                 175

Ala Thr Ile Gly Asn Pro Ala Gln Leu Ala Glu Trp Leu Asp Ala Thr
                180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
```

```
                245                 250                 255
Phe Ala Lys Lys Ala Gly Ala Leu Lys Ala Gly Ser Pro Asp Ser
            260                 265                 270
Lys Ala Leu Ala Gln Glu Leu Arg Arg Leu Arg Asp Arg Asp Glu Gly
            275                 280                 285
Asn Val Leu Ala Asp Cys Val Glu Arg Gly Ala Ala Phe His His Ala
            290                 295                 300
Gly Leu Ile Arg Gln Glu Arg Thr Ile Ile Glu Glu Gly Phe Arg Asn
305                 310                 315                 320
Gly Tyr Ile Glu Val Ile Ala Ala Thr Pro Thr Leu Ala Ala Gly Leu
                325                 330                 335
Asn Leu Pro Ala Arg Arg Val Ile Ile Arg Asp Tyr Asn Arg Phe Ala
            340                 345                 350
Ser Gly Leu Gly Met Val Pro Ile Pro Val Gly Glu Tyr His Gln Met
            355                 360                 365
Ala Gly Arg Ala Gly Arg Pro His Leu Asp Pro Tyr Gly Glu Ala Val
            370                 375                 380
Leu Leu Ala Lys Asp Ala Pro Ser Val Glu Arg Leu Phe Glu Thr Phe
385                 390                 395                 400
Ile Asp Ala Glu Ala Glu Arg Val Asp Ser Gln Cys Val Asp Ala
                    405                 410                 415
Ser Leu Cys Ala His Ile Leu Ser Leu Ile Ala Thr Gly Phe Ala His
                420                 425                 430
Asp Gln Glu Ala Leu Ser Ser Phe Met Glu Arg Thr Phe Tyr Phe Phe
            435                 440                 445
Gln His Pro Lys Thr Arg Ser Leu Pro Arg Leu Val Ala Asp Ala Ile
            450                 455                 460
Arg Phe Leu Thr Thr Ala Gly Met Val Glu Glu Arg Glu Asn Thr Leu
465                 470                 475                 480
Ser Ala Thr Arg Leu Gly Ser Leu Val Ser Arg Leu Tyr Leu Asn Pro
                485                 490                 495
Cys Thr Ala Arg Leu Ile Leu Asp Ser Leu Lys Ser Cys Lys Thr Pro
                500                 505                 510
Thr Leu Ile Gly Leu Leu His Val Ile Cys Val Ser Pro Asp Met Gln
            515                 520                 525
Arg Leu Tyr Leu Lys Ala Ala Asp Thr Gln Leu Leu Arg Thr Phe Leu
            530                 535                 540
Phe Lys His Lys Asp Asp Leu Ile Leu Pro Leu Pro Phe Glu Gln Glu
545                 550                 555                 560
Glu Glu Glu Leu Trp Leu Ser Gly Leu Lys Thr Ala Leu Val Leu Thr
                565                 570                 575
Asp Trp Ala Asp Glu Phe Ser Glu Gly Met Ile Glu Glu Arg Tyr Gly
            580                 585                 590
Ile Gly Ala Gly Asp Leu Tyr Asn Ile Val Asp Ser Gly Lys Trp Leu
            595                 600                 605
Leu His Gly Thr Glu Arg Leu Val Ser Val Glu Met Pro Glu Met Ser
            610                 615                 620
Gln Val Val Lys Thr Leu Ser Val Arg Val His His Gly Val Lys Ser
625                 630                 635                 640
Glu Leu Leu Pro Leu Val Ala Leu Arg Asn Ile Gly Arg Val Arg Ala
                645                 650                 655
Arg Thr Leu Tyr Asn Ala Gly Tyr Pro Asp Pro Glu Ala Val Ala Arg
                660                 665                 670
```

```
Ala Gly Leu Ser Thr Ile Ala Arg Ile Ile Gly Glu Gly Ile Ala Arg
            675                 680                 685

Gln Val Ile Asp Glu Ile Thr Gly Val Lys Arg Ser Gly Ile His Ser
        690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
                755                 760                 765

Ser Glu Lys Glu Asn Ser Ser Ser Asp Lys Thr Glu Glu Ile Pro Asp
        770                 775                 780

Thr Gln Lys Ile Arg Gly Gln Ser Ser Trp Glu Asp Phe Gly Cys
785                 790                 795
```

<210> SEQ ID NO 22
<211> LENGTH: 1756
<212> TYPE: PRT
<213> ORGANISM: Escherichia coli

<400> SEQUENCE: 22

```
Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
```

-continued

```
                245                 250                 255
Ala Ala Leu Asp Thr Arg Lys Ser Lys Gln His Val Asp Pro Glu Ile
            260                 265                 270
Arg Met Ala Glu Trp Met Gln Thr Leu Lys Glu Thr Gly Phe Asp Ile
            275                 280                 285
Arg Ala Tyr Arg Asp Ala Ala Asp Gln Arg Thr Glu Ile Arg Thr Gln
            290                 295                 300
Ala Pro Gly Pro Ala Ser Gln Asp Gly Pro Asp Val Gln Gln Ala Val
305                 310                 315                 320
Thr Gln Ala Ile Ala Gly Leu Ser Glu Arg Lys Val Gln Phe Thr Tyr
                325                 330                 335
Thr Asp Val Leu Ala Arg Thr Val Gly Ile Leu Pro Pro Glu Asn Gly
            340                 345                 350
Val Ile Glu Arg Ala Arg Ala Gly Ile Asp Glu Ala Ile Ser Arg Glu
            355                 360                 365
Gln Leu Ile Pro Leu Asp Arg Glu Lys Gly Leu Phe Thr Ser Gly Ile
            370                 375                 380
His Val Leu Asp Glu Leu Ser Val Arg Ala Leu Ser Arg Asp Ile Met
385                 390                 395                 400
Lys Gln Asn Arg Val Thr Val His Pro Glu Lys Ser Val Pro Arg Thr
                405                 410                 415
Ala Gly Tyr Ser Asp Ala Val Ser Val Leu Ala Gln Asp Arg Pro Ser
            420                 425                 430
Leu Ala Ile Val Ser Gly Gln Gly Gly Ala Ala Gly Gln Arg Glu Arg
            435                 440                 445
Val Ala Glu Leu Val Met Met Ala Arg Glu Gln Gly Arg Glu Val Gln
            450                 455                 460
Ile Ile Ala Ala Asp Arg Arg Ser Gln Met Asn Leu Lys Gln Asp Glu
465                 470                 475                 480
Arg Leu Ser Gly Glu Leu Ile Thr Gly Arg Arg Gln Leu Leu Glu Gly
                485                 490                 495
Met Ala Phe Thr Pro Gly Ser Thr Val Ile Val Asp Gln Gly Glu Lys
            500                 505                 510
Leu Ser Leu Lys Glu Thr Leu Thr Leu Leu Asp Gly Ala Ala Arg His
            515                 520                 525
Asn Val Gln Val Leu Ile Thr Asp Ser Gly Gln Arg Thr Gly Thr Gly
            530                 535                 540
Ser Ala Leu Met Ala Met Lys Asp Ala Gly Val Asn Thr Tyr Arg Trp
545                 550                 555                 560
Gln Gly Gly Glu Gln Arg Pro Ala Thr Ile Ile Ser Glu Pro Asp Arg
                565                 570                 575
Asn Val Arg Tyr Ala Arg Leu Ala Gly Asp Phe Ala Ala Ser Val Lys
            580                 585                 590
Ala Gly Glu Glu Ser Val Ala Gln Val Ser Gly Val Arg Glu Gln Ala
            595                 600                 605
Ile Leu Thr Gln Ala Ile Arg Ser Glu Leu Lys Thr Gln Gly Val Leu
            610                 615                 620
Gly His Pro Glu Val Thr Met Thr Ala Leu Ser Pro Val Trp Leu Asp
625                 630                 635                 640
Ser Arg Ser Arg Tyr Leu Arg Asp Met Tyr Arg Pro Gly Met Val Met
                645                 650                 655
Glu Gln Trp Asn Pro Glu Thr Arg Ser His Asp Arg Tyr Val Ile Asp
            660                 665                 670
```

```
Arg Val Thr Ala Gln Ser His Ser Leu Thr Leu Arg Asp Ala Gln Gly
            675                 680                 685

Glu Thr Gln Val Val Arg Ile Ser Ser Leu Asp Ser Ser Trp Ser Leu
        690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
                755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr Gln Phe Arg Ala Val Met Ser Ala
        995                 1000                1005

Val Asn Met Leu Pro Ala Ser Glu Arg Pro Arg Val Val Gly Leu
            1010                1015                1020

Gly Pro Thr His Arg Ala Val Gly Glu Met Arg Ser Ala Gly Val
    1025                1030                1035

Asp Ala Gln Thr Leu Ala Ser Phe Leu His Asp Thr Gln Leu Gln
    1040                1045                1050

Gln Arg Ser Gly Glu Thr Pro Asp Phe Ser Asn Thr Leu Phe Leu
    1055                1060                1065

Leu Asp Glu Ser Ser Met Val Gly Asn Thr Glu Met Ala Arg Ala
    1070                1075                1080
```

-continued

```
Tyr Ala Leu Ile Ala Ala Gly Gly Arg Ala Val Ala Ser Gly
    1085            1090            1095

Asp Thr Asp Gln Leu Gln Ala Ile Ala Pro Gly Gln Ser Phe Arg
    1100            1105            1110

Leu Gln Gln Thr Arg Ser Ala Ala Asp Val Val Ile Met Lys Glu
    1115            1120            1125

Ile Val Arg Gln Thr Pro Glu Leu Arg Glu Ala Val Tyr Ser Leu
    1130            1135            1140

Ile Asn Arg Asp Val Glu Arg Ala Leu Ser Gly Leu Glu Ser Val
    1145            1150            1155

Lys Pro Ser Gln Val Pro Arg Leu Glu Gly Ala Trp Ala Pro Glu
    1160            1165            1170

His Ser Val Thr Glu Phe Ser His Ser Gln Glu Ala Lys Leu Ala
    1175            1180            1185

Glu Ala Gln Gln Lys Ala Met Leu Lys Gly Glu Ala Phe Pro Asp
    1190            1195            1200

Ile Pro Met Thr Leu Tyr Glu Ala Ile Val Arg Asp Tyr Thr Gly
    1205            1210            1215

Arg Thr Pro Glu Ala Arg Glu Gln Thr Leu Ile Val Thr His Leu
    1220            1225            1230

Asn Glu Asp Arg Arg Val Leu Asn Ser Met Ile His Asp Ala Arg
    1235            1240            1245

Glu Lys Ala Gly Glu Leu Gly Lys Glu Gln Val Met Val Pro Val
    1250            1255            1260

Leu Asn Thr Ala Asn Ile Arg Asp Gly Glu Leu Arg Arg Leu Ser
    1265            1270            1275

Thr Trp Glu Lys Asn Pro Asp Ala Leu Ala Leu Val Asp Asn Val
    1280            1285            1290

Tyr His Arg Ile Ala Gly Ile Ser Lys Asp Asp Gly Leu Ile Thr
    1295            1300            1305

Leu Gln Asp Ala Glu Gly Asn Thr Arg Leu Ile Ser Pro Arg Glu
    1310            1315            1320

Ala Val Ala Glu Gly Val Thr Leu Tyr Thr Pro Asp Lys Ile Arg
    1325            1330            1335

Val Gly Thr Gly Asp Arg Met Arg Phe Thr Lys Ser Asp Arg Glu
    1340            1345            1350

Arg Gly Tyr Val Ala Asn Ser Val Trp Thr Val Thr Ala Val Ser
    1355            1360            1365

Gly Asp Ser Val Thr Leu Ser Asp Gly Gln Gln Thr Arg Val Ile
    1370            1375            1380

Arg Pro Gly Gln Glu Arg Ala Glu Gln His Ile Asp Leu Ala Tyr
    1385            1390            1395

Ala Ile Thr Ala His Gly Ala Gln Gly Ala Ser Glu Thr Phe Ala
    1400            1405            1410

Ile Ala Leu Glu Gly Thr Glu Gly Asn Arg Lys Leu Met Ala Gly
    1415            1420            1425

Phe Glu Ser Ala Tyr Val Ala Leu Ser Arg Met Lys Gln His Val
    1430            1435            1440

Gln Val Tyr Thr Asp Asn Arg Gln Gly Trp Thr Asp Ala Ile Asn
    1445            1450            1455

Asn Ala Val Gln Lys Gly Thr Ala His Asp Val Leu Glu Pro Lys
    1460            1465            1470

Pro Asp Arg Glu Val Met Asn Ala Gln Arg Leu Phe Ser Thr Ala
```

```
                    1475               1480               1485

Arg Glu Leu Arg Asp Val Ala Ala Gly Arg Ala Val Leu Arg Gln
    1490               1495               1500

Ala Gly Leu Ala Gly Gly Asp Ser Pro Ala Arg Phe Ile Ala Pro
    1505               1510               1515

Gly Arg Lys Tyr Pro Gln Pro Tyr Val Ala Leu Pro Ala Phe Asp
    1520               1525               1530

Arg Asn Gly Lys Ser Ala Gly Ile Trp Leu Asn Pro Leu Thr Thr
    1535               1540               1545

Asp Asp Gly Asn Gly Leu Arg Gly Phe Ser Gly Glu Gly Arg Val
    1550               1555               1560

Lys Gly Ser Gly Asp Ala Gln Phe Val Ala Leu Gln Gly Ser Arg
    1565               1570               1575

Asn Gly Glu Ser Leu Leu Ala Asp Asn Met Gln Asp Gly Val Arg
    1580               1585               1590

Ile Ala Arg Asp Asn Pro Asp Ser Gly Val Val Val Arg Ile Ala
    1595               1600               1605

Gly Glu Gly Arg Pro Trp Asn Pro Gly Ala Ile Thr Gly Gly Arg
    1610               1615               1620

Val Trp Gly Asp Ile Pro Asp Asn Ser Val Gln Pro Gly Ala Gly
    1625               1630               1635

Asn Gly Glu Pro Val Thr Ala Glu Val Leu Ala Gln Arg Gln Ala
    1640               1645               1650

Glu Glu Ala Ile Arg Arg Glu Thr Glu Arg Arg Ala Asp Glu Ile
    1655               1660               1665

Val Arg Lys Met Ala Glu Asn Lys Pro Asp Leu Pro Asp Gly Lys
    1670               1675               1680

Thr Glu Leu Ala Val Arg Asp Ile Ala Gly Gln Glu Arg Asp Arg
    1685               1690               1695

Ser Ala Ile Ser Glu Arg Glu Thr Ala Leu Pro Glu Ser Val Leu
    1700               1705               1710

Arg Glu Ser Gln Arg Glu Arg Glu Ala Val Arg Glu Val Ala Arg
    1715               1720               1725

Glu Asn Leu Leu Gln Glu Arg Leu Gln Gln Met Glu Arg Asp Met
    1730               1735               1740

Val Arg Asp Leu Gln Lys Glu Lys Thr Leu Gly Gly Asp
    1745               1750               1755

<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80
```

-continued

```
Asn Glu Ala Arg Asp Ile Lys Lys Val Gln Asp Val Lys Val Ala Val
                 85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
            115                 120                 125

Glu Ile Tyr Leu Lys Arg Gln Glu Leu Asn Ser Ala Arg Asp Ser Tyr
        130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Ile Asn Asp
        195                 200                 205

His Ala Ile Lys Asp Gly Met Cys Gly Tyr Glu Leu Val Lys Arg Glu
        210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
            275                 280                 285

Ile Thr Glu Leu Glu Ala Asn Leu Asp Leu Leu Ala Asp Asp Asn Ile
        290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
            355                 360                 365

Gln Ile Leu Leu Ser Glu Ala Ser Glu Leu Gly Ala Lys Leu Asp Glu
        370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
            435                 440                 445

Asn Val Thr Glu Pro Leu Phe Asn Ser Leu Phe Ser Val Ile Leu Met
        450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
```

```
                500                 505                 510
Arg Asp Asp Arg His Val Thr Glu Leu Leu Glu Gln Val Leu Leu Asp
            515                 520                 525

Ser Ile Glu Asn Ser Lys Gly Asn Val Ile Leu Phe Phe Gln Ser Ala
            530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Asn Gly Lys Ala Val Leu Leu Ser
            580                 585                 590

Tyr Leu Trp Gly Thr Leu Ser Glu Gly Ile Asp Tyr Arg Asp Gly Arg
            595                 600                 605

Gly Arg Thr Val Ile Ile Gly Val Gly Tyr Pro Ala Leu Asn Asp
            610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
                660                 665                 670

Ile Leu Leu Asp Gly Arg Phe Leu Thr Asp Ser Lys Lys Arg Phe Gly
            675                 680                 685

Lys Phe Ser Val Phe Glu Val Phe Pro Pro Ala Glu Arg Ser Glu Phe
            690                 695                 700

Val Asp Val Asp Pro Glu Lys Val Lys Tyr Ser Leu Met Asn Phe Phe
705                 710                 715                 720

Met Asp Asn Asp Glu Gln
            725

<210> SEQ ID NO 24
<211> LENGTH: 439
<212> TYPE: PRT
<213> ORGANISM: Enterobacteria phage T4

<400> SEQUENCE: 24

Met Thr Phe Asp Asp Leu Thr Glu Gly Gln Lys Asn Ala Phe Asn Ile
1               5                  10                  15

Val Met Lys Ala Ile Lys Glu Lys Lys His Val Thr Ile Asn Gly
            20                  25                  30

Pro Ala Gly Thr Gly Lys Thr Thr Leu Thr Lys Phe Ile Ile Glu Ala
            35                  40                  45

Leu Ile Ser Thr Gly Glu Thr Gly Ile Ile Leu Ala Ala Pro Thr His
            50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Ile Gly Ile Gly Asp Asn
            130                 135                 140
```

```
Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Asp Gly His Gly Val Arg Gly
        195                 200             205

Phe Thr Gly Asp Thr Ala Leu Arg Asp Phe Met Val Asn Tyr Phe Ser
        210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
            245                 250                 255

Phe Glu Thr Asp Lys Asp Phe Ile Val Gly Glu Ile Ile Val Met Gln
        260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Glu Ala Glu Tyr
290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
        370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435

<210> SEQ ID NO 25
<211> LENGTH: 970
<212> TYPE: PRT
<213> ORGANISM: Clostridium botulinum

<400> SEQUENCE: 25

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80
```

```
Thr Phe Ser Val Pro Lys Ser Trp Ser Leu Leu Ala Leu Val Gly Lys
             85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
            165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
            210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
            245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
            275                 280                 285

Ala Arg Thr Lys Ala Leu Gly Gln Gly Met Ala Thr Arg Ile Gly
            290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
            325                 330                 335

Gln Asp Arg Gln Thr Ile Ala Ala Gln Ala Val Ala Ser Ala Val
            340                 345                 350

Arg His Leu Ser Gln Arg Glu Ala Ala Phe Glu Arg Thr Ala Leu Tyr
            355                 360                 365

Lys Ala Ala Leu Asp Phe Gly Leu Pro Thr Thr Ile Ala Asp Val Glu
370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
            405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ser Val Gln Ala Ala Leu
            435                 440                 445

Thr Gly Gln Gly Phe Arg Leu Asn Glu Gly Gln Leu Ala Ala Ala Arg
450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
            485                 490                 495
```

```
Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
    770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
```

```
              915                 920                 925
Val Thr Gly Ser Val Lys Pro Thr Ala Thr Lys Gly Ser Val Asp
        930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 26
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 26
gttttcgcat ttatcgtgaa acgctttcgc gtttttcgtg cgccgcttca                 50

<210> SEQ ID NO 27
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 27
caaaagcgta aatagcactt tgcgaaagcg caaaaagcac gcggcgaagu                 50

<210> SEQ ID NO 28
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 28
caaaagcgta aatagcactt tgcgaaagcg caaaaagcac gcggcgaagu ctag            54

<210> SEQ ID NO 29
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 29
gccatcagat tgtgtttgtt agtcgctttt ttttttggga attttttttt tggaattttt      60 ttttgcgct aacaacctcc tgccgttttg cccgtgcata tcggtcacga acaaatctga      120
ttactaaaca cagtagcctg gatttgttct atcagtaatc gaccttattc ctaattaaat     180
agagcaaatc cccttattgg gggtaagaca tgaagatgcc agaaaaacat gacctgttgg     240
ccgccattct cgcggcaaag gaacaaggca tcggggcaat ccttgcgttt gcaatggcgt     300
accttcgcgg cagatataat ggcggtgcgt ttacaaaaac agtaatcgac gcaacgatgt     360
gcgccattat cgcctagttc attcgtgacc ttctcgactt cgccggacta agtagcaatc     420
tcgcttatat aacgagcgtg tttatcggct acatcggtac tgactcgatt ggttcgctta     480
tcaaacgctt cgctgctaaa aaagccggag tagaagatgg tagaaatcaa taatcaacgt     540
aaggcgttcc tcgatatgct ggcgtggtcg gagggaactg ataacggacg tcagaaaacc    600
agaaatcatg gttatgacgt cattgtaggc ggagagctat ttactgatta ctccgatcac    660
```

```
cctcgcaaac ttgtcacgct aaacccaaaa ctcaaatcaa caggcgccgg acgctaccag    720
cttctttccc gttggtggga tgcctaccgc aagcagcttg ccctgaaaga cttctctccg    780
aaaagtcagg acgctgtggc attgcagcag attaaggagc gtggcgcttt acctatgatt    840
gatcgtggtg atatccgtca ggcaatcgac cgttgcagca atatctgggc ttcactgccg    900
ggcgctggtt atggtcagtt cgagcataag gctgacagcc tgattgcaaa attcaaagaa    960
gcgggcggaa cggtcagaga gattgatgta tgagcagagt caccgcgatt atctccgctc   1020
tggttatctg catcatcgtc tgcctgtcat gggctgttaa tcattaccgt gataacgcca   1080
ttacctacaa agcccagcgc gacaaaaatg ccagagaact gaagctggcg aacgcggcaa   1140
ttactgacat gcagatgcgt cagcgtgatg ttgctgcgct cgatgcaaaa tacacgaagg   1200
agttagctga tgctaaagct gaaaatgatg ctctgcgtga tgatgttgcc gctggtcgtc   1260
gtcggttgca catcaaagca gtctgtcagt cagtgcgtga agccaccacc gcctccggcg   1320
tggataatgc agcctccccc cgactggcag acaccgctga acgggattat ttcaccctca   1380
gagagaggct gatcactatg caaaaacaac tggaaggaac ccagaagtat attaatgagc   1440
agtgcagata gagttgccca tatcgatggg caactcatgc aattattgtg agcaatacac   1500
acgcgcttcc agcggagtat aaatgcctaa agtaataaaa ccgagcaatc catttacgaa   1560
tgtttgctgg gtttctgttt taacaacatt ttctgcgccg ccacaaattt tggctgcatc   1620
gacagttttc ttctgcccaa ttccagaaac gaagaaatga tgggtgatgg tttccttttgg  1680 tgctactgct gccggtttgt tttgaacagt aaacgtctgt tgagcacatc ctgtaataag   1740
cagggccagc gcagtagcga gtagcatttt tttcatggtg ttattcccga tgcttttttga  1800 agttcgcaga atcgtatgtg tagaaaatta acaaaccct aaacaatgag ttgaaatttc    1860
atattgttaa tatttattaa tgtatgtcag gtgcgatgaa tcgtcattgt attcccggat   1920
taactatgtc cacagccctg acggggaact tctctgcggg agtgtccggg aataattaaa   1980
acgatgcaca cagggtttag cgcgtacacg tattgcatta tgccaacgcc ccggtgctga   2040
cacggaagaa accggacgtt atgatttagc gtggaaagat ttgtgtagtg ttctgaatgc   2100
tctcagtaaa tagtaatgaa ttatcaaagg tatagtaata tcttttatgt tcatggatat   2160
ttgtaaccca tcggaaaact cctgctttag caagattttc cctgtattgc tgaaatgtga   2220
tttctcttga tttcaaccta tcataggacg tttctataag atgcgtgttt cttgagaatt   2280
taacatttac aaccttttta agtcctttta ttaacacggt gttatcgttt ctaacacga   2340 tgtgaatatt atctgtggct agatagtaaa tataatgtga gacgttgtga cgttttagtt   2400
cagaataaaa caattcacag tctaaatctt ttcgcacttg atcgaatatt tctttaaaaa   2460
tggcaacctg agccattggt aaaaccttcc atgtgatacg agggcgcgta gtttgcatta   2520 tcgttttat cgtttcaatc tggtctgacc tccttgtgtt ttgttgatga tttatgtcaa    2580
atattaggaa tgttttcact taatagtatt ggttgcgtaa caaagtgcgg tcctgctggc   2640
attctggagg gaaatacaac cgacagatgt atgtaaggcc aacgtgctca atcttcata   2700 cagaaagatt tgaagtaata ttttaaccgc tagatgaaga gcaagcgcat ggagcgacaa   2760
aatgaataaa gaacaatctg ctgatgatcc ctccgtggat ctgattcgtg taaaaaatat   2820
gcttaatagc accatttcta tgagttaccc tgatgttgta attgcatgta tagaacataa   2880
ggtgtctctg gaagcattca gagcaattga ggcagcgttg gtgaagcacg ataataatat   2940
gaaggattat tccctggtgg ttgactgatc accataactg ctaatcattc aaactattta   3000
gtctgtgaca gagccaacac gcagtctgtc actgtcagga aagtggtaaa actgcaactc   3060
```

```
aattactgca atgccctcgt aattaagtga atttacaata tcgtcctgtt cggagggaag    3120
aacgcgggat gttcattctt catcactttt aattgatgta tatgctctct tttctgacgt    3180
tagtctccga cggcaggctt caatgaccca ggctgagaaa ttcccggacc cttttttgctc   3240 aagagcgatg ttaatttgtt caatcatttg gttaggaaag cggatgttgc gggttgttgt    3300
tctgcgggtt ctgttcttcg ttgacatgag gttgccccgt attcagtgtc gctgatttgt    3360
attgtctgaa gttgttttta cgttaagttg atgcagatca attaatacga tacctgcgtc    3420
ataattgatt atttgacgtg gtttgatggc ctccacgcac gttgtgatat gtagatgata    3480
atcattatca ctttacgggt cctttccggt gaaaaaaaag gtaccaaaaa aacatcgtc    3540 gtgagtagtg aaccgtaagc                                                3560
```

<210> SEQ ID NO 30
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 30

```
gcttacggtt cactactcac gacgatgttt ttttggtac cttttttttc accggaaagg     60
acccgtaaag tgataatgat tatcatctac atatcacaac gtgcgtggag gccatcaaac    120
cacgtcaaat aatcaattat gacgcaggta tcgtattaat tgatctgcat caacttaacg    180
taaaaacaac ttcagacaat acaaatcagc gacactgaat acggggcaac ctcatgtcaa    240
cgaagaacag aacccgcaga caacaaccc gcaacatccg ctttcctaac caaatgattg     300
aacaaattaa catcgctctt gagcaaaaag ggtccgggaa tttctcagcc tgggtcattg    360
aagcctgccg tcggagacta acgtcagaaa agagagcata tacatcaatt aaaagtgatg    420
aagaatgaac atcccgcgtt cttccctccg aacaggacga tattgtaaat tcacttaatt    480
acgagggcat tgcagtaatt gagttgcagt tttaccactt tcctgacagt gacagactgc    540
gtgttggctc tgtcacagac taaatagttt gaatgattag cagttatggt gatcagtcaa    600
ccaccaggga ataatccttc atattattat cgtgcttcac caacgctgcc tcaattgctc    660
tgaatgcttc cagagacacc ttatgttcta tacatgcaat tacaacatca gggtaactca    720
tagaaatggt gctattaagc atattttta cacgaatcag atccacgag ggatcatcag      780 cagattgttc tttattcatt ttgtcgctcc atgcgcttgc tcttcatcta gcggttaaaa    840
tattacttca aatctttctg tatgaagatt tgagcacgtt ggccttacat acatctgtcg    900
gttgtatttc cctccagaat gccagcagga ccgcactttg ttacgcaacc aatactatta    960
agtgaaaaca ttcctaatat ttgacataaa tcatcaacaa acacaagga ggtcagacca     1020 gattgaaacg ataaaaacga taatgcaaac tacgcgccct cgtatcacat ggaaggtttt    1080
accaatggct caggttgcca ttttaaaga aatattcgat caagtgcgaa agatttaga      1140 ctgtgaattg ttttattctg aactaaaacg tcacaacgtc tcacattata tttactatct    1200
agccacagat aatattcaca tcgtgttaga aaacgataac accgtgttaa taaaaggact    1260 taaaaggtt gtaaatgtta aattctcaag aaacacgcat cttatagaaa cgtcctatga     1320
taggttgaaa tcaagagaaa tcacattttca gcaatacagg gaaaatcttg ctaaagcagg    1380
agttttccga tgggttacaa atatccatga acataaaaga tattactata cctttgataa    1440
ttcattacta tttactgaga gcattcagaa cactacacaa atctttccac gctaaatcat    1500
```

```
aacgtccggt ttcttccgtg tcagcaccgg ggcgttggca taatgcaata cgtgtacgcg    1560
ctaaaccctg tgtgcatcgt tttaattatt cccggacact cccgcagaga agttccccgt    1620
cagggctgtg gacatagtta atccgggaat acaatgacga ttcatcgcac ctgacataca    1680
ttaataaata ttaacaatat gaaatttcaa ctcattgttt agggtttgtt taattttcta    1740
cacatacgat tctgcgaact tcaaaaagca tcgggaataa caccatgaaa aaaatgctac    1800
tcgctactgc gctggccctg cttattacag gatgtgctca acagacgttt actgttcaaa    1860
acaaaccggc agcagtagca ccaaaggaaa ccatcaccca tcatttcttc gtttctggaa    1920
ttgggcagaa gaaaactgtc gatgcagcca aaatttgtgg cggcgcagaa aatgttgtta    1980
aaacagaaac ccagcaaaca ttcgtaaatg gattgctcgg ttttattact ttaggcattt    2040
atactccgct ggaagcgcgt gtgtattgct cacaataatt gcatgagttg cccatcgata    2100
tgggcaactc tatctgcact gctcattaat atacttctgg gttccttcca gttgtttttg    2160
catagtgatc agcctctctc tgagggtgaa ataatcccgt tcagcggtgt ctgccagtcg    2220
gggggaggct gcattatcca cgccggaggc ggtggtggct tcacgcactg actgacagac    2280
tgctttgatg tgcaaccgac gacgaccagc ggcaacatca tcacgcagag catcattttc    2340
agctttagca tcagctaact ccttcgtgta ttttgcatcg agcgcagcaa catcacgctg    2400
acgcatctgc atgtcagtaa ttgccgcgtt cgccagcttc agttctctgg cattttttgtc   2460 gcgctgggct ttgtaggtaa tggcgttatc acggtaatga ttaacagccc atgacaggca    2520
gacgatgatg cagataacca gagcggagat aatcgcggtg actctgctca tacatcaatc    2580
tctctgaccg ttccgcccgc ttctttgaat tttgcaatca ggctgtcagc cttatgctcg    2640
aactgaccat aaccagcgcc cggcagtgaa gcccagatat tgctgcaacg gtcgattgcc    2700
tgacggatat caccacgatc aatcataggt aaagcgccac gctccttaat ctgctgcaat    2760
gccacagcgt cctgactttt cggagagaag tctttcaggc caagctgctt gcggtaggca    2820
tcccaccaac gggaaagaag ctggtagcgt ccggcgcctg ttgatttgag ttttgggttt    2880
agcgtgacaa gtttgcgagg gtgatcggag taatcagtaa atagctctcc gcctacaatg    2940
acgtcataac catgatttct ggttttctga cgtccgttat cagttccctc cgaccacgcc    3000
agcatatcga ggaacgccett acgttgatta ttgatttcta ccatcttcta ctccggcttt    3060
tttagcagcg aagcgtttga taagcgaacc aatcgagtca gtaccgatgt agccgataaa    3120
cacgctcgtt atataagcga gattgctact tagtccggcg aagtcgagaa ggtcacgaat    3180
gaactaggcg ataatggcgc acatcgttgc gtcgattact gttttgtaa acgcaccgcc     3240 attatatctg ccgcgaaggt acgccattgc aaacgcaagg attgccccga tgccttgttc    3300
ctttgccgcg agaatggcgg ccaacaggtc atgtttttct ggcatcttca tgtcttaccc    3360
ccaataaggg gatttgctct atttaattag gaataaggtc gattactgat agaacaaatc    3420
caggctactg tgtttagtaa tcagatttgt tcgtgaccga tatgcacggg caaaacggca    3480
ggaggttgtt agcgcaaaaa aaaaattcca aaaaaaaaat tccaaaaaaa aaaagcgact    3540
aacaaacaca atctgatggc                                                3560
```

<210> SEQ ID NO 31
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 31

```
gccatcagat tgtgtttgtt agtcgctttt ttttttggaa attttttttt tggaattttt      60
tttttgcgct aacaacctcc tgccg                                            85

<210> SEQ ID NO 32
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 32
gcttacggtt cactactcac gacgatgttt ttttggtac cttttttttc accggaaagg      60
acccgtaaag tg                                                          72

<210> SEQ ID NO 33
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 33
tttttttttt tttttttttt tttttttttt tttttttttt tttttt                    46

<210> SEQ ID NO 34
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 34
ggttgtttct gttggtgctg atattgc                                          27

<210> SEQ ID NO 35
<211> LENGTH: 3587
<212> TYPE: DNA
<213> ORGANISM: Artificial Sequence
<220> FEATURE:
<223> OTHER INFORMATION: Synthetic Polynucleotide

<400> SEQUENCE: 35
gccatcagat tgtgtttgtt agtcgctgcc atcagattgt gtttgttagt cgcttttttt      60
ttttggaatt ttttttttgg aattttttttt ttgcgctaac aacctcctgc cgttttgccc    120
gtgcatatcg gtcacgaaca atctgattac taaacacag tagcctggat tgttctatc       180 agtaatcgac cttattccta attaaataga gcaaatcccc ttattggggg taagacatga    240
agatgccaga aaaacatgac ctgttggccg ccattctcgc ggcaaaggaa caaggcatcg    300
gggcaatcct tgcgtttgca atggcgtacc ttcgcggcag atataatggc ggtgcgttta    360
caaaaacagt aatcgacgca acgatgtgcg ccattatcgc ctagttcatt cgtgaccttc    420
tcgacttcgc cggactaagt agcaatctcg cttatataac gagcgtgttt atcggctaca    480
tcggtactga ctcgattggt tcgcttatca aacgcttcgc tgctaaaaaa gccggagtag    540
aagatggtag aaatcaataa tcaacgtaag gcgttcctcg atatgctggc gtggtcggag    600
ggaactgata acggacgtca gaaaaccaga atcatggtt atgacgtcat tgtaggcgga    660 gagctatttta ctgattactc cgatcaccct cgcaaacttg tcacgctaaa cccaaaactc    720
aaatcaacag gcgccggacg ctaccagctt ctttcccgtt ggtgggatgc ctaccgcaag    780
```

```
cagcttggcc tgaaagactt ctctccgaaa agtcaggacg ctgtggcatt gcagcagatt    840
aaggagcgtg gcgctttacc tatgattgat cgtggtgata tccgtcaggc aatcgaccgt    900
tgcagcaata tctgggcttc actgccgggc gctggttatg gtcagttcga gcataaggct    960
gacagcctga ttgcaaaatt caaagaagcg ggcggaacgg tcagagagat tgatgtatga   1020
gcagagtcac cgcgattatc tccgctctgg ttatctgcat catcgtctgc ctgtcatggg   1080
ctgttaatca ttaccgtgat aacgccatta cctacaaagc ccagcgcgac aaaaatgcca   1140
gagaactgaa gctggcgaac gcggcaatta ctgacatgca gatgcgtcag cgtgatgttg   1200
ctgcgctcga tgcaaaatac acgaaggagt tagctgatgc taaagctgaa atgatgctc    1260 tgcgtgatga tgttgccgct ggtcgtcgtc ggttgcacat caaagcagtc tgtcagtcag   1320
tgcgtgaagc caccaccgcc tccggcgtgg ataatgcagc ctccccccga ctggcagaca   1380
ccgctgaacg ggattatttc accctcagag agaggctgat cactatgcaa aaacaactgg   1440
aaggaaccca gaagtatatt aatgagcagt gcagatagag ttgcccatat cgatgggcaa   1500
ctcatgcaat tattgtgagc aatacacacg cgcttccagc ggagtataaa tgcctaaagt   1560
aataaaaccg agcaatccat ttacgaatgt ttgctgggtt tctgttttaa caacatttc    1620 tgcgccgcca caaattttgg ctgcatcgac agttttcttc tgcccaattc agaaacgaa    1680 gaaatgatgg gtgatggttt cctttggtgc tactgctgcc ggtttgtttt gaacagtaaa   1740
cgtctgttga gcacatcctg taataagcag ggccagcgca gtagcgagta gcattttttt   1800
catggtgtta ttcccgatgc tttttgaagt tcgcagaatc gtatgtgtag aaaattaaac   1860
aaaccctaaa caatgagttg aaatttcata ttgttaatat ttattaatgt atgtcaggtg   1920
cgatgaatcg tcattgtatt cccggattaa ctatgtccac agccctgacg gggaacttct   1980
ctgcgggagt gtccgggaat aattaaaacg atgcacacag ggtttagcgc gtacacgtat   2040
tgcattatgc caacgccccg gtgctgacac ggaagaaacc ggacgttatg atttagcgtg   2100
gaaagatttg tgtagtgttc tgaatgctct cagtaaatag taatgaatta tcaaaggtat   2160
agtaatatct tttatgttca tggatatttg taacccatcg gaaaactcct gctttagcaa   2220
gattttccct gtattgctga aatgtgattt ctcttgattt caacctatca taggacgttt   2280
ctataagatg cgtgtttctt gagaatttaa catttacaac cttttttaagt cctttttatta   2340 acacggtgtt atcgttttct aacacgatgt gaatattatc tgtggctaga tagtaaatat   2400
aatgtgagac gttgtgacgt tttagttcag aataaaacaa ttcacagtct aaatcttttc   2460
gcacttgatc gaatatttct ttaaaaatgg caacctgagc cattggtaaa accttccatg   2520
tgatacgagg gcgcgtagtt tgcattatcg ttttatcgt ttcaatctgg tctgacctcc     2580
ttgtgttttg ttgatgattt atgtcaaata ttaggaatgt tttcacttaa tagtattggt   2640
tgcgtaacaa agtgcggtcc tgctggcatt ctggagggaa atacaaccga cagatgtatg   2700
taaggccaac gtgctcaaat cttcatacag aaagatttga agtaatattt taaccgctag   2760
atgaagagca agcgcatgga gcgacaaaat gaataaagaa caatctgctg atgatccctc   2820
cgtggatctg attcgtgtaa aaaatatgct taatagcacc attctatga gttaccctga     2880 tgttgtaatt gcatgtatag aacataaggt gtctctggaa gcattcagag caattgaggc   2940
agcgttggtg aagcacgata ataatatgaa ggattattcc ctggtggttg actgatcacc   3000
ataactgcta atcattcaaa ctatttagtc tgtgacagag ccaacacgca gtctgtcact   3060
gtcaggaaag tggtaaaact gcaactcaat tactgcaatg ccctcgtaat taagtgaatt   3120
tacaatatcg tcctgttcgg agggaagaac gcgggatgtt cattcttcat cacttttaat   3180
```

-continued

```
tgatgtatat gctctctttt ctgacgttag tctccgacgg caggcttcaa tgacccaggc    3240
tgagaaattc ccggacccnt tttgctcaag agcgatgtta atttgttcaa tcatttggtt    3300
aggaaagcgg atgttgcggg ttgttgttct gcgggttctg ttcttcgttg acatgaggtt    3360
gccccgtatt cagtgtcgct gatttgtatt gtctgaagtt gttttacgt taagttgatg     3420 cagatcaatt aatacgatac ctgcgtcata attgattatt tgacgtggtt tgatggcctc    3480
cacgcacgtt gtgatatgta gatgataatc attatcactt tacgggtcct ttccggtgaa    3540
aaaaaaggta ccaaaaaaaa catcgtcgtg agtagtgaac cgtaagc                  3587
```

<210> SEQ ID NO 36
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 36

```
gccatcagat tgtgtttgtt agtcgct                                          27
```

<210> SEQ ID NO 37
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 37

```
acactgattg acacggttta gtagaac                                          27
```

<210> SEQ ID NO 38
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 38

```
gcttacggtt cactactcac gacgatg                                          27
```

<210> SEQ ID NO 39
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 39

```
gcaatatcag caccaacaga aacaacctt                                        29
```

<210> SEQ ID NO 40
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 40

```
gttctactaa accgtgtcaa tcagtgtc                                         28
```

<210> SEQ ID NO 41
<211> LENGTH: 3560
<212> TYPE: DNA

<213> ORGANISM: Artificial Sequence
<220> FEATURE:
<223> OTHER INFORMATION: Synthetic Polynucleotide

<400> SEQUENCE: 41

```
gcttacggtt cactactcac gacgatgttt tttttggtac cttttttttc accggaaagg      60
acccgtaaag tgataatgat tatcatctac atatcacaac gtgcgtggag gccatcaaac     120
cacgtcaaat aatcaattat gacgcaggta tcgtattaat tgatctgcat caacttaacg     180
taaaaacaac ttcagacaat acaaatcagc gacactgaat acggggcaac ctcatgtcaa     240
cgaagaacag aacccgcaga caacaaccc gcaacatccg ctttcctaac caaatgattg      300
aacaaattaa catcgctctt gagcaaaaag ggtccgggaa tttctcagcc tgggtcattg     360
aagcctgccg tcggagacta acgtcagaaa agagagcata tacatcaatt aaaagtgatg     420
aagaatgaac atcccgcgtt cttccctccg aacaggacga tattgtaaat tcacttaatt     480
acgagggcat tgcagtaatt gagttgcagt tttaccactt tcctgacagt gacagactgc     540
gtgttggctc tgtcacagac taaatagttt gaatgattag cagttatggt gatcagtcaa     600
ccaccaggga ataatccttc atattattat cgtgcttcac caacgctgcc tcaattgctc     660
tgaatgcttc cagagacacc ttatgttcta tacatgcaat tacaacatca gggtaactca     720
tagaaatggt gctattaagc atattttta cacgaatcag atccacggag ggatcatcag      780
cagattgttc tttattcatt ttgtcgctcc atgcgcttgc tcttcatcta gcggttaaaa     840
tattacttca aatctttctg tatgaagatt tgagcacgtt ggccttacat acatctgtcg     900
gttgtatttc cctccagaat gccagcagga ccgcactttg ttacgcaacc aatactatta     960
agtgaaaaca ttcctaatat ttgacataaa tcatcaacaa acacaagga ggtcagacca     1020
gattgaaacg ataaaaacga taatgcaaac tacgcgccct cgtatcacat ggaaggtttt     1080
accaatggct caggttgcca tttttaaaga aatattcgat caagtgcgaa aagatttaga     1140
ctgtgaattg ttttattctg aactaaaacg tcacaacgtc tcacattata tttactatct     1200
agccacagat aatattcaca tcgtgttaga aaacgataac accgtgttaa taaaaggact     1260
taaaaaggtt gtaaatgtta aattctcaag aaacacgcat cttatagaaa cgtcctatga     1320
taggttgaaa tcaagagaaa tcacatttca gcaatacagg gaaaatcttg ctaaagcagg     1380
agttttccga tgggttacaa atatccatga acataaaaga tattactata cctttgataa     1440
ttcattacta tttactgaga gcattcagaa cactacacaa atctttccac gctaaatcat     1500
aacgtccggt ttcttccgtg tcagcaccgg ggcgttggca taatgcaata cgtgtacgcg     1560
ctaaaccctg tgtgcatcgt tttaattatt cccggacact cccgcagaga agttccccgt     1620
cagggctgtg gacatagtta atccgggaat acaatgacga ttcatcgcac ctgacataca     1680
ttaataaata ttaacaatat gaaatttcaa ctcattgttt agggtttgtt taattttcta     1740
cacatacgat tctgcgaact tcaaaaagca tcgggaataa caccatgaaa aaaatgctac     1800
tcgctactgc gctggccctg cttattacag gatgtgctca acagacgttt actgttcaaa     1860
acaaaccggc agcagtagca ccaaaggaaa ccatcaccca tcatttcttc gtttctggaa     1920
ttgggcagaa gaaaactgtc gatgcagcca aatttgtgg cggcgcagaa aatgttgtta     1980
aaacagaaac ccagcaaaca ttcgtaaatg gattgctcgg ttttattact ttaggcattt     2040
atactccgct ggaagcgcgt gtgtattgct cacaataatt gcatgagttg cccatcgata    2100
tgggcaactc tatctgcact gctcattaat atacttctgg gttccttcca gttgtttttg    2160
catagtgatc agcctctctc tgagggtgaa ataatcccgt tcagcggtgt ctgccagtcg    2220
```

-continued

| | |
|---|---|
| gggggaggct gcattatcca cgccggaggc ggtggtggct tcacgcactg actgacagac | 2280 |
| tgctttgatg tgcaaccgac gacgaccagc ggcaacatca tcacgcagag catcattttc | 2340 |
| agctttagca tcagctaact ccttcgtgta ttttgcatcg agcgcagcaa catcacgctg | 2400 |
| acgcatctgc atgtcagtaa ttgccgcgtt cgccagcttc agttctctgg cattttttgtc | 2460 |
| gcgctgggct ttgtaggtaa tggcgttatc acggtaatga ttaacagccc atgacaggca | 2520 |
| gacgatgatg cagataacca gagcggagat aatcgcggtg actctgctca tacatcaatc | 2580 |
| tctctgaccg ttccgcccgc ttctttgaat tttgcaatca ggctgtcagc cttatgctcg | 2640 |
| aactgaccat aaccagcgcc cggcagtgaa gcccagatat tgctgcaacg gtcgattgcc | 2700 |
| tgacggatat caccacgatc aatcataggt aaagcgccac gctccttaat ctgctgcaat | 2760 |
| gccacagcgt cctgactttt cggagagaag tctttcaggc caagctgctt gcggtaggca | 2820 |
| tcccaccaac gggaaagaag ctggtagcgt ccggcgcctg ttgatttgag ttttgggttt | 2880 |
| agcgtgacaa gtttgcgagg gtgatcggag taatcagtaa atagctctcc gcctacaatg | 2940 |
| acgtcataac catgatttct ggttttctga cgtccgttat cagttccctc cgaccacgcc | 3000 |
| agcatatcga ggaacgcctt acgttgatta ttgatttcta ccatcttcta ctccggctttt | 3060 |
| tttagcagcg aagcgtttga taagcgaacc aatcgagtca gtaccgatgt agccgataaa | 3120 |
| cacgctcgtt atataagcga gattgctact tagtccggcg aagtcgagaa ggtcacgaat | 3180 |
| gaactaggcg ataatggcgc acatcgttgc gtcgattact gttttgtaa acgcaccgcc | 3240 |
| attatatctg ccgcgaaggt acgccattgc aaacgcaagg attgcccga tgccttgttc | 3300 |
| cttttgccgcg agaatggcgg ccaacaggtc atgttttttct ggcatcttca tgtcttaccc | 3360 |
| ccaataaggg gatttgctct atttaattag gaataaggtc gattactgat agaacaaatc | 3420 |
| caggctactg tgtttagtaa tcagatttgt tcgtgaccga tatgcacggg caaaacggca | 3480 |
| ggaggttgtt agcgcaaaaa aaaaattcca aaaaaaaat tccaaaaaaa aaaagcgact | 3540 |
| aacaaacaca atctgatggc | 3560 |

<210> SEQ ID NO 42
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 42

| | |
|---|---|
| ttgcaatatc agcaccaaca gaaacaacct t | 31 |

<210> SEQ ID NO 43
<211> LENGTH: 48502
<212> TYPE: DNA
<213> ORGANISM: Artificial Sequence
<220> FEATURE:
<223> OTHER INFORMATION: Synthetic Polynucleotide

<400> SEQUENCE: 43

| | |
|---|---|
| gggcggcgac ctcgcgggtt ttcgctatttt atgaaaattt tccggtttaa ggcgtttccg | 60 |
| ttcttcttcg tcataactta atgttttttat ttaaatacc ctctgaaaag aaaggaaacg | 120 |
| acaggtgctg aaagcgaggc ttttttggcct ctgtcgtttc cttctctgt ttttgtccgt | 180 |
| ggaatgaaca atggaagtca acaaaaagca gctggctgac attttcggtg cgagtatccg | 240 |
| taccattcag aactggcagg aacagggaat gcccgttctg cgaggcggtg gcaagggtaa | 300 |

```
tgaggtgctt tatgactctg ccgccgtcat aaaatggtat gccgaaaggg atgctgaaat    360
tgagaacgaa aagctgcgcc gggaggttga agaactgcgg caggccagcg aggcagatct    420
ccagccagga actattgagt acgaacgcca tcgacttacg cgtgcgcagg ccgacgcaca    480
ggaactgaag aatgccagag actccgctga agtggtggaa accgcattct gtactttcgt    540
gctgtcgcgg atcgcaggtg aaattgccag tattctcgac gggctccccc tgtcggtgca    600
gcggcgtttt ccggaactgg aaaaccgaca tgttgatttc ctgaaacggg atatcatcaa    660
agccatgaac aaagcagccg cgctggatga actgataccg gggttgctga gtgaatatat    720
cgaacagtca ggttaacagg ctgcggcatt ttgtccgcgc cgggcttcgc tcactgttca    780
ggccggagcc acagaccgcc gttgaatggg cggatgctaa ttactatctc ccgaaagaat    840
ccgcatacca ggaagggcgc tgggaaacac tgcccttttca gcgggccatc atgaatgcga    900
tgggcagcga ctacatccgt gaggtgaatg tggtgaagtc tgcccgtgtc ggttattcca    960
aaatgctgct gggtgtttat gcctacttta tagagcataa gcagcgcaac acccttatct   1020
ggttgccgac ggatggtgat gccgagaact ttatgaaaac ccacgttgag ccgactattc   1080
gtgatattcc gtcgctgctg gcgctggccc cgtggtatgg caaaaagcac cgggataaca   1140
cgctcaccat gaagcgtttc actaatgggc gtggcttctg gtgcctgggc ggtaaagcgg   1200
caaaaaacta ccgtgaaaag tcggtggatg tggcgggtta tgatgaactt gctgcttttg   1260
atgatgatat tgaacaggaa ggctctccga cgttcctggg tgacaagcgt attgaaggct   1320
cggtctggcc aaagtccatc cgtggctcca cgccaaaagt gagaggcacc tgtcagattg   1380
agcgtgcagc cagtgaatcc ccgcatttta tgcgttttca tgttgcctgc ccgcattgcg   1440
gggaggagca gtatcttaaa tttggcgaca agagacgcc gtttggcctc aaatggacgc   1500
cggatgaccc ctccagcgtg ttttatctct gcgagcataa tgcctgcgtc atccgccagc   1560
aggagctgga ctttactgat gcccgttata tctgcgaaaa gaccgggatc tggacccgtg   1620
atggcattct ctggttttcg tcatccggtg aagagattga gccacctgac agtgtgacct   1680
ttcacatctg gacagcgtac agcccgttca ccacctgggt gcagattgtc aaagactgga   1740
tgaaaacgaa aggggatacg ggaaaacgta aaaccttcgt aaacaccacg ctcggtgaga   1800
cgtgggaggc gaaaattggc gaacgtccgg atgctgaagt gatggcagag cggaaagagc   1860
attattcagc gcccgttcct gaccgtgtgg cttacctgac cgccggtatc gactcccagc   1920
tggaccgcta cgaaatgcgc gtatggggat ggggccggg tgaggaaagc tggctgattg   1980
accggcagat tattatgggc cgccacgacg atgaacagac gctgctgcgt gtggatgagg   2040
ccatcaataa aacctatacc cgccggaatg gtgcagaaat gtcgatatcc cgtatctgct   2100
gggatactgg cggattgac ccgaccattg tgtatgaacg ctcgaaaaaa catgggctgt   2160
tccgggtgat ccccattaaa ggggcatccg tctacggaaa gccggtggcc agcatgccac   2220
gtaagcgaaa caaaacgggg gtttaccttaa ccgaaatcgg tacgataccg cgaaagagc   2280
agatttataa ccgcttcaca ctgacgccgg aaggggatga accgcttccc ggtgccgttc   2340
acttcccgaa taacccggat attttttgatc tgaccgaagc gcagcagctg actgctgaag   2400
agcaggtcga aaatgggtg gatggcagga aaaaaatact gtgggacagc aaaaagcgac   2460
gcaatgaggc actcgactgc ttcgtttatg cgctggcggc gctgcgcatc agtatttccc   2520
gctggcagct ggatctcagt gcgctgctgg cgagcctgca ggaagaggat ggtgcagcaa   2580
ccaacaagaa aacactggca gattacgccc gtgccttatc cggagaggat gaatgacgcg   2640
acaggaagaa cttgccgctg cccgtgcggc actgcatgac ctgatgacag gtaaacgggt   2700
```

```
ggcaacagta cagaaagacg gacgaagggt ggagtttacg gccacttccg tgtctgacct    2760
gaaaaaatat attgcagagc tggaagtgca gaccggcatg acacagcgac gcagggggacc   2820 tgcaggattt tatgtatgaa aacgcccacc attcccaccc ttctggggcc ggacggcatg    2880
acatcgctgc gcgaatatgc cggttatcac ggcggtggca gcggatttgg agggcagttg    2940
cggtcgtgga acccaccgag tgaaagtgtg gatgcagccc tgttgcccaa ctttacccgt    3000
ggcaatgccc gcgcagacga tctggtacgc aataacggct atgccgccaa cgccatccag    3060
ctgcatcagg atcatatcgt cgggtctttt ttccggctca gtcatcgccc aagctggcgc    3120
tatctgggca tcggggagga agaagcccgt gccttttccc gcgaggttga agcggcatgg    3180
aaagagtttg ccgaggatga ctgctgctgc attgacgttg agcgaaaacg cacgtttacc    3240
atgatgattc gggaaggtgt ggccatgcac gcctttaacg tgaactgtt cgttcaggcc      3300 acctgggata ccagttcgtc gcggcttttc cggacacagt tccggatggt cagcccgaag     3360
cgcatcagca acccgaacaa taccggcgac agccggaact gccgtgccgg tgtgcagatt     3420
aatgacagcg gtgcggcgct gggatattac gtcagcgagg acgggtatcc tggctggatg     3480
ccgcagaaat ggacatggat accccgtgag ttacccggcg ggcgcgcctc gttcattcac     3540 gttttttgaac ccgtggagga cgggcagact cgcggtgcaa atgtgtttta cagcgtgatg   3600
gagcagatga agatgctcga cacgctgcag aacacgcagc tgcagagcgc cattgtgaag    3660
gcgatgtatg ccgccaccat tgagagtgag ctggatacgc agtcagcgat ggatttttatt  3720 ctgggcgcga acagtcagga gcagcgggaa aggctgaccg gctggattgg tgaaattgcc    3780
gcgtattacg ccgcagcgcc ggtccggctg ggaggcgcaa aagtaccgca cctgatgccg    3840
ggtgactcac tgaacctgca gacggctcag gatacggata acggctactc cgtgtttgag    3900
cagtcactgc tgcggtatat cgctgccggg ctgggtgtct cgtatgagca gctttcccgg    3960
aattacgccc agatgagcta ctccacggca cgggccagtg cgaacgagtc gtgggcgtac    4020
tttatggggc ggcgaaaatt cgtcgcatcc cgtcaggcga gccagatgtt tctgtgctgg    4080
ctggaagagg ccatcgttcg ccgcgtggtg acgttaccct caaaaagcgcg cttcagtttt    4140 caggaagccc gcagtgcctg ggggaactgc gactggatag gctccggtcg tatggccatc    4200
gatggtctga agaagttca ggaagcggtg atgctgatag aagccggact gagtacctac     4260
gagaaagagt gcgcaaaacg cggtgacgac tatcaggaaa ttttttgccca gcaggtccgt   4320 gaaacgatgg agcgccgtgc agccggtctt aaaccgcccg cctgggcggc tgcagcattt    4380
gaatccgggc tgcgacaatc aacagaggag gagaagagtg acagcagagc tgcgtaatct    4440
cccgcatatt gccagcatgg cctttaatga gccgctgatg cttgaacccg cctatgcgcg    4500 ggttttctttt tgtgcgcttg caggccagct tgggatcagc agcctgacgg atgcggtgtc    4560
cggcgacagc ctgactgccc aggaggcact cgcgacgctg gcattatccg gtgatgatga    4620
cggaccacga caggcccgca gttatcaggt catgaacggc atcgccgtgc tgccggtgtc     4680
cggcacgctg gtcagccgga cgcgggcgct gcagccgtac tcggggatga ccggttacaa    4740
cggcattatc gcccgtctgc aacaggctgc cagcgatccg atggtggacg gcattctgct    4800
cgatatggac acgcccggcg ggatggtggc ggggcatttt gactgcgctg acatcatcgc    4860
ccgtgtgcgt gacataaaac cggtatgggc gcttgccaac gacatgaact gcagtgcagg    4920
tcagttgctt gccagtgccg cctcccggcg tctggtcacg cagaccgccc ggacaggctc    4980
catcggcgtc atgatggctc acagtaatta cggtgctgcg ctggagaaac agggtgtgga    5040
```

```
aatcacgctg atttacagcg gcagccataa ggtggatggc aaccccctaca gccatcttcc   5100
ggatgacgtc cgggagacac tgcagtcccg gatggacgca acccgccaga tgtttgcgca   5160
gaaggtgtcg gcatataccg gcctgtccgt gcaggttgtg ctggataccg aggctgcagt   5220
gtacagcggt caggaggcca ttgatgccgg actggctgat gaacttgtta acagcaccga   5280
tgcgatcacc gtcatgcgtg atgcactgga tgcacgtaaa tcccgtctct caggagggcg   5340
aatgaccaaa gagactcaat caacaactgt ttcagccact gcttcgcagg ctgacgttac   5400
tgacgtggtg ccagcgacgg agggcgagaa cgccagcgcg gcgcagccgg acgtgaacgc   5460
gcagatcacc gcagcggttg cggcagaaaa cagccgcatt atggggatcc tcaactgtga   5520
ggaggctcac ggacgcgaag aacaggcacg cgtgctggca gaaaccccg  gtatgaccgt   5580
gaaaacggcc cgccgcattc tggccgcagc accacagagt gcacaggcgc gcagtgacac   5640
tgcgctggat cgtctgatgc aggggcacc  ggcaccgctg gctgcaggta  acccggcatc   5700
tgatgccgtt aacgatttgc tgaacacacc agtgtaaggg atgtttatga  cgagcaaaga   5760
aaccttttacc cattaccagc cgcagggcaa cagtgacccg gctcataccg caaccgcgcc   5820
cggcggattg agtgcgaaag cgcctgcaat gaccccgctg atgctggaca cctccagccg   5880
taagctggtt gcgtgggatg gcaccaccga cggtgctgcc gttggcattc ttgcggttgc   5940
tgctgaccag accagcacca cgctgacgtt ctacaagtcc ggcacgttcc gttatgagga   6000
tgtgctctgg ccgaggctg  ccagcgacga gacgaaaaaa cggaccgcgt  ttgccggaac   6060
ggcaatcagc atcgtttaac tttacccttc atcactaaag gccgcctgtg cggctttttt   6120
tacgggattt ttttatgtcg atgtacacaa ccgcccaact gctggcggca aatgagcaga   6180
aatttaagtt tgatccgctg tttctgcgtc tcttttttccg tgagagctat cccttcacca   6240
cggagaaagt ctatctctca caaattccgg gactggtaaa catggcgctg tacgtttcgc   6300
cgattgtttc cggtgaggtt atccgttccc gtggcggctc cacctctgaa tttacgccgg   6360
gatatgtcaa gccgaagcat gaagtgaatc cgcagatgac cctgcgtcgc ctgccggatg   6420
aagatccgca gaatctggcg gacccggctt accgccgccg tcgcatcatc atgcagaaca   6480
tgcgtgacga agagctggcc attgctcagg tcgaagagat gcaggcagtt tctgccgtgc   6540
ttaagggcaa atacaccatg accggtgaag ccttcgatcc ggttgaggtg gatatgggcc   6600
gcagtgagga gaataacatc acgcagtccg gcggcacgga gtggagcaag cgtgacaagt   6660
ccacgtatga cccgaccgac gatatcgaag cctacgcgct gaacgccagc ggtgtggtga   6720
atatcatcgt gttcgatccg aaaggctggg cgctgttccg ttccttcaaa gccgtcaagg   6780
agaagctgga tacccgtcgt ggctctaatt ccgagctgga gacagcggtg aaagacctgg   6840
gcaaagcggt gtcctataag gggatgtatg gcgatgtggc catcgtcgtg tattccggac   6900
agtacgtgga aaacggcgtc aaaaagaact tcctgccgga caacacgatg gtgctgggga   6960
acactcaggc acgcggtctg cgcacctatg gctgcattca ggatgcggac gcacagcgcg   7020
aaggcattaa cgcctctgcc cgttacccga aaaactgggt gaccaccggc gatccggcgc   7080
gtgagttcac catgattcag tcagcaccgc tgatgctgct ggctgaccct gatgagttcg   7140
tgtccgtaca actggcgtaa tcatggccct tcggggccat tgtttctctg tggaggagtc   7200
catgacgaaa gatgaactga ttgcccgtct ccgctcgctg ggtgaacaac tgaaccgtga   7260
tgtcagcctg acggggacga agaagaact  ggcgctccgt gtggcagagc tgaaagagga   7320
gcttgatgac acggatgaaa ctgccggtca ggacacccct ctcagcccgg aaaatgtgct   7380
gaccggacat gaaaatgagg tgggatcagc gcagccggat accgtgattc tggatacgtc   7440
```

```
tgaactggtc acggtcgtgg cactggtgaa gctgcatact gatgcacttc acgccacgcg   7500
ggatgaacct gtggcatttg tgctgccggg aacggcgttt cgtgtctctg ccggtgtggc   7560
agccgaaatg acagagcgcg gcctggccag aatgcaataa cgggaggcgc tgtggctgat   7620
ttcgataacc tgttcgatgc tgccattgcc cgcgccgatg aaacgatacg cgggtacatg   7680
ggaacgtcag ccaccattac atccggtgag cagtcaggtg cggtgatacg tggtgttttt   7740
gatgaccctg aaaatatcag ctatgccgga cagggcgtgc gcgttgaagg ctccagcccg   7800
tccctgtttg tccggactga tgaggtgcgg cagctgcggc gtggagacac gctgaccatc   7860
ggtgaggaaa atttctgggt agatcgggtt tcgccggatg atggcggaag ttgtcatctc   7920
tggcttggac ggggcgtacc gcctgccgtt aaccgtcgcc gctgaaaggg ggatgtatgg   7980
ccataaaagg tcttgagcag gccgttgaaa acctcagccg tatcagcaaa acggcggtgc   8040
ctggtgccgc cgcaatggcc attaaccgcg ttgcttcatc cgcgatatcg cagtcggcgt   8100
cacaggttgc ccgtgagaca aaggtacgcc ggaaactggt aaaggaaagg ccaggctga   8160 aaagggccac ggtcaaaaat ccgcaggcca gaatcaaagt taaccggggg gatttgcccg   8220
taatcaagct gggtaatgcg cgggttgtcc tttcgcgccg caggcgtcgt aaaaaggggc   8280
agcgttcatc cctgaaaggt ggcggcagcg tgcttgtggt gggtaaccgt cgtattcccg   8340
gcgcgtttat tcagcaactg aaaaatggcc ggtggcatgt catgcagcgt gtggctggga   8400
aaaaccgtta ccccattgat gtggtgaaaa tcccgatggc ggtgccgctg accacggcgt   8460
ttaaacaaaa tattgagcgg atacggcgtg aacgtcttcc gaaagagctg gctatgcgc   8520 tgcagcatca actgaggatg gtaataaagc gatgaaacat actgaactcc gtgcagccgt   8580
actggatgca ctggagaagc atgacaccgg ggcgacgttt tttgatggtc gccccgctgt   8640
ttttgatgag gcggattttc cggcagttgc cgtttatctc accggcgctg aatacacggg   8700
cgaagagctg gacagcgata cctggcaggc ggagctgcat atcgaagttt tcctgcctgc   8760
tcaggtgccg gattcagagc tggatgcgtg gatgagtcc cggatttatc cggtgatgag   8820
cgatatcccg gcactgtcag atttgatcac cagtatggtg ccagcggct atgactaccg   8880 gcgcgacgat gatgcgggct tgtggagttc agccgatctg acttatgtca ttacctatga   8940
aatgtgagga cgctatgcct gtaccaaatc ctacaatgcc ggtgaaaggt gccgggacca   9000
ccctgtgggt ttataagggg agcggtgacc cttacgcgaa tccgctttca gacgttgact   9060
ggtcgcgtct ggcaaaagtt aaagacctga cgcccggcga actgaccgct gagtcctatg   9120
acgacagcta tctcgatgat gaagatgcag actggactgc gaccgggcag gggcagaaat   9180
ctgccggaga taccagcttc acgctggcgt ggatgcccgg agagcagggg cagcaggcgc   9240
tgctggcgtg gttaatgaa ggcgataccc gtgcctataa aatccgcttc ccgaacggca   9300
cggtcgatgt gttccgtggc tgggtcagca gtatcggtaa ggcggtgacg gcgaaggaag   9360
tgatcacccg cacggtgaaa gtcaccaatg tgggacgtcc gtcgatggca gaagatcgca   9420
gcacggtaac agcggcaacc ggcatgaccg tgacgcctgc cagcacctcg gtggtgaaag   9480
ggcagagcac cacgctgacc gtggccttcc agccggaggg cgtaaccgac aagagctttc   9540
gtgcggtgtc tgcggataaa acaaaagcca ccgtgtcggt cagtggtatg accatcaccg   9600
tgaacggcgt tgctgcaggc aaggtcaaca ttccggttgt atccggtaat ggtgagtttg   9660
ctgcggttgc agaaattacc gtcaccgcca gttaatccgg agagtcagcg atgttcctga   9720
aaaccgaatc atttgaacat aacggtgtga ccgtcacgct ttctgaactg tcagccctgc   9780
```

```
agcgcattga gcatctcgcc ctgatgaaac ggcaggcaga acaggcggag tcagacagca    9840
accggaagtt tactgtggaa gacgccatca gaaccggcgc gtttctggtg gcgatgtccc    9900
tgtggcataa ccatccgcag aagacgcaga tgccgtccat gaatgaagcc gttaaacaga    9960
ttgagcagga agtgcttacc acctggccca cggaggcaat ttctcatgct gaaaacgtgg   10020
tgtaccggct gtctggtatg tatgagtttg tggtgaataa tgcccctgaa cagacagagg   10080
acgccgggcc cgcagagcct gtttctgcgg gaaagtgttc gacggtgagc tgagttttgc   10140
cctgaaactg gcgcgtgaga tggggcgacc cgactggcgt gccatgcttg ccgggatgtc   10200
atccacggag tatgccgact ggcaccgctt ttacagtacc cattattttc atgatgttct   10260
gctggatatg cacttttccg ggctgacgta caccgtgctc agcctgtttt tcagcgatcc   10320
ggatatgcat ccgctggatt tcagtctgct gaaccggcgc gaggctgacg aagagcctga   10380
agatgatgtg ctgatgcaga aagcggcagg gcttgccgga ggtgtccgct ttggcccgga   10440
cgggaatgaa gttatccccg cttccccgga tgtggcggac atgacggagg atgacgtaat   10500
gctgatgaca gtatcagaag ggatcgcagg aggagtccgg tatggctgaa ccggtaggcg   10560
atctggtcgt tgatttgagt ctggatgcgg ccagatttga cgagcagatg ccagagtca   10620 ggcgtcattt ttctggtacg gaaagtgatg cgaaaaaaac agcggcagtc gttgaacagt   10680
cgctgagccg acaggcgctg gctgcacaga aagcggggat ttccgtcggg cagtataaag   10740
ccgccatgcg tatgctgcct gcacagttca ccgacgtggc cacgcagctt gcaggcgggc   10800
aaagtccgtg gctgatcctg ctgcaacagg gggggcaggt gaaggactcc ttcggcggga   10860
tgatccccat gttcagggg cttgccggtg cgatcaccct gccgatggtg ggggccacct   10920
cgctggcggt ggcgaccggt gcgctggcgt atgcctggta tcagggcaac tcaaccctgt   10980
ccgatttcaa caaaacgctg gtcctttccg gcaatcaggc gggactgacg gcagatcgta   11040
tgctggtcct gtccagagcc gggcaggcgg cagggctgac gtttaaccag accagcgagt   11100
cactcagcgc actggttaag gcgggggtaa gcggtgaggc tcagattgcg tccatcagcc   11160
agagtgtggc gcgtttctcc tctgcatccg gcgtggaggt ggacaaggtc gctgaagcct   11220
tcgggaagct gaccacagac ccgacgtcgg ggctgacggc gatggctcgc cagttccata   11280
acgtgtcggc ggagcagatt gcgtatgttg ctcagttgca gcgttccggc gatgaagccg   11340
gggcattgca ggcggcgaac gaggccgcaa cgaaagggtt tgatgaccag acccgccgcc   11400
tgaaagagaa catgggcacg ctggagacct gggcagacag gactgcgcgg gcattcaaat   11460
ccatgtggga tgcggtgctg gatattggtc gtcctgatac cgcgcaggag atgctgatta   11520
aggcagaggc tgcgtataag aaagcagacg acatctggaa tctgcgcaag gatgattatt   11580
ttgttaacga tgaagcgcgg gcgcgttact gggatgatcg tgaaaaggcc cgtcttgcgc   11640
ttgaagccgc ccgaaagaag gctgagcagc agactcaaca ggacaaaaat gcgcagcagc   11700
agagcgatac cgaagcgtca cggctgaaat ataccgaaga ggcgcagaag gcttacgaac   11760
ggctgcagac gccgctggag aaatataccg cccgtcagga agaactgaac aaggcactga   11820
aagacgggaa aatcctgcag gcggattaca acacgctgat ggcggcggcg aaaaaggatt   11880
atgaagcgac gctgaaaaag ccgaaacagt ccagcgtgaa ggtgtctgcg ggcgatcgtc   11940
aggaagacag tgctcatgct gccctgctga cgcttcaggc agaactccgg acgctggaga   12000
agcatgccgg agcaaatgag aaaatcagcc agcagcgccg ggatttgtgg aaggcggaga   12060
gtcagttcgc ggtactggag gaggcggcgc aacgtcgcca gctgtctgca caggagaaat   12120
ccctgctggc gcataaagat gagacgctgg agtacaaacg ccagctggct gcacttggcg   12180
```

```
acaaggttac gtatcaggag cgcctgaacg cgctggcgca gcaggcggat aaattcgcac   12240
agcagcaacg ggcaaaacgg gccgccattg atgcgaaaag ccgggggctg actgaccggc   12300
aggcagaacg ggaagccacg gaacagcgcc tgaaggaaca gtatggcgat aatccgctgg   12360
cgctgaataa cgtcatgtca gagcagaaaa agacctgggc ggctgaagac cagcttcgcg   12420
ggaactggat ggcaggcctg aagtccggct ggagtgagtg gaagagagc gccacggaca    12480 gtatgtcgca ggtaaaaagt gcagccacgc agacctttga tggtattgca cagaatatgg   12540
cggcgatgct gaccggcagt gagcagaact ggcgcagctt cacccgttcc gtgctgtcca   12600
tgatgacaga aattctgctt aagcaggcaa tggtggggat tgtcgggagt atcggcagcg   12660
ccattggcgg ggctgttggt ggcggcgcat ccgcgtcagg cggtacagcc attcaggccg   12720
ctgcggcgaa attccatttt gcaaccggag gatttacggg aaccggcggc aaatatgagc   12780
cagcggggat tgttcaccgt ggtgagtttg tcttcacgaa ggaggcaacc agccggattg   12840
gcgtggggaa tctttaccgg ctgatgcgcg gctatgccac cggcggttat gtcggtacac   12900
cgggcagcat ggcagacagc cggtcgcagg cgtccgggac gtttgagcag aataaccatg   12960
tggtgattaa caacgacggc acgaacgggc agataggtcc ggctgctctg aaggcggtgt   13020
atgacatggc ccgcaagggt gcccgtgatg aaattcagac acagatgcgt gatggtggcc   13080
tgttctccgg aggtgacga tgaagaccct ccgctgaaa gtgaacccg gtatggatgt     13140 ggcttcggtc ccttctgtaa gaaaggtgcg ctttggtgat ggctattctc agcgagcgcc   13200
tgccgggctg aatgccaacc tgaaaacgta cagcgtgacg cttctgtcc cccgtgagga    13260 ggccacggta ctggagtcgt ttctggaaga gcacggggc tggaaatcct ttctgtggac    13320
gccgccttat gagtggcggc agataaaggt gacctgcgca aaatggtcgt cgcgggtcag   13380
tatgctgcgt gttgagttca gcgcagagtt tgaacaggtg gtgaactgat gcaggatatc   13440
cggcaggaaa cactgaatga atgcacccgt gcggagcagt cggccagcgt ggtgctctgg   13500
gaaatcgacc tgacagaggt cggtggagaa cgttattttt tctgtaatga gcagaacgaa   13560
aaaggtgagc cggtcacctg gcaggggcga cagtatcagc cgtatcccat tcaggggagc   13620
ggttttgaac tgaatggcaa aggcaccagt acgcgcccca cgctgacggt ttctaacctg   13680
tacggtatgg tcaccgggat ggcggaagat atgcagagtc tggtcggcgg aacggtggtc   13740
cggcgtaagg tttacgcccg ttttctggat gcggtgaact tcgtcaacgg aaacagttac   13800
gccgatccgg agcaggaggt gatcagccgc tggcgcattg agcagtgcag cgaactgagc   13860
gcggtgagtg cctcctttgt actgtccacg ccgacggaaa cggatggcgc tgttttttccg   13920 ggacgtatca tgctggccaa cacctgcacc tggacctatc gcggtgacga gtgcggttat   13980
agcggtccgg ctgtcgcgga tgaatatgac cagccaacgt ccgatatcac gaaggataaa   14040
tgcagcaaat gcctgagcgg ttgtaagttc cgcaataacg tcggcaactt tggcggcttc   14100 cttttccatta acaaactttc gcagtaaatc ccatgacaca gacagaatca gcgattctgg   14160
cgcacgcccg gcgatgtgcg ccagcggagt cgtgcggctt cgtggtaagc acgccggagg   14220
gggaaagata tttcccctgc gtgaatatct ccggtgagcc ggaggctatt tccgtatgtc   14280 gccgaagac tggctgcagg cagaaatgca gggtgagatt gtggcgctgg tccacagcca    14340
ccccggtggt ctgccctggc tgagtgaggc cgaccggcgg ctgcaggtgc agagtgattt   14400
gccgtggtgg ctggtctgcc gggggacgat tcataagttc cgctgtgtgc cgcatctcac   14460
cgggcggcgc tttgagcacg gtgtgacgga ctgttacaca ctgttccggg atgcttatca   14520
```

```
tctggcgggg attgagatgc cggactttca tcgtgaggat gactggtggc gtaacggcca    14580
gaatctctat ctggataatc tggaggcgac ggggctgtat caggtgccgt tgtcagcggc    14640
acagccgggc gatgtgctgc tgtgctgttt tggttcatca gtgccgaatc acgccgcaat    14700
ttactgcggc gacggcgagc tgctgcacca tattcctgaa caactgagca acgagagag    14760 gtacaccgac aaatggcagc gacgcacaca ctccctctgg cgtcaccggg catggcgcgc    14820
atctgccttt acggggattt acaacgattt ggtcgccgca tcgaccttcg tgtgaaaacg    14880
ggggctgaag ccatccgggc actggccaca cagctcccgg cgtttcgtca gaaactgagc    14940
gacggctggt atcaggtacg gattgccggg cgggacgtca gcacgtccgg gttaacggcg    15000
cagttacatg agactctgcc tgatggcgct gtaattcata ttgttcccag agtcgccggg    15060
gccaagtcag gtggcgtatt ccagattgtc ctgggggctg ccgccattgc cggatcattc    15120
tttaccgccg gagccaccct tgcagcatgg ggggcagcca ttggggccgg tggtatgacc    15180
ggcatcctgt tttctctcgg tgccagtatg gtgctcggtg gtgtggcgca gatgctggca    15240
ccgaaagcca gaactccccg tatacagaca acgataacg taagcagaa cacctatttc    15300 tcctcactgg ataacatggt tgcccagggc aatgttctgc ctgttctgta cggggaaatg    15360 ccgcgtggggt cacgcgtggt ttctcaggag atcagcacgg cagacgaagg ggacggtggt    15420
caggttgtgg tgattggtcg ctgatgcaaa atgttttatg tgaaaccgcc tgcgggcggt    15480
tttgtcattt atggagcgtg aggaatgggt aaggaagca gtaaggggca taccccgcgc    15540
gaagcgaagg acaacctgaa gtccacgcag ttgctgagtg tgatcgatgc catcagcgaa    15600
gggccgattg aaggtccggt ggatggctta aaaagcgtgc tgctgaacag tacgccggtg    15660
ctggacactg aggggaatac caacatatcc ggtgtcacgg tggtgttccg ggctggtgag    15720
caggagcaga ctccgccgga gggatttgaa tcctccggct ccgagacggt gctgggtacg    15780
gaagtgaaat atgacacgcc gatcacccgc accattacgt ctgcaaacat cgaccgtctg    15840
cgctttacct tcggtgtaca ggcactggtg gaaaccacct caaagggtga caggaatccg    15900
tcggaagtcc gcctgctggt tcagatacaa cgtaacggtg gctgggtgac ggaaaaagac    15960
atcaccatta agggcaaaac cacctcgcag tatctggcct cggtggtgat gggtaacctg    16020
ccgccgcgcc cgtttaatat ccggatgcgc aggatgacgc cggacagcac cacagaccag    16080
ctgcagaaca aaacgctctg gtcgtcatac actgaaatca tcgatgtgaa acagtgctac    16140
ccgaacacgg cactggtcgg cgtgcaggtg gactcggagc agttcggcag ccagcaggtg    16200
agccgtaatt atcatctgcg cgggcgtatt ctgcaggtgc cgtcgaacta taaccccgcag    16260 acgcggcaat acagcggtat ctgggacgga acgtttaaac cggcatacag caacaacatg    16320
gcctggtgtc tgtgggatat gctgacccat ccgcgctacg gcatgggaa acgtcttggt    16380 gcggcggatg tggataaatg ggcgctgtat gtcatcggcc agtactgcga ccagtcagtg    16440
ccggacggct ttggcggcac ggagccgcgc atcacctgta atgcgtacct gaccacacag    16500
cgtaaggcgt gggatgtgct cagcgatttc tgctcggcga tgcgctgtat gccggtatgg    16560
aacgggcaga cgctgacgtt cgtgcaggac cgaccgtcgg ataagacgtg gacctataac    16620
cgcagtaatg tggtgatgcc ggatgatggc gcgccgttcc gctacagctt cagcgccctg    16680
aaggaccgcc ataatgccgt tgaggtgaac tggattgacc cgaacaacgg ctgggagacg    16740
gcgacagagc ttgttgaaga tacgcaggcc attgcccgtt acggtcgtaa tgttacgaag    16800
atggatgcct ttggctgtac cagccgggggg caggcacacc gcgccgggct gtggctgatt    16860
aaaacagaac tgctggaaac gcagaccgtg gatttcagcg tcggcgcaga agggcttcgc    16920
```

```
catgtaccgg gcgatgttat tgaaatctgc gatgatgact atgccggtat cagcaccggt  16980
ggtcgtgtgc tggcggtgaa cagccagacc cggacgctga cgctcgaccg tgaaatcacg  17040
ctgccatcct ccggtaccgc gctgataagc ctggttgacg aagtggcaa tccggtcagc   17100 gtggaggttc agtccgtcac cgacggcgtg aaggtaaaag tgagccgtgt tcctgacggt  17160
gttgctgaat acagcgtatg ggagctgaag ctgccgacgc tgcgccagcg actgttccgc  17220
tgcgtgagta tccgtgagaa cgacgacggc acgtatgcca tcaccgccgt gcagcatgtg  17280
ccggaaaaag aggccatcgt ggataacggg cgcactttg acggcgaaca gagtggcacg    17340
gtgaatggtg tcacgccgcc agcggtgcag caccctgaccg cagaagtcac tgcagacagc  17400
ggggaatatc aggtgctggc gcgatgggac acaccgaagg tggtgaaggg cgtgagtttc  17460
ctgctccgtc tgaccgtaac agcggacgac ggcagtgagc ggctggtcag cacggcccgg  17520
acgacggaaa ccacataccg cttcacgcaa ctggcgctgg gaactacag gctgacagtc    17580 cgggcggtaa atgcgtgggg gcagcagggc gatccggcgt cggtatcgtt ccggattgcc  17640
gcaccggcag caccgtcgag gattgagctg acgccgggct attttcagat aaccgccacg  17700
ccgcatcttg ccgtttatga cccgacggta cagtttgagt tctggttctc ggaaaagcag  17760
attgcggata tcagacaggt tgaaaccagc acgcgttatc ttggtacggc gctgtactgg  17820
atagccgcca gtatcaatat caaaccgggc catgattatt acttttatat ccgcagtgtg  17880
aacaccgttg gcaaatcggc attcgtggag gccgtcggtc gggcgagcga tgatgcggaa  17940
ggttacctgg atttttttcaa aggcaagata accgaatccc atctcggcaa ggagctgctg  18000 gaaaagtcg agctgacgga ggataacgcc agcagactgg aggagttttc gaaagagtgg   18060
aaggatgcca gtgataagtg gaatgccatg tgggctgtca aaattgagca gaccaaagac  18120
ggcaaacatt atgtcgcggg tattggcctc agcatggagg acacggagga aggcaaactg  18180
agccagtttc tggttgccgc caatcgtatc gcatttattg acccggcaaa cgggaatgaa  18240
acgccgatgt ttgtggcgca gggcaaccag atattcatga acgacgtgtt cctgaagcgc  18300
ctgacggccc ccaccattac cagcggcggc aatcctccgg ccttttccct gacaccggac  18360
ggaaagctga ccgctaaaaa tgcggatatc agtggcagtg tgaatgcgaa ctccgggacg  18420
ctcagtaatg tgacgatagc tgaaaactgt acgataaacg gtacgctgag ggcggaaaaa  18480
atcgtcgggg acattgtaaa ggcggcgagc gcggcttttc cgcgccagcg tgaaagcagt  18540
gtggactggc cgtcaggtac ccgtactgtc accgtgaccg atgaccatcc ttttgatcgc  18600
cagatagtgg tgcttccgct gacgtttcgc ggaagtaagc gtactgtcag cggcaggaca  18660
acgtattcga tgtgttatct gaaagtactg atgaacggtg cggtgattta tgatggcgcg  18720
gcgaacgagg cggtacaggt gttctcccgt attgttgaca tgccagcggg tcggggaaac  18780
gtgatcctga cgttcacgct tacgtccaca cggcattcgg cagatattcc gccgtatacg  18840
tttgccagcg atgtgcaggt tatggtgatt aagaaacagg cgctgggcat cagcgtggtc  18900
tgagtgtgtt acagaggttc gtccgggaac gggcgtttta ttataaaaca gtgagaggtg  18960
aacgatgcgt aatgtgtgta ttgccgttgc tgtctttgcc gcacttgcgg tgacagtcac  19020
tccgccccgt gcggaaggtg gacatggtac gtttacggtg ggctattttc aagtgaaacc  19080
gggtacattg ccgtcgttgt cgggcgggga taccggtgtg agtcatctga aagggattaa  19140
cgtgaagtac cgttatgagc tgacggacag tgtggggtg atggcttccc tggggttcgc    19200
cgcgtcgaaa aagagcagca cagtgatgac cggggaggat acgtttcact atgagagcct  19260
```

```
gcgtggacgt tatgtgagcg tgatggccgg accggtttta caaatcagta agcaggtcag   19320
tgcgtacgcc atggccggag tggctcacag tcggtggtcc ggcagtacaa tggattaccg   19380
taagacggaa atcactcccg ggtatatgaa agagacgacc actgccaggg acgaaagtgc   19440
aatgcggcat acctcagtgg cgtggagtgc aggtatacag attaatccgg cagcgtccgt   19500
cgttgttgat attgcttatg aaggctccgg cagtggcgac tggcgtactg acggattcat   19560
cgttggggtc ggttataaat tctgattagc caggtaacac agtgttatga cagcccgccg   19620
gaaccggtgg gctttttttgt ggggtgaata tggcagtaaa gatttcagga gtcctgaaag   19680
acggcacagg aaaaccggta cagaactgca ccattcagct gaaagccaga cgtaacagca   19740
ccacggtggt ggtgaacacg gtgggctcag agaatccgga tgaagccggg cgttacagca   19800
tggatgtgga gtacggtcag tacagtgtca tcctgcaggt tgacggtttt ccaccatcgc   19860
acgccgggac catcaccgtg tatgaagatt cacaaccggg gacgctgaat gattttctct   19920
gtgccatgac ggaggatgat gcccggccgg aggtgctgcg tcgtcttgaa ctgatggtgg   19980
aagaggtggc gcgtaacgcg tccgtggtgg cacagagtac ggcagacgcg aagaaatcag   20040
ccggcgatgc cagtgcatca gctgctcagg tcgcggccct tgtgactgat gcaactgact   20100
cagcacgcgc cgccagcacg tccgccggac aggctgcatc gtcagctcag gaagcgtcct   20160
ccggcgcaga agcggcatca gcaaaggcca ctgaagcgga aaaaagtgcc gcagccgcag   20220
agtcctcaaa aaacgcggcg gccaccagtg ccggtgcggc gaaaacgtca gaaacgaatg   20280
ctgcagcgtc acaacaatca gccgccacgt ctgcctccac cgcggccacg aaagcgtcag   20340
aggccgccac ttcagcacga gatgcggtgg cctcaaaaga ggcagcaaaa tcatcagaaa   20400
cgaacgcatc atcaagtgcc ggtcgtgcag cttcctcggc aacggcggca gaaaattctg   20460
ccagggcggg aaaaacgtcc gagacgaatg ccaggtcatc tgaaacagca gcggaacgga   20520
gcgcctctgc cgcggcagac gcaaaaacag cggcggcggg gagtgcgtca acggcatcca   20580
cgaaggcgag agaggctgcg ggaagtgcgg tatcagcatc gcagagcaaa agtgcggcag   20640
aagcggcggc aatacgtgca aaaaattcgg caaaacgtgc agaagatata gcttcagctg   20700
tcgcgcttga ggatgcggac acaacgagaa agggggatagt gcagctcagc agtgcaacca   20760
acagcacgtc tgaaacgctt gctgcaacgc caaaggcggt taaggtggta atggatgaaa   20820
cgaacagaaa agcccactgg acagtccggc actgaccgga acgccaacag caccaaccgc   20880
gctcagggga acaaacaata cccagattgc gaacaccgct tttgtactgg ccgcgattgc   20940
agatgttatc gacgcgtcac ctgacgcact gaatacgctg aatgaactgg ccgcagcgct   21000
cgggaatgat ccagattttg ctaccaccat gactaacgcg cttgcgggta acaaccgaa   21060 gaatgcgaca ctgacggcgc tggcagggct ttccacggcg aaaataaat taccgtattt   21120 tgcggaaaat gatgccgcca gcctgactga actgactcag gttggcaggg atattctggc   21180
aaaaaattcc gttgcagatg ttcttgaata ccttggggcc ggtgagaatt cggccttttcc   21240 ggcaggtgcg ccgatcccgt ggccatcaga tatcgttccg tctggctacg tcctgatgca   21300
ggggcaggcg tttgacaaat cagcctaccc aaaacttgct gtcgcgtatc catcgggtgt   21360
gcttcctgat atgcgaggct ggacaatcaa ggggaaaccc gccagcggtc gtgctgtatt   21420
gtctcaggaa caggatggaa ttaagtcgca cacccacagt gccagtgcat ccggtacgga   21480
tttggggacg aaaaccacat cgtcgtttga ttacgggacg aaaacaacag gcagtttcga   21540
ttacggcacc aaatcgacga ataacacggg ggctcatgct cacagtctga gcggttcaac   21600
aggggccgcg ggtgctcatg cccacacaag tggtttaagg atgaacagtt ctggctggag   21660
```

```
tcagtatgga acagcaacca ttacaggaag tttatccaca gttaaaggaa ccagcacaca  21720
gggtattgct tatttatcga aaacggacag tcagggcagc cacagtcact cattgtccgg  21780
tacagccgtg agtgccggtg cacatgcgca tacagttggt attggtgcgc accagcatcc  21840
ggttgttatc ggtgctcatg cccattcttt cagtattggt tcacacggac acaccatcac  21900
cgttaacgct gcgggtaacg cggaaaacac cgtcaaaaac attgcattta actatattgt  21960
gaggcttgca taatggcatt cagaatgagt gaacaaccac ggaccataaa aatttataat  22020
ctgctggccg gaactaatga atttattggt gaaggtgacg catatattcc gcctcatacc  22080
ggtctgcctg caaacagtac cgatattgca ccgccagata ttccggctgg ctttgtggct  22140
gttttcaaca gtgatgaggc atcgtggcat ctcgttgaag accatcgggg taaaaccgtc  22200
tatgacgtgg cttccggcga cgcgttattt atttctgaac tcggtccgtt accggaaaat  22260
tttacctggt tatcgccggg aggggaatat cagaagtgga acggcacagc ctgggtgaag  22320
gatacggaag cagaaaaact gttccggatc cgggaggcgg aagaaacaaa aaaaagcctg  22380
atgcaggtag ccagtgagca tattgcgccg cttcaggatg ctgcagatct ggaaattgca  22440
acgaaggaag aaacctcgtt gctggaagcc tggaagaagt atcgggtgtt gctgaaccgt  22500
gttgatacat caactgcacc tgatattgag tggcctgctg tccctgttat ggagtaatcg  22560
ttttgtgata tgccgcagaa acgttgtatg aaataacgtt ctgcggttag ttagtatatt  22620
gtaaagctga gtattggttt atttggcgat tattatcttc aggagaataa tggaagttct  22680
atgactcaat tgttcatagt gtttacatca ccgccaattg cttttaagac tgaacgcatg  22740
aaatatggtt tttcgtcatg ttttgagtct gctgttgata tttctaaagt cggttttttt  22800
tcttcgtttt ctctaactat tttccatgaa atacattttt gattattatt tgaatcaatt  22860
ccaattacct gaagtctttc atctataatt ggcattgtat gtattggttt attggagtag  22920
atgcttgctt ttctgagcca tagctctgat atccaaatga agccataggc atttgttatt  22980
ttggctctgt cagctgcata acgccaaaaa atatatttat ctgcttgatc ttcaaatgtt  23040
gtattgatta aatcaattgg atggaattgt ttatcataaa aaattaatgt ttgaatgtga  23100
taaccgtcct ttaaaaaagt cgtttctgca agcttggctg tatagtcaac taactcttct  23160
gtcgaagtga tattttttagg cttatctacc agttttagac gctctttaat atcttcagga  23220
attattttat tgtcatattg tatcatgcta aatgacaatt tgcttatgga gtaatctttt  23280 aatttttaaat aagttattct cctggcttca tcaaataaag agtcgaatga tgttggcgaa  23340
atcacatcgt cacccattgg attgtttatt tgtatgccaa gagagttaca gcagttatac  23400
attctgccat agattatagc taaggcatgt ataattcgt aatcttttag cgtattagcg  23460
acccatcgtc tttctgattt aataatagat gattcagtta aatatgaagg taatttcttt  23520
tgtgcaagtc tgactaactt ttttatacca atgtttaaca tactttcatt tgtaataaac  23580
tcaatgtcat tttcttcaat gtaagatgaa ataagagtag cctttgcctc gctatacatt  23640
tctaaatcgc cttgtttttc tatcgtattg cgagaatttt tagcccaagc cattaatgga  23700 tcattttttcc atttttcaat aacattattg ttataccaaa tgtcatatcc tataatctgg  23760
ttttgttttt tttgaataat aaatgttact gttcttgcgg tttggaggaa ttgattcaaa  23820
ttcaagcgaa ataattcagg gtcaaaatat gtatcaatgc agcatttgag caagtgcgat  23880 aaatcttttaa gtcttctttc ccatggtttt ttagtcataa aactctccat tttgataggt  23940
tgcatgctag atgctgatat attttagagg tgataaaatt aactgcttaa ctgtcaatgt  24000
```

```
aatacaagtt gtttgatctt tgcaatgatt cttatcagaa accatatagt aaattagtta    24060
cacaggaaat ttttaatatt attattatca ttcattatgt attaaaatta gagttgtggc    24120
ttggctctgc taacacgttg ctcataggag atatggtaga gccgcagaca cgtcgtatgc    24180
aggaacgtgc tgcggctggc tggtgaactt ccgatagtgc gggtgttgaa tgatttccag    24240
ttgctaccga ttttacatat tttttgcatg agagaatttg taccacctcc caccgaccat    24300
ctatgactgt acgccactgt ccctaggact gctatgtgcc ggagcggaca ttacaaacgt    24360
ccttctcggt gcatgccact gttgccaatg acctgcctag gaattggtta gcaagttact    24420
accggatttt gtaaaaacag ccctcctcat ataaaaagta ttcgttcact tccgataagc    24480
gtcgtaattt tctatctttc atcatattct agatccctct gaaaaaatct tccgagtttg    24540
ctaggcactg atacataact cttttccaat aattggggaa gtcattcaaa tctataatag    24600
gtttcagatt tgcttcaata aattctgact gtagctgctg aaacgttgcg gttgaactat    24660
atttccttat aacttttacg aaagagtttc tttgagtaat cacttcactc aagtgcttcc    24720
ctgcctccaa acgatacctg ttagcaatat ttaatagctt gaaatgatga agagctctgt    24780
gtttgtcttc ctgcctccag ttcgccgggc attcaacata aaaactgata gcacccggag    24840
ttccggaaac gaaatttgca tatacccatt gctcacgaaa aaaaatgtcc ttgtcgatat    24900
agggatgaat cgcttggtgt acctcatcta ctgcgaaaac ttgacctttc tctcccatat    24960
tgcagtcgcg gcacgatgga actaaattaa taggcatcac cgaaaattca ggataatgtg    25020
caataggaag aaaatgatct atattttttg tctgtcctat atcaccacaa aatggacatt    25080
tttcacctga tgaaacaagc atgtcatcgt aatatgttct agcgggtttg tttttatctc    25140
ggagattatt ttcataaagc ttttctaatt taaccttttgt caggttacca actactaagg    25200
ttgtaggctc aagagggtgt gtcctgtcgt aggtaaataa ctgacctgtc gagcttaata    25260
ttctatattg ttgttctttc tgcaaaaaag tggggaagtg agtaatgaaa ttatttctaa    25320
catttatctg catcatacct tccgagcatt tattaagcat ttcgctataa gttctcgctg    25380
gaagaggtag tttttttcatt gtacttttacc ttcatctctg ttcattatca tcgcttttaa    25440
aacggttcga ccttctaatc ctatctgacc attataattt tttagaatgg tttcataaga    25500
aagctctgaa tcaacggact gcgataataa gtggtggtat ccagaatttg tcacttcaag    25560
taaaaacacc tcacgagtta aaacacctaa gttctcaccg aatgtctcaa tatccggacg    25620
gataatattt attgcttctc ttgaccgtag gactttccac atgcaggatt ttggaacctc    25680
ttgcagtact actggggaat gagttgcaat tattgctaca ccattgcgtg catcgagtaa    25740
gtcgcttaat gttcgtaaaa aagcagagag caaaggtgga tgcagatgaa cctctggttc    25800
atcgaataaa actaatgact tttcgccaac gacatctact aatcttgtga tagtaaataa    25860
aacaattgca tgtccagagc tcattcgaag cagatatttc tggatattgt cataaaacaa    25920
tttagtgaat ttatcatcgt ccacttgaat ctgtggttca ttacgtctta actcttcata    25980
tttagaaatg aggctgatga gttccatatt tgaaaagttt tcatcactac ttagtttttt    26040
gatagcttca agccagagtt gtcttttttct atctactctc atacaaccaa taaatgctga    26100
aatgaattct aagcggagat cgcctagtga ttttaaacta ttgctggcag cattcttgag    26160
tccaatataa aagtattgtg tacctttttgc tgggtcaggt tgttctttag gaggagtaaa    26220
aggatcaaat gcactaaacg aaactgaaac aagcgatcga aatatccct ttgggattct    26280 tgactcgata agtctattat tttcagagaa aaaatattca ttgttttctg ggttggtgat    26340
tgcaccaatc attccattca aaattgttgt tttaccacac ccattccgcc cgataaaagc    26400
```

```
atgaatgttc gtgctgggca tagaattaac cgtcacctca aaaggtatag ttaaatcact   26460
gaatccggga gcactttttc tattaaatga aaagtggaaa tctgacaatt ctggcaaacc   26520
atttaacaca cgtgcgaact gtccatgaat ttctgaaaga gttacccctc taagtaatga   26580
ggtgttaagg acgctttcat tttcaatgtc ggctaatcga tttggccata ctactaaatc   26640
ctgaatagct ttaagaaggt tatgtttaaa accatcgctt aatttgctga gattaacata   26700
gtagtcaatg ctttcaccta aggaaaaaaa catttcaggg agttgactga atttttatc   26760 tattaatgaa taagtgctta cttcttcttt ttgacctaca aaaccaattt taacatttcc   26820
gatatcgcat ttttcaccat gctcatcaaa gacagtaaga taaaacattg taacaaagga   26880
atagtcattc caaccatctg ctcgtaggaa tgccttattt ttttctactg caggaatata   26940
cccgcctctt tcaataacac taaactccaa catatagtaa cccttaattt tattaaaata   27000
accgcaattt atttggcggc aacacaggat ctctctttta agttactctc tattacatac   27060
gttttccatc taaaaattag tagtattgaa cttaacgggg catcgtattg tagttttcca   27120
tatttagctt tctgcttcct tttggataac ccactgttat tcatgttgca tggtgcactg   27180
tttataccaa cgatatagtc tattaatgca tatatagtat cgccgaacga ttagctcttc   27240
aggcttctga agaagcgttt caagtactaa taagccgata gatagccacg gacttcgtag   27300
ccatttttca taagtgttaa cttccgctcc tcgctcataa cagacattca ctacagttat   27360
ggcggaaagg tatgcatgct gggtgtgggg aagtcgtgaa agaaaagaag tcagctgcgt   27420
cgtttgacat cactgctatc ttcttactgg ttatgcaggt cgtagtgggt ggcacacaaa   27480
gctttgcact ggattgcgag gctttgtgct tctctggagt gcgacaggtt tgatgacaaa   27540
aaattagcgc aagaagacaa aaatcacctt gcgctaatgc tctgttacag gtcactaata   27600
ccatctaagt agttgattca tagtgactgc atatgttgtg ttttacagta ttatgtagtc   27660
tgttttttat gcaaaatcta atttaatata ttgatattta tatcatttta cgtttctcgt   27720
tcagcttttt tatactaagt tggcattata aaaaagcatt gcttatcaat ttgttgcaac   27780
gaacaggtca ctatcagtca aaataaaatc attatttgat ttcaattttg tcccactccc   27840
tgcctctgtc atcacgatac tgtgatgcca tggtgtccga cttatgcccg agaagatgtt   27900
gagcaaactt atcgcttatc tgcttctcat agagtcttgc agacaaactg cgcaactcgt   27960
gaaaggtagg cggatcccct tcgaaggaaa gacctgatgc ttttcgtgcg cgcataaaat   28020
accttgatac tgtgccggat gaaagcggtt cgcgacgagt agatgcaatt atggtttctc   28080
cgccaagaat ctctttgcat ttatcaagtg tttccttcat tgatattccg agagcatcaa   28140
tatgcaatgc tgttgggatg gcaattttta cgcctgtttt gctttgctcg acataaagat   28200
atccatctac gatatcagac cacttcattt cgcataaatc accaactcgt tgcccggtaa   28260
caacagccag ttccattgca agtctgagcc aacatggtga tgattctgct gcttgataaa   28320
ttttcaggta ttcgtcagcc gtaagtcttg atctccttac ctctgatttt gctgcgcgag   28380
tggcagcgac atggtttgtt gttatatggc cttcagctat tgcctctcgg aatgcatcgc   28440
tcagtgttga tctgattaac ttggctgacg ccgccttgcc ctcgtctatg tatccattga   28500
gcattgccgc aatttctttt gtggtgatgt cttcaagtgg agcatcaggc agacccctcc   28560
ttattgcttt aattttgctc atgtaattta tgagtgtctt ctgcttgatt cctctgctgg   28620
ccaggatttt ttcgtagcga tcaagccatg aatgtaacgt aacggaatta tcactgttga   28680
ttctcgctgt cagaggcttg tgtttgtgtc ctgaaaataa ctcaatgttg gcctgtatag   28740
```

```
cttcagtgat tgcgattcgc ctgtctctgc ctaatccaaa ctctttaccc gtccttgggt    28800
ccctgtagca gtaatatcca ttgtttctta tataaaggtt aggggtaaa tcccggcgct    28860 catgacttcg ccttcttccc atttctgatc ctcttcaaaa ggccacctgt tactggtcga    28920
tttaagtcaa cctttaccgc tgattcgtgg aacagatact ctcttccatc cttaaccgga    28980
ggtgggaata tcctgcattc ccgaacccat cgacgaactg tttcaaggct tcttggacgt    29040
cgctggcgtg cgttccactc ctgaagtgtc aagtacatcg caaagtctcc gcaattacac    29100
gcaagaaaaa accgccatca ggcggcttgg tgttctttca gttcttcaat tcgaatattg    29160
gttacgtctg catgtgctat ctgcgcccat atcatccagt ggtcgtagca gtcgttgatg    29220
ttctccgctt cgataactct gttgaatggc tctccattcc attctcctgt gactcggaag    29280
tgcatttatc atctccataa aacaaaaccc gccgtagcga gttcagataa aataaatccc    29340
cgcgagtgcg aggattgtta tgtaatattg ggtttaatca tctatatgtt ttgtacagag    29400
agggcaagta tcgtttccac cgtactcgtg ataataattt gcacggtat cagtcatttc     29460 tcgcacattg cagaatgggg atttgtcttc attagactta taaaccttca tggaatattt    29520
gtatgccgac tctatatcta taccttcatc tacataaaca ccttcgtgat gtctgcatgg    29580
agacaagaca ccggatctgc acaacattga taacgcccaa tcttttgct cagactctaa     29640 ctcattgata ctcatttata aactccttgc aatgtatgtc gtttcagcta acggtatca     29700 gcaatgttta tgtaaagaaa cagtaagata atactcaacc cgatgtttga gtacggtcat    29760
catctgacac tacagactct ggcatcgctg tgaagacgac gcgaaattca gcattttcac    29820
aagcgttatc ttttacaaaa ccgatctcac tctcctttga tgcgaatgcc agcgtcagac    29880
atcatatgca gatactcacc tgcatcctga acccattgac ctccaacccc gtaatagcga    29940
tgcgtaatga tgtcgatagt tactaacggg tcttgttcga ttaactgccg cagaaactct    30000
tccaggtcac cagtgcagtg cttgataaca ggagtcttcc caggatggcg aacaacaaga    30060
aactggtttc cgtcttcacg gacttcgttg cttttccagtt tagcaatacg cttactccca    30120
tccgagataa caccttcgta atactcacgc tgctcgttga gttttgattt gctgtttca    30180 agctcaacac gcagttttccc tactgttagc gcaatatcct cgttctcctg gtcgcggcgt    30240
ttgatgtatt gctggtttct ttcccgttca tccagcagtt ccagcacaat cgatggtgtt    30300
accaattcat ggaaaaggtc tgcgtcaaat ccccagtcgt catgcattgc ctgctctgcc    30360
gcttcacgca gtgcctgaga gttaatttcg ctcacttcga acctctctgt ttactgataa    30420
gttccagatc ctcctggcaa cttgcacaag tccgacaacc ctgaacgacc aggcgtcttc    30480
gttcatctat cggatcgcca cactcacaac aatgagtggc agatatagcc tggtggttca    30540
ggcggcgcat ttttattgct gtgttgcgct gtaattcttc tatttctgat gctgaatcaa    30600
tgatgtctgc catctttcat taatccctga actgttggtt aatacgcttg agggtgaatg    30660
cgaataataa aaaaggagcc tgtagctccc tgatgatttt gcttttcatg ttcatcgttc    30720
cttaaagacg ccgtttaaca tgccgattgc caggcttaaa tgagtcggtg tgaatcccat    30780
cagcgttacc gtttcgcggt gcttcttcag tacgctacgg caaatgtcat cgacgttttt    30840
atccggaaac tgctgtctgg ctttttttga tttcagaatt agcctgacgg gcaatgctgc    30900
gaagggcgtt ttcctgctga ggtgtcattg aacaagtccc atgtcggcaa gcataagcac    30960
acagaatatg aagcccgctg ccagaaaaat gcattccgtg gttgtcatac ctggtttctc    31020
tcatctgctt ctgctttcgc caccatcatt tccagctttg tgaaaggga tgcggctaac    31080 gtatgaaatt cttcgtctgt ttctactggt attggcacaa acctgattcc aatttgagca    31140
```

```
aggctatgtg ccatctcgat actcgttctt aactcaacag aagatgcttt gtgcatacag   31200
cccctcgttt attatttatc tcctcagcca gccgctgtgc tttcagtgga tttcggataa   31260
cagaaaggcc gggaaatacc cagcctcgct ttgtaacgga gtagacgaaa gtgattgcgc   31320
ctacccggat attatcgtga ggatgcgtca tcgccattgc tccccaaata caaaaccaat   31380
ttcagccagt gcctcgtcca ttttttcgat gaactccggc acgatctcgt caaaactcgc   31440
catgtacttt tcatcccgct caatcacgac ataatgcagg ccttcacgct tcatacgcgg   31500
gtcatagttg gcaaagtacc aggcattttt tcgcgtcacc cacatgctgt actgcacctg   31560
ggccatgtaa gctgacttta tggcctcgaa accaccgagc cggaacttca tgaaatcccg   31620
ggaggtaaac gggcatttca gttcaaggcc gttgccgtca ctgcataaac catcgggaga   31680
gcaggcggta cgcatacttt cgtcgcgata gatgatcggg gattcagtaa cattcacgcc   31740
ggaagtgaat tcaaacaggg ttctggcgtc gttctcgtac tgttttcccc aggccagtgc   31800
tttagcgtta acttccggag ccacaccggt gcaaacctca gcaagcaggg tgtggaagta   31860
ggacattttc atgtcaggcc acttcttttcc ggagcggggt tttgctatca cgttgtgaac   31920
ttctgaagcg gtgatgacgc cgagccgtaa tttgtgccac gcatcatccc cctgttcgac   31980
agctctcaca tcgatcccgg tacgctgcag gataatgtcc ggtgtcatgc tgccaccttc   32040
tgctctgcgg ctttctgttt caggaatcca agagctttta ctgcttcggc ctgtgtcagt   32100
tctgacgatg cacgaatgtc gcggcgaaat atctgggaac agagcggcaa taagtcgtca   32160
tcccatgttt tatccagggc gatcagcaga gtgttaatct cctgcatggt ttcatcgtta   32220
accggagtga tgtcgcgttc cggctgacgt tctgcagtgt atgcagtatt ttcgacaatg   32280
cgctcggctt catccttgtc atagatacca gcaaatccga aggccagacg ggcacactga   32340
atcatggctt tatgacgtaa catccgtttg ggatgcgact gccacggccc cgtgatttct   32400
ctgccttcgc gagttttgaa tggttcgcgg cggcattcat ccatccattc ggtaacgcag   32460
atcggatgat tacggtcctt gcggtaaatc cggcatgtac aggattcatt gtcctgctca   32520
aagtccatgc catcaaactg ctggttttca ttgatgatgc gggaccagcc atcaacgccc   32580
accaccggaa cgatgccatt ctgcttatca ggaaaggcgt aaatttcttt cgtccacgga   32640
ttaaggccgt actggttggc aacgatcagt aatgcgatga actgcgcatc gctggcatca   32700
cctttaaatg ccgtctggcg aagagtggtg atcagttcct gtgggtcgac agaatccatg   32760
ccgacacgtt cagccagctt cccagccagc gttgcgagtg cagtactcat tcgttttata   32820
cctctgaatc aatatcaacc tggtggtgag caatggtttc aaccatgtac cggatgtgtt   32880
ctgccatgcg ctcctgaaac tcaacatcgt catcaaacgc acgggtaatg gattttttgc   32940
tggccccgtg gcgttgcaaa tgatcgatgc atagcgattc aaacaggtgc tggggcaggc   33000 cttttttccat gtcgtctgcc agttctgcct cttttctcttc acgggcgagc tgctggtagt   33060
gacgcgccca gctctgagcc tcaagacgat cctgaatgta taagcgttc atggctgaac   33120 tcctgaaata gctgtgaaaa tatcgcccgc gaaatgccgg gctgattagg aaaacaggaa   33180 aggggggttag tgaatgcttt tgcttgatct cagtttcagt attaatatcc atttttata   33240 agcgtcgacg gcttcacgaa acatcttttc atcgccaata aaagtggcga tagtgaattt   33300
agtctggata gccataagtg tttgatccat tctttgggac tcctggctga ttaagtatgt   33360
cgataaggcg tttccatccg tcacgtaatt tacgggtgat tcgttcaagt aaagattcgg   33420
aagggcagcc agcaacaggc caccctgcaa tggcatattg catggtgtgc tccttattta   33480
```

```
tacataacga aaaacgcctc gagtgaagcg ttattggtat gcggtaaaac cgcactcagg    33540
cggccttgat agtcatatca tctgaatcaa atattcctga tgtatcgata tcggtaattc    33600
ttattccttc gctaccatcc attggaggcc atccttcctg accatttcca tcattccagt    33660
cgaactcaca cacaacacca tatgcattta agtcgcttga aattgctata agcagagcat    33720
gttgcgccag catgattaat acagcattta atacagagcc gtgtttattg agtcggtatt    33780
cagagtctga ccagaaatta ttaatctggt gaagttttc ctctgtcatt acgtcatggt    33840
cgatttcaat ttctattgat gctttccagt cgtaatcaat gatgtatttt ttgatgtttg    33900
acatctgttc atatcctcac agataaaaaa tcgccctcac actggagggc aaagaagatt    33960
tccaataatc agaacaagtc ggctcctgtt tagttacgag cgacattgct ccgtgtattc    34020
actcgttgga atgaatacac agtgcagtgt ttattctgtt atttatgcca aaaataaagg    34080
ccactatcag gcagctttgt tgttctgttt accaagttct ctggcaatca ttgccgtcgt    34140
tcgtattgcc catttatcga catatttccc atcttccatt acaggaaaca tttcttcagg    34200
cttaaccatg cattccgatt gcagcttgca tccattgcat cgcttgaatt gtccacacca    34260 ttgatttta tcaatagtcg tagtcatacg gatagtcctg gtattgttcc atcacatcct    34320
gaggatgctc ttcgaactct tcaaattctt cttccatata tcaccttaaa tagtggattg    34380
cggtagtaaa gattgtgcct gtctttaac cacatcaggc tcggtggttc tcgtgtaccc    34440
ctacagcgag aaatcggata aactattaca acccctacag tttgatgagt atagaaatgg    34500
atccactcgt tattctcgga cgagtgttca gtaatgaacc tctggagaga accatgtata    34560
tgatcgttat ctgggttgga cttctgcttt taagcccaga taactggcct gaatatgtta    34620
atgagagaat cggtattcct catgtgtggc atgttttcgt cttgctctt gcattttcgc    34680 tagcaattaa tgtgcatcga ttatcagcta ttgccagcgc cagatataag cgatttaagc    34740
taagaaaacg cattaagatg caaaacgata aagtgcgatc agtaattcaa aaccttacag    34800
aagagcaatc tatggttttg tgcgcagccc ttaatgaagg caggaagtat gtggttacat    34860
caaaacaatt cccatacatt agtgagttga ttgagcttgg tgtgttgaac aaaactttt    34920 cccgatggaa tggaaagcat atattattcc ctattgagga tatttactgg actgaattag    34980
ttgccagcta tgatccatat aatattgaga taaagccaag gccaatatct aagtaactag    35040
ataagaggaa tcgatttcc cttaattttc tggcgtccac tgcatgttat gccgcgttcg    35100
ccaggcttgc tgtaccatgt gcgctgattc ttgcgctcaa tacgttgcag gttgctttca    35160 atctgttgt ggtattcagc cagcactgta aggtctatcg gatttagtgc gctttctact    35220
cgtgatttcg gtttgcgatt cagcgagaga atagggcggt taactggttt tgcgcttacc    35280
ccaaccaaca ggggatttgc tgctttccat tgagcctgtt tctctgcgcg acgttcgcgg    35340
cggcgtgttt gtgcatccat ctggattctc ctgtcagtta gctttggtgg tgtgtggcag    35400
ttgtagtcct gaacgaaaac ccccgcgat tggcacattg gcagctaatc cggaatcgca    35460
cttacggcca atgcttcgtt tcgtatcaca caccccaaag ccttctgctt tgaatgctgc    35520
ccttcttcag ggcttaattt ttaagagcgt caccttcatg gtggtcagtg cgtcctgctg    35580
atgtgctcag tatcaccgcc agtggtattt atgtcaacac cgccagagat aatttatcac    35640
cgcagatggt tatctgtatg ttttttatat gaatttattt tttgcagggg ggcattgttt    35700
ggtaggtgag agatctgaat tgctatgttt agtgagttgt atctatttat ttttcaataa    35760
atacaattgg ttatgtgttt tggggcgat cgtgaggcaa agaaacccg cgcgtgaggc    35820 cgggttattc ttgttctctg gtcaaattat atagttggaa aacaaggatg catatatgaa    35880
```

```
tgaacgatgc agaggcaatg ccgatggcga tagtgggtat catgtagccg cttatgctgg   35940
aaagaagcaa taacccgcag aaaaacaaag ctccaagctc aacaaaacta agggcataga   36000
caataactac cgatgtcata tacccatact ctctaatctt ggccagtcgg cgcgttctgc   36060
ttccgattag aaacgtcaag gcagcaatca ggattgcaat catggttcct gcatatgatg   36120
acaatgtcgc cccaagacca tctctatgag ctgaaaaaga aacaccagga atgtagtggc   36180
ggaaaaggag atagcaaatg cttacgataa cgtaaggaat tattactatg taaacaccag   36240
gcatgattct gttccgcata attactcctg ataattaatc cttaactttg cccacctgcc   36300 tttttaaaaca ttccagtata tcactttttca ttcttgcgta gcaatatgcc atctcttcag   36360
ctatctcagc attggtgacc ttgttcagag gcgctgagag atggcctttt tctgatagat   36420
aatgttctgt taaatatatct ccggcctcat cttttgcccg caggctaatg tctgaaaatt   36480
gaggtgacgg gttaaaaata atatccttgg caaccttttt tatatccctt ttaaattttg   36540
gcttaatgac tatatccaat gagtcaaaaa gctccccttc aatatctgtt gcccctaaga   36600
cctttaatat atcgccaaat acaggtagct tggcttctac cttcaccgtt gttcggccga   36660
tgaaatgcat atgcataaca tcgtctttgg tggttcccct catcagtggc tctatctgaa   36720
cgcgctctcc actgcttaat gacattcctt tcccgattaa aaaatctgtc agatcggatg   36780
tggtcggccc gaaaacagtt ctggcaaaac caatggtgtc gccttcaaca aacaaaaaag   36840
atgggaatcc caatgattcg tcatctgcga ggctgttctt aatatcttca actgaagctt   36900
tagagcgatt tatcttctga accagactct tgtcatttgt tttggtaaag agaaaagttt   36960
ttccatcgat tttatgaata tacaaataat tggagccaac ctgcaggtga tgattatcag   37020
ccagcagaga attaaggaaa acagacaggt ttattgagcg cttatctttc cctttatttt   37080
tgctgcggta agtcgcataa aaaccattct tcataattca atccatttac tatgttatgt   37140
tctgagggga gtgaaaattc ccctaattcg atgaagattc ttgctcaatt gttatcagct   37200
atgcgccgac cagaacacct tgccgatcag ccaaacgtct cttcaggcca ctgactagcg   37260
ataactttcc ccacaacgga acaactctca ttgcatggga tcattgggta ctgtgggttt   37320
agtggttgta aaaacacctg accgctatcc ctgatcagtt tcttgaaggt aaactcatca   37380
cccccaagtc tggctatgca gaaatcacct ggctcaacag cctgctcagg gtcaacgaga   37440
attaacattc cgtcaggaaa gcttggcttg gagcctgttg gtgcggtcat ggaattacct   37500
tcaacctcaa gccagaatgc agaatcactg gcttttttgg ttgtgcttac ccatctctcc   37560
gcatcacctt tggtaaaggt tctaagctta ggtgagaaca tccctgcctg aacatgagaa   37620
aaaacagggt actcatactc acttctaagt gacggctgca tactaaccgc ttcatacatc   37680
tcgtagattt ctctggcgat tgaagggcta aattcttcaa cgctaacttt gagaattttt   37740
gtaagcaatg cggcgttata agcatttaat gcattgatgc cattaaataa agcaccaacg   37800
cctgactgcc ccatccccat cttgtctgcg acagattcct gggataagcc aagttcattt   37860 ttctttttttt cataaattgc tttaaggcga cgtgcgtcct caagctgctc ttgtgttaat   37920
ggtttctttt ttgtgctcat acgttaaatc tatcaccgca agggataaat atctaacacc   37980
gtgcgtgttg actattttac ctctggcggt gataatggtt gcatgtacta aggaggttgt   38040
atggaacaac gcataaccct gaaagattat gcaatgcgct ttgggcaaac caagacagct   38100
aaagatctcg gcgtatatca aagcgcgatc aacaaggcca ttcatgcagg ccgaaagatt   38160 ttttttaacta taaacgctga tggaagcgtt tatgcggaag aggtaaagcc cttcccgagt   38220
```

```
aacaaaaaaa caacagcata ataaccccg ctcttacaca ttccagccct gaaaaagggc    38280
atcaaattaa accacaccta tggtgtatgc atttatttgc atacattcaa tcaattgtta    38340
tctaaggaaa tacttacata tggttcgtgc aaacaaacgc aacgaggctc tacgaatcga    38400
gagtgcgttg cttaacaaaa tcgcaatgct tggaactgag aagacagcgg aagctgtggg    38460
cgttgataag tcgcagatca gcaggtggaa gagggactgg attccaaagt tctcaatgct    38520
gcttgctgtt cttgaatggg gggtcgttga cgacgacatg gctcgattgg cgcgacaagt    38580
tgctgcgatt ctcaccaata aaaaacgccc ggcggcaacc gagcgttctg aacaaatcca    38640
gatggagttc tgaggtcatt actggatcta tcaacaggag tcattatgac aaatacagca    38700
aaaatactca acttcggcag aggtaacttt gccggacagg agcgtaatgt ggcagatctc    38760
gatgatggtt acgccagact atcaaatatg ctgcttgagg cttattcggg cgcagatctg    38820
accaagcgac agtttaaagt gctgcttgcc attctgcgta aaacctatgg gtggaataaa    38880
ccaatggaca gaatcaccga ttctcaactt agcgagatta caaagttacc tgtcaaacgg    38940
tgcaatgaag ccaagttaga actcgtcaga atgaatatta tcaagcagca aggcggcatg    39000
tttggaccaa ataaaaacat ctcagaatgg tgcatccctc aaaacgaggg aaaatcccct    39060
aaaacgaggg ataaaacatc cctcaaattg ggggattgct atccctcaaa acaggggac    39120 acaaagacac ctattacaaa agaaaaaaga aagattatt cgtcagagaa ttctggcgaa    39180
tcctctgacc agccagaaaa cgacctttct gtggtgaaac cggatgctgc aattcagagc    39240
ggcagcaagt gggggacagc agaagacctg accgccgcag agtggatgtt tgacatggtg    39300
aagactatcg caccatcagc cagaaaaccg aattttgctg ggtgggctaa cgatatccgc    39360
ctgatgcgtg aacgtgacgg acgtaaccac cgcgacatgt gtgtgctgtt ccgctgggca    39420
tgccaggaca acttctggtc cggtaacgtg ctgagcccgg ccaaactccg cgataagtgg    39480
acccaactcg aaatcaaccg taacaagcaa caggcaggcg tgacagccag caaaccaaaa    39540
ctcgacctga caaacacaga ctggatttac ggggtggatc tatgaaaaac atcgccgcac    39600
agatggttaa cttcgaccgt gagcagatgc gtcggatcgc caacaacatg ccggaacagt    39660
acgacgaaaa gccgcaggta cagcaggtag cgcagatcat caacggtgtg ttcagccagt    39720
tactggcaac tttcccggcg agcctggcta accgtgacca gaacgaagtg aacgaaatcc    39780
gtcgccagtg ggttctggct tttcgggaaa acgggatcac cacgatggaa caggttaacg    39840
caggaatgcg cgtagcccgt cggcagaatc gaccatttct gccatcaccc gggcagtttg    39900
ttgcatggtg ccgggaagaa gcatccgtta ccgccggact gccaaacgtc agcgagctgg    39960
ttgatatggt ttacgagtat tgccggaagc gaggcctgta tccggatgcg gagtcttatc    40020
cgtggaaatc aaacgcgcac tactggctgg ttaccaacct gtatcagaac atgcgggcca    40080
atgcgcttac tgatgcggaa ttacgccgta aggccgcaga tgagcttgtc catatgactg    40140
cgagaattaa ccgtggtgag gcgatccctg aaccagtaaa acaacttcct gtcatgggcg    40200
gtagacctct aaatcgtgca caggctctgg cgaagatcgc agaaatcaaa gctaagttcg    40260
gactgaaagg agcaagtgta tgacgggcaa agaggcaatt attcattacc tggggacgca    40320
taatagcttc tgtgcgccgg acgttgccgc gctaacaggc gcaacagtaa ccagcataaa    40380
tcaggccgcg gctaaaatgg cacgggcagg tcttctggtt atcgaaggta aggtctggcg    40440
aacggtgtat taccgttttg ctaccaggga agaacgggaa ggaaagatga gcacgaacct    40500
ggtttttaag gagtgtcgcc agagtgccgc gatgaaacgg gtattggcgg tatatggagt    40560
taaaagatga ccatctacat tactgagcta ataacaggcc tgctggtaat cgcaggcctt    40620
```

```
tttatttggg ggagagggaa gtcatgaaaa aactaacctt tgaaattcga tctccagcac   40680
atcagcaaaa cgctattcac gcagtacagc aaatccttcc agacccaacc aaaccaatcg   40740
tagtaaccat tcaggaacgc aaccgcagct tagaccaaaa caggaagcta tgggcctgct   40800
taggtgacgt ctctcgtcag gttgaatggc atggtcgctg gctggatgca gaaagctgga   40860
agtgtgtgtt taccgcagca ttaaagcagc aggatgttgt tcctaacctt gccgggaatg   40920
gctttgtggt aataggccag tcaaccagca ggatgcgtgt aggcgaattt gcggagctat   40980
tagagcttat acaggcattc ggtacagagc gtggcgttaa gtggtcagac gaagcgagac   41040
tggctctgga gtgaaagcg agatggggag acagggctgc atgataaatg tcgttagttt   41100
ctccggtggc aggacgtcag catatttgct ctggctaatg gagcaaaagc gacgggcagg   41160
taaagacgtg cattacgttt tcatggatac aggttgtgaa catccaatga catatcggtt   41220
tgtcagggaa gttgtgaagt tctgggatat accgctcacc gtattgcagg ttgatatcaa   41280
cccggagctt ggacagccaa atggttatac ggtatgggaa ccaaaggata ttcagacgcg   41340
aatgcctgtt ctgaagccat ttatcgatat ggtaaagaaa tatggcactc catacgtcgg   41400
cggcgcgttc tgcactgaca gattaaaact cgttcccttc accaaatact gtgatgacca   41460
tttcgggcga gggaattaca ccacgtggat tggcatcaga gctgatgaac cgaagcggct   41520
aaagccaaag cctggaatca gatatcttgc tgaactgtca gactttgaga aggaagatat   41580
cctcgcatgg tggaagcaac aaccattcga tttgcaaata ccggaacatc tcggtaactg   41640
catattctgc attaaaaaat caacgcaaaa aatcggactt gcctgcaaag atgaggaggg   41700
attgcagcgt gttttttaatg aggtcatcac gggatcccat gtgcgtgacg gacatcggga   41760
aacgccaaag gagattatgt accgaggaag aatgtcgctg gacggtatcg cgaaaatgta   41820
ttcagaaaat gattatcaag ccctgtatca ggacatggta cgagctaaaa gattcgatac   41880
cggctcttgt tctgagtcat gcgaaatatt tggagggcag cttgatttcg acttcgggag   41940
ggaagctgca tgatgcgatg ttatcggtgc ggtgaatgca aagaagataa ccgcttccga   42000
ccaaatcaac cttactggaa tcgatggtgt ctccggtgtg aaagaacacc aacagggtg   42060 ttaccactac cgcaggaaaa ggaggacgtg tggcgagaca cgacgaagt atcaccgaca   42120 taatctgcga aaactgcaaa taccttccaa cgaaacgcac cagaaataaa cccaagccaa   42180
tcccaaaaga atctgacgta aaaaccttca actacacggc tcacctgtgg gatatccggt   42240
ggctaagacg tcgtgcgagg aaaacaaggt gattgaccaa aatcgaagtt acgaacaaga   42300
aagcgtcgag cgagctttaa cgtgcgctaa ctgcggtcag aagctgcatg tgctggaagt   42360
tcacgtgtgt gagcactgct gcgcagaact gatgagcgat ccgaatagct cgatgcacga   42420
ggaagaagat gatggctaaa ccagcgcgaa gacgatgtaa aaacgatgaa tgccgggaat   42480
ggtttcaccc tgcattcgct aatcagtggt ggtgctctcc agagtgtgga accaagatag   42540
cactcgaacg acgaagtaaa gaacgcgaaa agcggaaaa agcagcagag aagaaacgac   42600
gacgagagga gcagaaacag aaagataaac ttaagattcg aaaactcgcc ttaaagcccc   42660
gcagttactg gattaaacaa gcccaacaag ccgtaaacgc cttcatcaga gaaagagacc   42720
gcgacttacc atgtatctcg tgcggaacgc tcacgtctgc tcagtgggat gccggacatt   42780
accggacaac tgctgcggca cctcaactcc gatttaatga acgcaatatt cacaagcaat   42840
gcgtggtgtg caaccagcac aaaagcggaa atctcgttcc gtatcgcgtc gaactgatta   42900
gccgcatcgg gcaggaagca gtagacgaaa tcgaatcaaa ccataaccgc catcgctgga   42960
```

```
ctatcgaaga gtgcaaggcg atcaaggcag agtaccaaca gaaactcaaa gacctgcgaa    43020
atagcagaag tgaggccgca tgacgttctc agtaaaaacc attccagaca tgctcgttga    43080
aacatacgga aatcagacag aagtagcacg cagactgaaa tgtagtcgcg gtacggtcag    43140
aaaatacgtt gatgataaag acgggaaaat gcacgccatc gtcaacgacg ttctcatggt    43200
tcatcgcgga tggagtgaaa gagatgcgct attacgaaaa aattgatggc agcaaatacc    43260
gaaatatttg ggtagttggc gatctgcacg gatgctacac gaacctgatg aacaaactgg    43320
atacgattgg attcgacaac aaaaaagacc tgcttatctc ggtgggcgat ttggttgatc    43380
gtggtgcaga gaacgttgaa tgcctggaat taatcacatt cccctggttc agagctgtac    43440
gtggaaacca tgagcaaatg atgattgatg cttatcaga gcgtggaaac gttaatcact    43500
ggctgcttaa tggcggtggc tggttcttta atctcgatta cgacaaagaa attctggcta    43560
aagctcttgc ccataaagca gatgaacttc cgttaatcat cgaactggtg agcaaagata    43620
aaaaatatgt tatctgccac gccgattatc cctttgacga atacgagttt ggaaagccag    43680
ttgatcatca gcaggtaatc tggaaccgcg aacgaatcag caactcacaa aacgggatcg    43740
tgaaagaaat caaaggcgcg gacacgttca tctttggtca tacgccagca gtgaaaccac    43800
tcaagtttgc caaccaaatg tatatcgata ccggcgcagt gttctgcgga aacctaacat    43860
tgattcaggt acaggagaa ggcgcatgag actcgaaagc gtagctaaat ttcattcgcc    43920
aaaaagcccg atgatgagcg actcaccacg ggccacggct tctgactctc tttccggtac    43980
tgatgtgatg gctgctatgg ggatggcgca atcacaagcc ggattcggta tggctgcatt    44040
ctgcggtaag cacgaactca gccagaacga caaacaaaag gctatcaact atctgatgca    44100
atttgcacac aaggtatcgg ggaaataccg tggtgtggca agcttgaag gaaatactaa    44160 ggcaaaggta ctgcaagtgc tcgcaacatt cgcttatgcg gattattgcc gtagtgccgc    44220
gacgccgggg gcaagatgca gagattgcca tggtacaggc cgtgcggttg atattgccaa    44280
aacagagctg tggggagag ttgtcgagaa agagtgcgga agatgcaaag gcgtcggcta    44340
ttcaaggatg ccagcaagcg cagcatatcg cgctgtgacg atgctaatcc caaaccttac    44400
ccaacccacc tggtcacgca ctgttaagcc gctgtatgac gctctggtgg tgcaatgcca    44460
caaagaagag tcaatcgcag acaacatttt gaatgcggtc acacgttagc agcatgattg    44520
ccacggatgg caacatatta acggcatgat attgacttat tgaataaaat tgggtaaatt    44580
tgactcaacg atgggttaat tcgctcgttg tggtagtgag atgaaaagag gcggcgctta    44640
ctaccgattc cgcctagttg gtcacttcga cgtatcgtct ggaactccaa ccatcgcagg    44700
cagagaggtc tgcaaaatgc aatcccgaaa cagttcgcag gtaatagtta gagcctgcat    44760
aacggtttcg ggattttta tatctgcaca acaggtaaga gcattgagtc gataatcgtg    44820
aagagtcggc gagcctggtt agccagtgct ctttccgttg tgctgaatta agcgaatacc    44880
ggaagcagaa ccggatcacc aaatgcgtac aggcgtcatc gccgcccagc aacagcacaa    44940
cccaaactga gccgtagcca ctgtctgtcc tgaattcatt agtaatagtt acgctgcggc    45000
cttttacaca tgaccttcgt gaaagcgggt ggcaggaggt cgcgctaaca acctcctgcc    45060
gttttgcccg tgcatatcgg tcacgaacaa atctgattac taaacacagt agcctggatt    45120
tgttctatca gtaatcgacc ttattcctaa ttaaatagag caaatcccct tattggggt    45180 aagacatgaa gatgccagaa aaacatgacc tgttggccgc cattctcgcg gcaaaggaac    45240
aaggcatcgg ggcaatcctt gcgtttgcaa tggcgtacct tcgcggcaga tataatggcg    45300
gtgcgtttac aaaaacagta atcgacgcaa cgatgtgcgc cattatcgcc tagttcattc    45360
```

```
gtgaccttct cgacttcgcc ggactaagta gcaatctcgc ttatataacg agcgtgttta    45420
tcggctacat cggtactgac tcgattggtt cgcttatcaa acgcttcgct gctaaaaaag    45480
ccggagtaga agatggtaga aatcaataat caacgtaagg cgttcctcga tatgctggcg    45540
tggtcggagg gaactgataa cggacgtcag aaaaccagaa atcatggtta tgacgtcatt    45600
gtaggcggag agctatttac tgattactcc gatcaccctc gcaaacttgt cacgctaaac    45660
ccaaaactca aatcaacagg cgccggacgc taccagcttc tttcccgttg gtgggatgcc    45720
taccgcaagc agcttggcct gaaagacttc tctccgaaaa gtcaggacgc tgtggcattg    45780
cagcagatta aggagcgtgg cgcttttacct atgattgatc gtggtgatat ccgtcaggca    45840
atcgaccgtt gcagcaatat ctgggcttca ctgccgggcg ctggttatgg tcagttcgag    45900
cataaggctg acagcctgat tgcaaaattc aaagaagcgg gcggaacggt cagagagatt    45960
gatgtatgag cagagtcacc gcgattatct ccgctctggt tatctgcatc atcgtctgcc    46020
tgtcatgggc tgttaatcat taccgtgata acgccattac ctacaaagcc cagcgcgaca    46080
aaaatgccag agaactgaag ctggcgaacg cggcaattac tgacatgcag atgcgtcagc    46140
gtgatgttgc tgcgctcgat gcaaaatacag cgaaggagtt agctgatgct aaagctgaaa    46200
atgatgctct gcgtgatgat gttgccgctg tcgtcgtcg gttgcacatc aaagcagtct    46260
gtcagtcagt gcgtgaagcc accaccgcct ccggcgtgga taatgcagcc tccccccgac    46320
tggcagacac cgctgaacgg gattatttca ccctcagaga gaggctgatc actatgcaaa    46380
aacaactgga aggaacccag aagtatatta atgagcagtg cagatagagt tgcccatatc    46440
gatgggcaac tcatgcaatt attgtgagca atacacacgc gcttccagcg gagtataaat    46500
gcctaaagta ataaaaccga gcaatccatt tacgaatgtt tgctgggttt ctgttttaac    46560 aacatttct gcgccgccac aaattttggc tgcatcgaca gttttcttct gcccaattcc    46620
agaaacgaag aaatgatggg tgatggtttc ctttggtgct actgctgccg gtttgttttg    46680
aacagtaaac gtctgttgag cacatcctgt aataagcagg gccagcgcag tagcgagtag    46740
catttttttc atggtgttat tcccgatgct ttttgaagtt cgcagaatcg tatgtgtaga    46800
aaattaaaca aaccctaaac aatgagttga aatttcatat tgttaatatt tattaatgta    46860
tgtcaggtgc gatgaatcgt cattgtattc ccggattaac tatgtccaca gccctgacgg    46920
ggaacttctc tgcgggagtg tccgggaata attaaaacga tgcacacagg gtttagcgcg    46980
tacacgtatt gcattatgcc aacgccccgg tgctgacacg gaagaaaccg gacgttatga    47040
tttagcgtgg aaagatttgt gtagtgttct gaatgctctc agtaaatagt aatgaattat    47100
caaaggtata gtaatatctt ttatgttcat ggatatttgt aacccatcgg aaaactcctg    47160
ctttagcaag attttccctg tattgctgaa atgtgatttc tcttgatttc aacctatcat    47220
aggacgtttc tataagatgc gtgtttcttg agaatttaac atttacaacc ttttttaagtc    47280 cttttattaa cacggtgtta tcgttttcta acacgatgtg aatattatct gtggctagat    47340
agtaaatata atgtgagacg ttgtgacgtt ttagttcaga ataaaacaat tcacagtcta    47400 aatctttcg cacttgatcg aatatttctt taaaaatggc aacctgagcc attggtaaaa    47460
ccttccatgt gatacgaggg cgcgtagttt gcattatcgt ttttatcgtt tcaatctggt    47520
ctgacctcct tgtgttttgt tgatgattta tgtcaaatat taggaatgtt ttcacttaat    47580
agtattggtt gcgtaacaaa gtgcggtcct gctggcattc tggagggaaa tacaaccgac    47640
agatgtatgt aaggccaacg tgctcaaatc ttcatacaga aagatttgaa gtaatatttt    47700
```

-continued

| | |
|---|---|
| aaccgctaga tgaagagcaa gcgcatggag cgacaaaatg aataaagaac aatctgctga | 47760 |
| tgatccctcc gtggatctga ttcgtgtaaa aaatatgctt aatagcacca tttctatgag | 47820 |
| ttaccctgat gttgtaattg catgtataga acataaggtg tctctggaag cattcagagc | 47880 |
| aattgaggca gcgttggtga agcacgataa taatatgaag gattattccc tggtggttga | 47940 |
| ctgatcacca taactgctaa tcattcaaac tatttagtct gtgacagagc caacacgcag | 48000 |
| tctgtcactg tcaggaaagt ggtaaaactg caactcaatt actgcaatgc cctcgtaatt | 48060 |
| aagtgaattt acaatatcgt cctgttcgga gggaagaacg cgggatgttc attcttcatc | 48120 |
| acttttaatt gatgtatatg ctctcttttc tgacgttagt ctccgacggc aggcttcaat | 48180 |
| gacccaggct gagaaattcc cggaccctt ttgctcaaga gcgatgttaa tttgttcaat | 48240 |
| catttggtta ggaaagcgga tgttgcgggt tgttgttctg cgggttctgt tcttcgttga | 48300 |
| catgaggttg ccccgtattc agtgtcgctg atttgtattg tctgaagttg tttttacgtt | 48360 |
| aagttgatgc agatcaatta atacgatacc tgcgtcataa ttgattattt gacgtggttt | 48420 |
| gatggcctcc acgcacgttg tgatatgtag atgataatca ttatcacttt acgggtcctt | 48480 |
| tccggtgatc cgacaggtta cg | 48502 |

<210> SEQ ID NO 44
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 44

| | |
|---|---|
| tttttttttt tttttttttt ttttt | 25 |

<210> SEQ ID NO 45
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 45

| | |
|---|---|
| gcaatatcag caccaacaga aac | 23 |

<210> SEQ ID NO 46
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 46

| | |
|---|---|
| gtttctgttg gtgctgatat tgctt | 25 |

<210> SEQ ID NO 47
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 47

| | |
|---|---|
| ccttctgtta cgtt | 14 |

<210> SEQ ID NO 48
<211> LENGTH: 13

```
<212> TYPE: DNA
<213> ORGANISM: Artificial Sequence
<220> FEATURE:
<223> OTHER INFORMATION: Synthetic Polynucleotide

<400> SEQUENCE: 48
ttcgtaacag aag                                                          13

<210> SEQ ID NO 49
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 49
cgttctgttt atgtttcttg gacactgatt gacacggttt agtagaac                    48

<210> SEQ ID NO 50
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 50
tttttttttt tttttttttt tttttttca agaaacataa acagaacg                     48

<210> SEQ ID NO 51
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 51
tttttttttt tt                                                           12

<210> SEQ ID NO 52
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 52
ggttgtttct gttggtgctg atattgcggc gtctgcttgg gtgtttaacc t                51

<210> SEQ ID NO 53
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 53
ggttaaacac ccaagcagac gccgcaatat cagcaccaac agaaacaacc tttgaggcga       60
gcggtcaa                                                                68

<210> SEQ ID NO 54
<211> LENGTH: 15
<212> TYPE: DNA
<213> ORGANISM: Artificial Sequence
<220> FEATURE:
<223> OTHER INFORMATION: Synthetic Polynucleotide
```

```
<400> SEQUENCE: 54
ttgaccgctc gcctc                                                    15
```

METHOD FOR CHARACTERISING A DOUBLE STRANDED NUCLEIC ACID USING A NANO-PORE AND ANCHOR MOLECULES AT BOTH ENDS OF SAID NUCLEIC ACID

This Application is a national stage filing under 35 U.S.C. § 371 of PCT International Application No. PCT/GB2015/050991, which has an international filing date of Mar. 31, 2015; is a continuation-in-part of PCT International Application No. PCT/GB2014/052737, which has an international filing date of Sep. 10, 2014; and claims foreign priority benefits under 35 U.S.C. § 119(a)-(d) or 35 U.S.C. § 365(b) of British application number 1407815.8, filed May 2, 2014, and British application number 1406147.7, filed Apr. 4, 2014, the contents of each of which are herein incorporated by reference in their entireties.

FIELD OF THE INVENTION

The invention relates to a method of characterising, such as sequencing, a target double stranded polynucleotide. The polynucleotide is coupled to a membrane using at least two adaptors with different strengths of coupling to the membrane.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

It has previously been demonstrated that ultra low concentration analyte delivery can be achieved by coupling the analyte to a membrane in which the relevant detector is present. This lowers by several orders of magnitude the amount of analyte required in order to be detected (WO 2012/164270).

It has also been shown that double stranded polynucleotides can be effectively characterised using strand sequencing if they are modified to include a Y adaptor (a double stranded stem and two non-complementary arms) containing a leader sequence and a hairpin loop adaptor (WO 2013/014451). It is preferred that that Y adaptor containing the leader sequence is attached to one end of the polynucleotide and the hairpin loop adaptor is attached to the other end. The leader sequence preferentially threads into the nanopore and the hairpin loop connecting the two strands of the polynucleotide allows both strands to be investigated as the polynucleotide unzips and moves through the pore. This is advantageous because it doubles the amount of information obtained from a single double stranded polynucleotide. Moreover, because the sequences in the two strands are complementary, the information from the two strands can be combined informatically. This mechanism provides an orthogonal proof-reading capability that provides higher confidence observations. When Y adaptors and hairpin loops are used together in this way, the Y adaptor typically contains an anchor which couples the polynucleotide to the membrane containing the nanopore. In some instances, double stranded polynucleotides having Y adaptors at both ends are produced in the sample preparation. The presence of the leader sequence and the anchor in the Y adaptors means that the system is typically biased towards characterising these polynucleotides. However, the lack of the hairpin loop linking the two strands in such polynucleotides means that only one strand is investigated.

SUMMARY OF THE INVENTION

The inventors have surprisingly demonstrated that it is possible to avoid a bias towards double stranded polynucleotides comprising a Y adaptor at both ends by including two anchors in the system. The inventors have used a Y adaptor comprising one or more first anchors for coupling the polynucleotide to the membrane and a hairpin loop adaptor comprising one or more second anchors for coupling the polynucleotide to the membrane. The hairpin loop adaptor couples the polynucleotide to the membrane with more strength than the Y adaptor.

Accordingly, the invention provides a method of characterising a target double stranded polynucleotide using a transmembrane pore in a membrane, comprising:

a) providing the target double stranded polynucleotide with a Y adaptor at one end and a hairpin loop adaptor at the other end, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane;

b) contacting the polynucleotide provided in step a) with the transmembrane pore such that at least one strand of the polynucleotide moves through the pore; and c) taking one or more measurements as the at least one strand of the polynucleotide moves with respect to the pore wherein the measurements are indicative of one or more characteristics of the at least one strand of the polynucleotide and thereby characterising the double stranded target polynucleotide.

The invention also provides:

a method for modifying a target double stranded polynucleotide for characterisation using a transmembrane pore in a membrane, comprising ligating a Y adaptor to one end of the polynucleotide and ligating a hairpin loop adaptor to the other end of the polynucleotide, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane, and thereby providing a modified target double stranded polynucleotide;

a method for modifying a target double stranded polynucleotide for characterisation using a transmembrane pore in a membrane, comprising: (a) ligating a Y adaptor to one end of the polynucleotide and ligating a hairpin loop adaptor to the other end of the polynucleotide; and (b) attaching to the Y adaptor one or more first anchors for coupling the polynucleotide to the membrane, attaching to the hairpin loop adaptor one or more second anchors for coupling the polynucleotide to the membrane and thereby providing a modified target double stranded polynucleotide; wherein the strength of coupling of the hairpin loop adaptor to the membrane is greater than the strength of coupling of the Y adaptor to the membrane;

a target double stranded polynucleotide modified using the method of the invention;

a method for modifying a target double stranded polynucleotide for characterisation using a transmembrane pore in a membrane, comprising contacting the target polynucleotide with a MuA transposase and a population of double stranded MuA substrates, wherein a proportion of the substrates in the population are Y adaptors comprising one or more first anchors for coupling the polynucleotide to the membrane, wherein a proportion of the substrates in the population are hairpin loop adaptors comprising one or more second anchors for coupling the polynucleotide to the membrane and wherein the strength of coupling of the hairpin loop adaptor to the membrane is greater than the strength of coupling of the Y adaptor to the membrane, and thereby producing a plurality of modified double stranded polynucleotides;

a method for modifying a target double stranded polynucleotide for characterisation using a transmembrane pore in a membrane, comprising: (a) contacting the target polynucleotide with a MuA transposase and a population of double stranded MuA substrates, wherein a proportion of the substrates in the population are Y adaptors and wherein a proportion of the substrates in the population are hairpin loop adaptors, such that the transposase fragments the target polynucleotide and ligates a substrate to one or both ends of the double stranded fragments and thereby produces a plurality of fragment/substrate constructs; and (b) attaching to the Y adaptors in the plurality of fragment/substrate constructs one or more first anchors and attaching to the hairpin loop adaptors in the plurality of fragment/substrate constructs one or more second anchors and thereby producing a plurality of modified double stranded polynucleotides; wherein the strength of coupling of each hairpin loop adaptor to the membrane is greater than the strength of coupling of each Y adaptor to the membrane;

a plurality of polynucleotides modified using the method of the invention;

a method of characterising a target double stranded polynucleotide using a transmembrane pore in a membrane, comprising:

a) providing the target double stranded polynucleotide with a Y adaptor at one end and a hairpin loop adaptor at the other end, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane;

b) contacting the polynucleotide provided in step a) with the transmembrane pore, a polymerase and labelled nucleotides such that phosphate labelled species are sequentially released when nucleotides are added to the polynucleotide by the polymerase, wherein the phosphate species contain a label specific for each nucleotide; and c) detecting the phosphate labelled species using the pore and thereby characterising the double stranded target polynucleotide;

a pair of adaptors for modifying a target double stranded polynucleotide for characterisation using a transmembrane pore in a membrane, wherein one adaptor is a Y adaptor comprising one or more first anchors for coupling the polynucleotide to the membrane, wherein the other adaptor is a hairpin loop adaptor comprising one or more second anchors for coupling the polynucleotide to the membrane and wherein the strength of coupling of the hairpin loop adaptor to the membrane is greater than the strength of coupling of the Y adaptor to the membrane;

a population of adaptors for modifying a target polynucleotide for characterisation using a transmembrane pore in a membrane, wherein a proportion of the adaptors are Y adaptors comprising one or more first anchors for coupling the polynucleotide to the membrane, wherein a proportion of the adaptors are hairpin loop adaptors comprising one or more second anchors for coupling the polynucleotide to the membrane and wherein the strength of coupling of the hairpin loop adaptors to the membrane is greater than the strength of coupling of the Y adaptors to the membrane; and a kit for modifying a target polynucleotide comprising (a) a pair of adaptors or a population of adaptors of the invention and (b) a MuA transposase.

(construct 1) helicase-controlled DNA movements (labelled a1) to strand a2 (construct 7b) helicase controlled DNA movements (labelled a2). This was observed to be approximately 35:65 when a single cholesterol was used to couple construct 1 to the membrane in comparison to the single tocopherol used to couple construct 7b to the membrane. This experiment showed that when tocopherol was used to couple construct 7b to the membrane in comparison to a single cholesterol the number of helicase-controlled DNA movements detected showed a bias towards the construct coupled using tocopherol. Therefore, the strength of coupling observed for tocopherol was slightly stronger than that observed for cholesterol.

Figure 11:
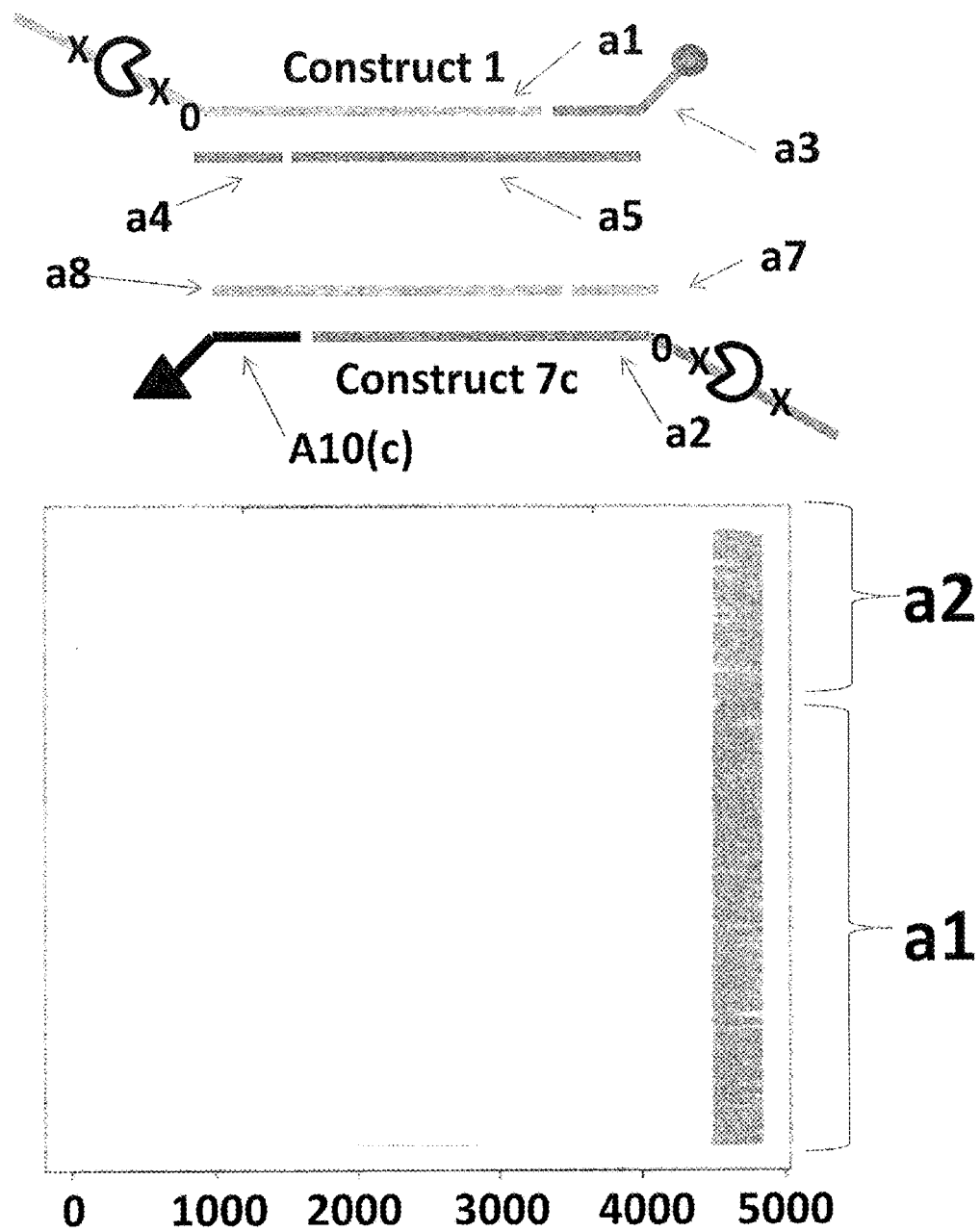

FIG. 11 shows the proportion of helicase-controlled DNA movements detected for construct 1 (coupled to the membrane using a single cholesterol) where strand a1 translocated through the nanopore and construct 7c (coupled to the membrane using a palmitate, shown as a black triangle) where strand a2 translocated through the nanopore. The x-axis shows the position along the lambda DNA sequence to which that the helicase-controlled DNA movements mapped (they were all concentrated in the same region as strands a1 and a2 corresponded to the template and template complement of the region of lambda between 45,042 bp and 48,487 bp). The Y-axis shows the proportion of strand a1 (construct 1) helicase-controlled DNA movements (labelled a1) to strand a2 (construct 7c) helicase controlled DNA movements (labelled a2). This was observed to be approximately 70:30 when a single cholesterol was used to couple construct 1 to the membrane in comparison to the single palmitate used to couple construct 7c to the membrane. This experiment showed that when palmitate was used to couple construct 7c to the membrane, in comparison to a single cholesterol, the number of helicase-controlled DNA movements detected showed a bias towards the construct coupled using cholesterol. Therefore, the strength of coupling observed for palmitate was weaker than that observed for cholesterol.

Figure 12:
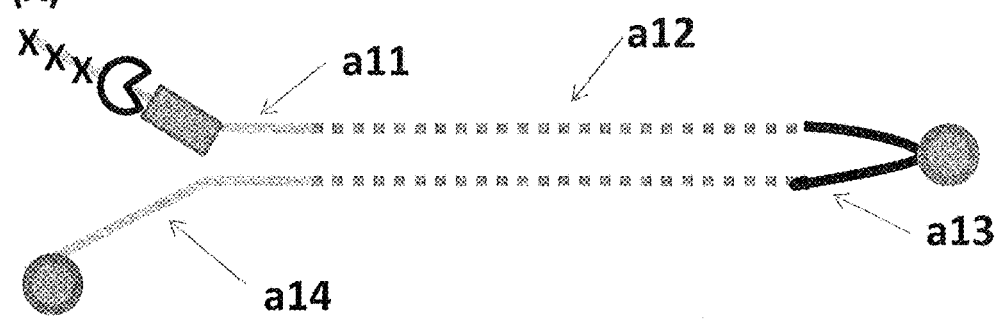
Figure 12:
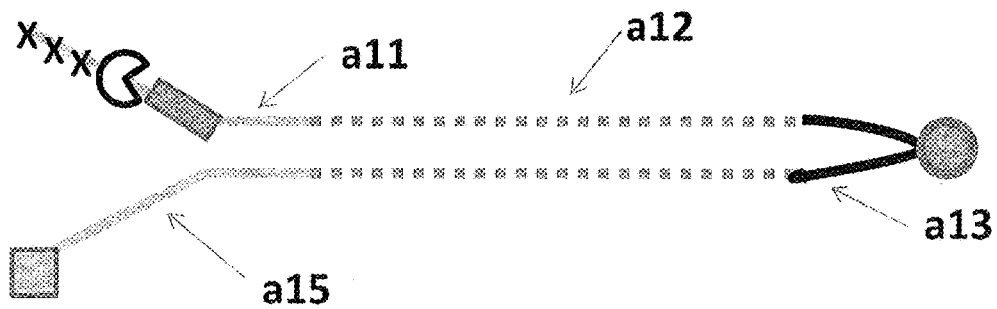

FIG. 12 shows in sections (A) and (B) cartoon representations of the DNA constructs used in Example 6—twenty-five iSpC3 spacers are represented as three black crosses, four iSp18's as a grey rectangle, a cholesterol coupling agent as a grey circle and the palmitate coupling agent as a grey square; labels a11-15 are described in full in Example 5.

Figure 13:
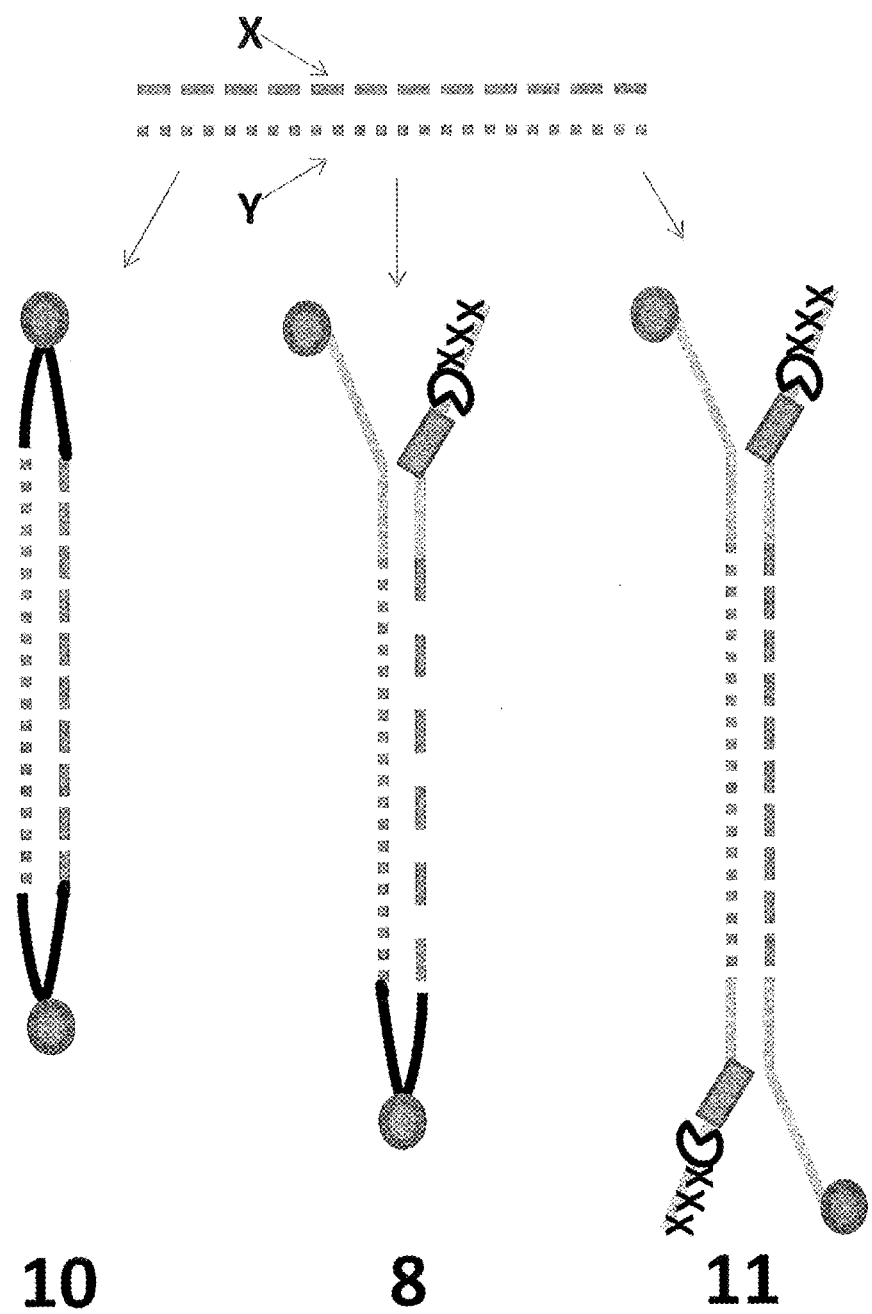

FIG. 13 shows the possible constructs produced (as described in Example 5) after fragmentation and adapter attachment. Construct 10 has two hairpins adapters and cannot be captured by the nanopore. Construct 8 is the desired construct which has one Y-adapter and one hairpin, strands X and Y will both translocate through the nanopore upon capture. Construct 11 has two Y-adapters and, therefore, can capture and translocate only strand X or strand Y.

Figure 14:
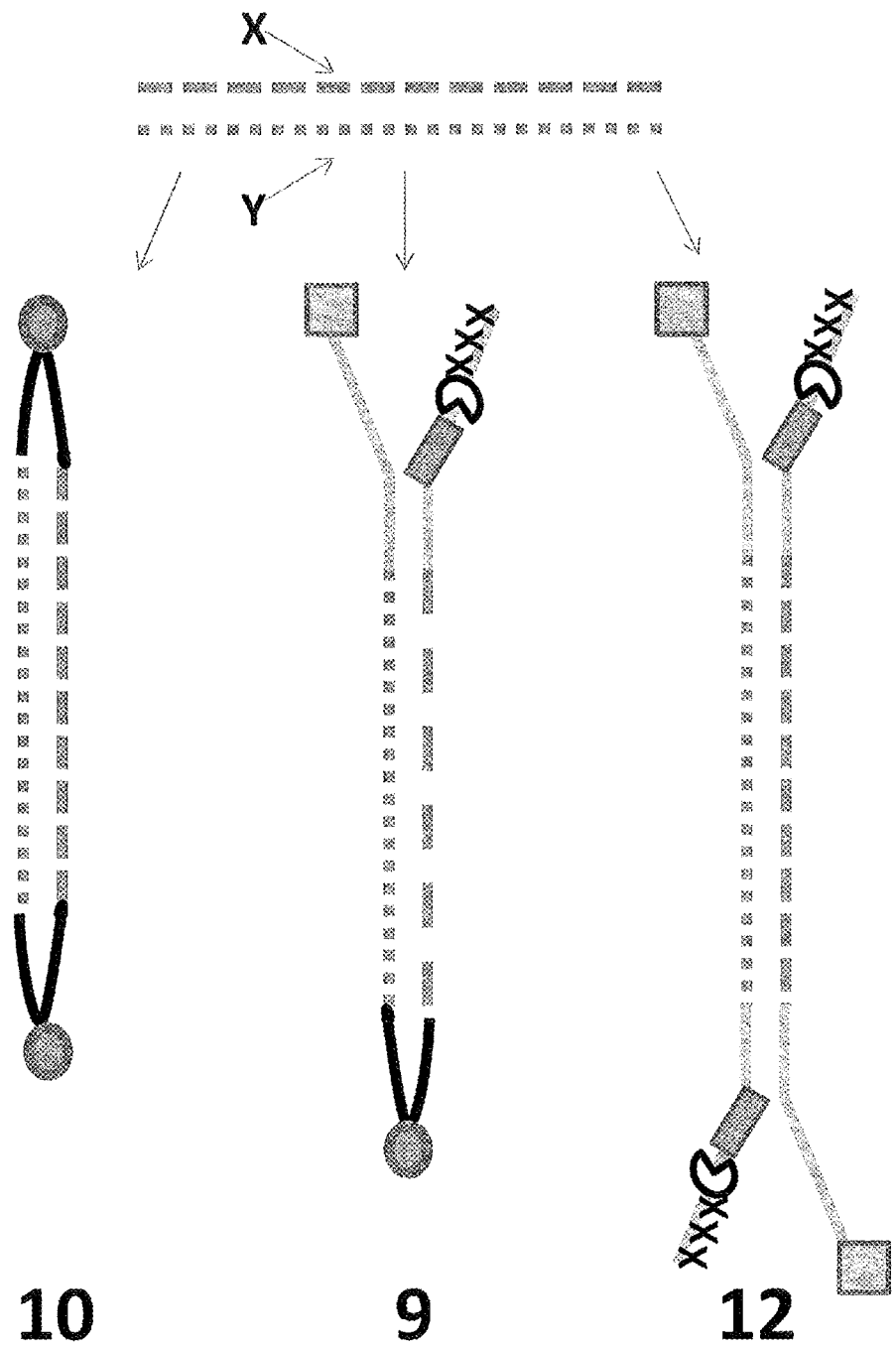

FIG. 14 shows the possible constructs produced (as described in Example 5) after fragmentation and adapter attachment. Construct 10 has two hairpins adapters and cannot be captured by the nanopore. Construct 9 is the desired construct which has one Y-adapter and one hairpin, strands X and Y will both translocate through the nanopore upon capture. Construct 12 has two Y-adapters and, therefore, can capture and translocate only strand X or strand Y.

Figure 15:
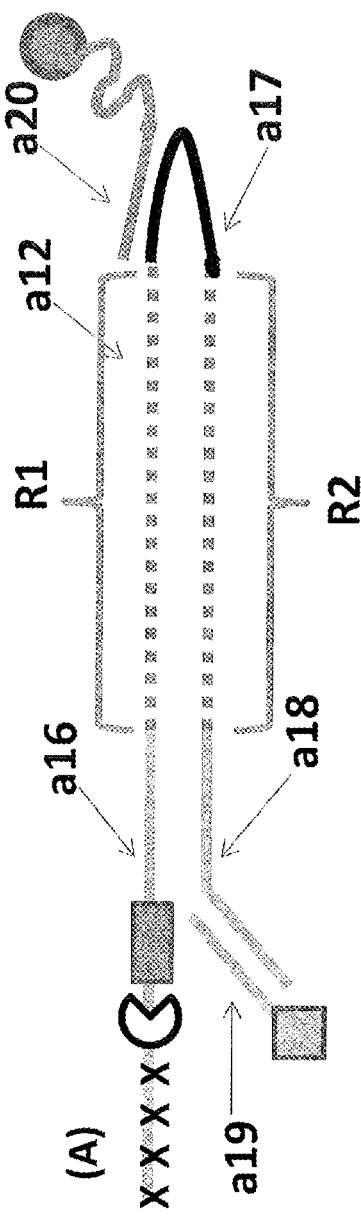
Figure 15:
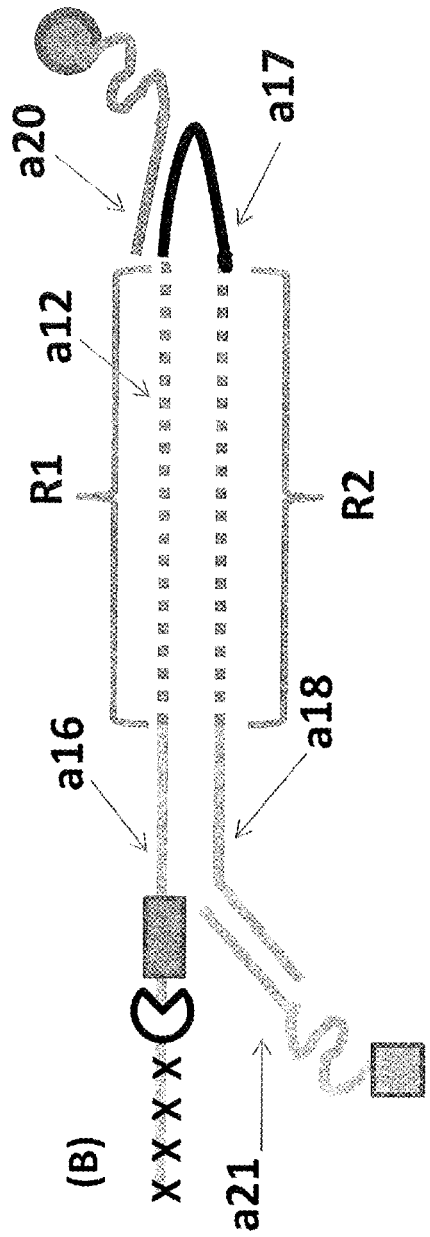

FIG. 15 shows in sections (A) and (B) cartoon representations of two of the DNA constructs (constructs 13 and 14) used in Example 7—thirty iSpC3 spacers are represented as four black crosses, four iSp18's as a grey rectangle, a cholesterol coupling agent as a grey circle and the palmitate coupling agent as a grey square; labels a12, a16-21 are described in full in Example 7. Two regions of the DNA construct are labelled R1 and R2.

Figure 16:
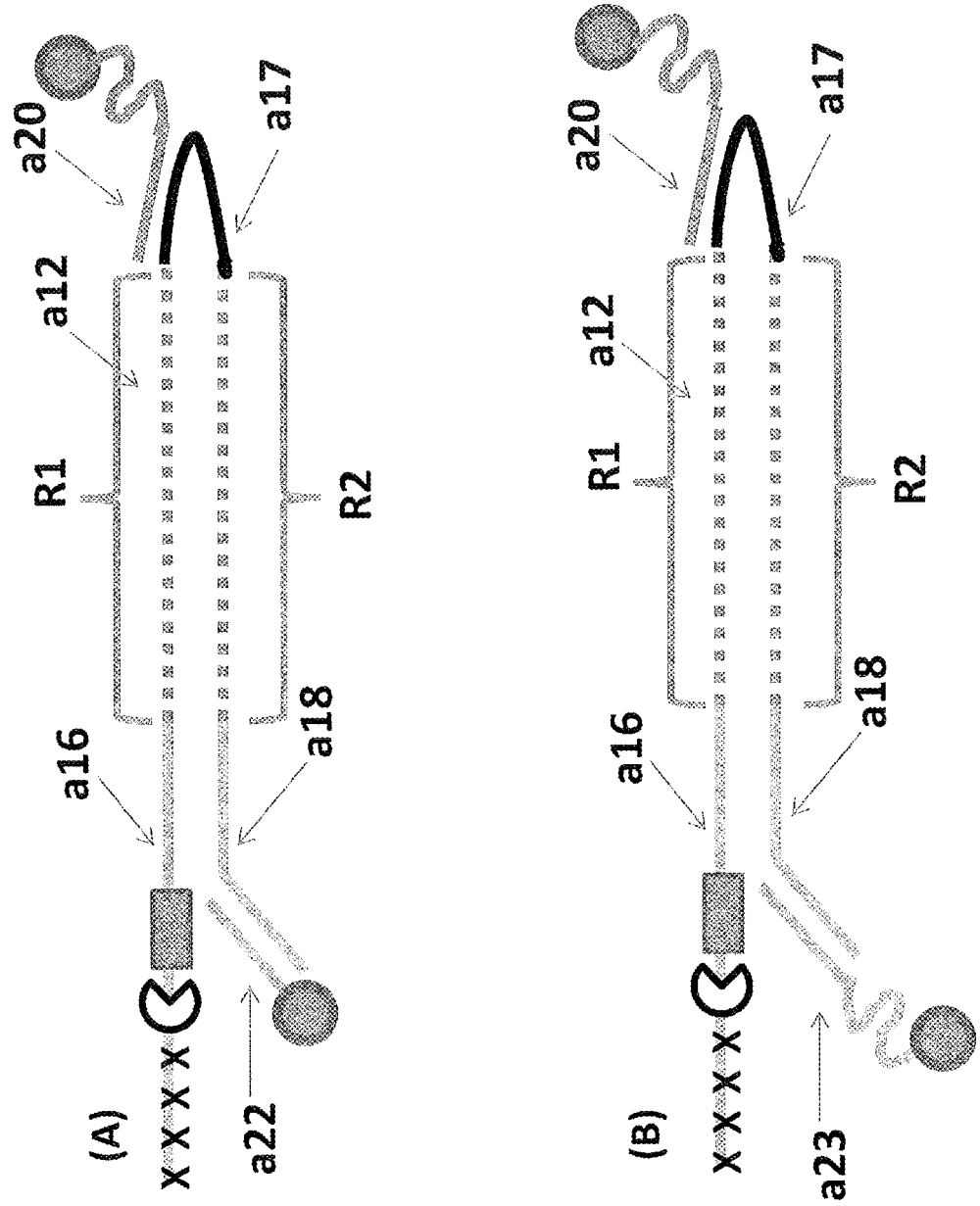

FIG. 16 shows in sections (A) and (B) cartoon representations of two of the DNA constructs (constructs 15 and 16) used in Example 7—thirty iSpC3 spacers are represented as four black crosses, four iSp18's as a grey rectangle, a cholesterol coupling agent as a grey circle labels a12, a16-a18, a20, a22-23 are described in full in Example 7. Two regions of the DNA construct are labelled R1 and R2.

Figure 17:
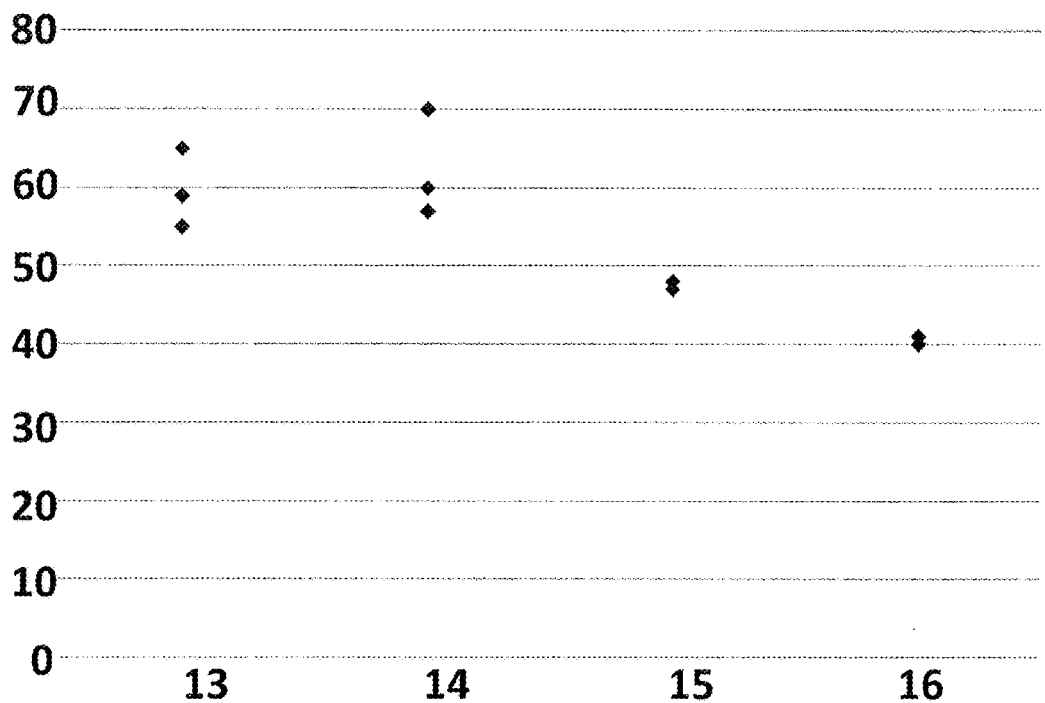

FIG. 17 shows a graph of the % of the helicase-controlled DNA movements detected which corresponded to controlled translocation of both regions R1 and R2 through the nanopore as a proportion of all helicase-controlled DNA movements observed. The y-axis label=percentage (%) and the x-axis label=DNA construct number (13 -16). Each point on the graph corresponds to a separate experiment (n=3).

Figure 18:
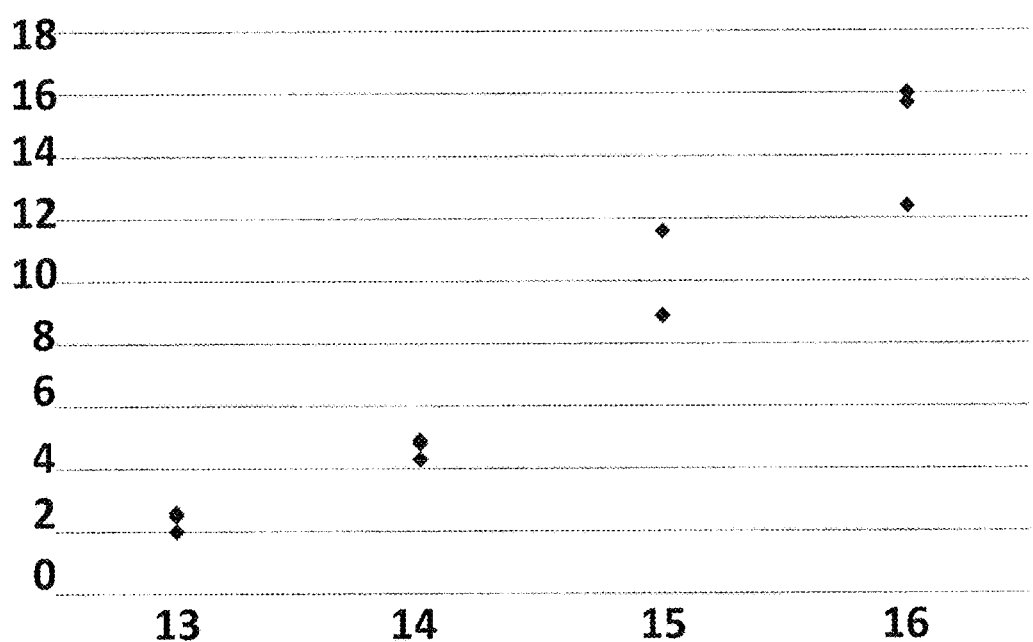

FIG. 18 shows a graph of the number of helicase-controlled DNA movements detected per nanopore for each of the DNA constructs. The y-axis label=helicase-controlled DNA movements per nanopore and the x-axis label=DNA construct number (13-16). Each point on the graph corresponds to a separate experiment (n=3).

DESCRIPTION OF THE SEQUENCE LISTING

SEQ ID NO: 1 shows the codon optimised polynucleotide sequence encoding the MS-B 1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B 1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp).
Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of Tral Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows the polynucleotide sequence of the double stranded portion of a MuA substrate of the invention.

SEQ ID NO: 27 shows the polynucleotide sequence of the double stranded portion of a MuA substrate of the invention. This sequence is complementary to SEQ ID NO: 26 except that it contains a U at the 3' end.

SEQ ID NO: 28 shows polynucleotide sequence of the overhang strand of the double stranded MuA substrate of the invention.

SEQ ID NOs: 29-32 show polynucleotide sequences used in Example 1.

SEQ ID NO: 33-41 show polynucleotide sequences used in Example 1, 2 and 3.

SEQ ID NO: 42 shows a polynucleotide sequence used in Example 4.

SEQ ID NO: 43 shows the polynucleotide sequence of the Enterobacteria phage X. The sequence contains an additional 12 base overhang attached at the 5' end of the template strand. The sequence shown here is that of the template strand only (the template complement is not shown). This sequence is used in Example 5.

SEQ ID NO: 44-48 shows the polynucleotide sequences used in Example 5 and 6.

SEQ ID NO: 49 shows a polynucleotide sequence used in Example 7. At the 5' end the sequence contains a phosphate group.

SEQ ID NO: 50 shows a polynucleotide sequence used in Example 7. At the 3' end the final thymine in the sequence has a phosphothioate group.

SEQ ID NO: 51 shows a polynucleotide sequence used in Example 7.

SEQ ID NO: 52 shows a polynucleotide sequence used in Example 7.

SEQ ID NO: 53 shows a polynucleotide sequence used in Example 7. At the 5' end the sequence contains a phosphate group.

SEQ ID NO: 54 shows a polynucleotide sequence used in Example 7.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "an anchor" refers to two or more anchors, reference to "a helicase" includes two or more helicases, reference to "a transmembrane pore" includes two or more pores and the like.

All publications, patents and patent applications cited herein, whether supra or infra, are hereby incorporated by reference in their entirety.

Characterisation Method of the Invention

When Y adaptors and hairpin loop adaptors are used together to characterise double stranded polynucleotides, the Y adaptor generally comprises the anchor for coupling the polynucleotide to the membrane and a leader sequence which preferentially threads into the pore. The anchor and more importantly the leader typically result in a bias towards the characterisation of double stranded polynucleotides having Y adaptors at both ends.

When a population of double stranded polynucleotides are modified using approximately equal amounts of Y adaptors and hairpin loop adaptors, three distinct groups of modified polynucleotides are produced. Approximately, 50% of the modified polynucleotides have a Y adaptor at one end and a hairpin loop adaptor at the other end (i.e. are "round the corner" or RTC polynucleotides). It is preferred that these RTC polynucleotides are characterised using the method disclosed in WO 2013/014451. Approximately, 25% of the modified polynucleotides have a Y adaptor at each end (i.e. are double Y polynucleotides) and approximately 25% of the modified polynucleotides have a hairpin loop adaptor at each end (i.e. are double hairpin polynucleotides). If the Y adaptor comprises the anchor, there is a bias towards characterisation of the double Y polynucleotides because they have two anchors and therefore couple to the membrane more strongly. If the Y adaptor comprises the leader, there is a bias towards characterisation of the double Y polynucleotides because they have two leaders and therefore preferentially thread into the pore. The presence of the leader generally results in a greater bias than the presence of the anchor. If the Y adaptor comprises both the anchor and the leader, there is the greatest bias towards characterisation of the double Y polynucleotides. The inventors have seen biases of approximately 50-fold towards double Y polynucleotides. The double hairpin polynucleotides are not typically characterised because they do not have a single stranded region capable of threading into the nanopore used for characterisation.

The inventors have shown that using one or more anchors on the hairpin loop adaptor not only reduces characterisation of the double Y polynucleotides, but also reduces the observed throughput of the double Y polynucleotides significantly. The inventors conclude from this that the throughput is dependent on the presence of an anchor at the end of the modified polynucleotide which threads into the nanopore (i.e. the Y adaptor end of a RTC polynucleotide).

The inventors have also surprisingly shown that the bias towards double Y polynucleotides can be overcome by using a Y adaptor and a hairpin loop adaptor which have different strength of coupling to the membrane. If the hairpin loop adaptor couples with more strength than the Y adaptor, a bias towards the RTC polynucleotides is achieved. The "strong" hairpin loop adaptor effectively couples the RTC polynucleotides to the membrane and this allows them to out compete the double Y adaptors which contain two "weaker" tethers. High throughput is maintained for the RTC polynucleotides because of the "weaker" Y adaptor.

The invention concerns characterising a target double stranded polynucleotide using a transmembrane pore in a membrane. The target double stranded polynucleotide is provided with a Y adaptor at one end and a hairpin loop adaptor at the other end. Methods of doing this are discussed in detail below. The Y adaptor comprises one or more first anchors for coupling the polynucleotide to the membrane and the hairpin loop adaptor comprises one or more second anchors for coupling the polynucleotide to the membrane. The strength of coupling of the hairpin loop adaptor to the membrane is greater than the strength of coupling of the Y adaptor to the membrane.

The polynucleotide provided with the two adaptors is contacted with the transmembrane pore such that at least one strand of the polynucleotide moves through the pore. One or more measurements are taken as the at least one strand of the polynucleotide moves with respect to the pore. The measurements are indicative of one or more characteristics of the at least one strand of the polynucleotide.

The invention preferably concerns sequencing or estimating the sequence of a target double stranded polynucleotide. Only part of the target double stranded polynucleotide may be characterised or sequenced as discussed in more detail below.

Target Double Stranded Polynucleotide

The method of the invention characterises a target double stranded polynucleotide. The target double stranded polynucleotide may also be called the template double stranded polynucleotide or the double stranded polynucleotide of interest.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described below. The target polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The target double stranded polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide is preferably a deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP. The nucleotides are most preferably selected from dAMP, dTMP, dGMP, dCMP and dUMP.

The target double stranded polynucleotide preferably comprises the following nucleotides: dAMP, dUMP and/or dTMP, dGMP and dCMP.

A nucleotide may be abasic (i.e. lack a nucleobase). A nucleotide may also lack a nucleobase and a sugar (i.e. is a C3 spacer).

The nucleotides in the target polynucleotide may be attached to each other in any manner. The nucleotides are typically attached by their sugar and phosphate groups as in nucleic acids. The nucleotides may be connected via their nucleobases as in pyrimidine dimers.

The target polynucleotide is double stranded. The target polynucleotide may contain some single stranded regions, but at least a portion of the target polynucleotide is double stranded.

The target polynucleotide can be a nucleic acid, such as deoxyribonucleic acid (DNA) or ribonucleic acid (RNA). The target polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA), bridged nucleic acid (BNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety. Bridged nucleic acids (BNAs) are modified RNA nucleotides. They may also be called constrained or inaccessible RNA. BNA monomers can contain a five-membered, six-membered or even a seven-membered bridged structure with a "fixed" C3'-endo sugar puckering. The bridge is synthetically incorporated at the 2', 4'-position of the ribose to produce a 2', 4'-BNA monomer.

The polynucleotide is most preferably ribonucleic nucleic acid (RNA) or deoxyribonucleic acid (DNA).

The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is typically present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Providing the Polynucleotide with Two Adaptors

The target double stranded polynucleotide is provided with a Y adaptor at one end and a hairpin loop adaptor at the other end. The Y adaptor and/or the hairpin loop adaptor are typically polynucleotide adaptors. They may be formed from any of the polynucleotides discussed above.

The Y adaptor typically comprises a double stranded region and a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail below.

The Y adaptor preferably comprises a leader sequence which preferentially threads into the pore. The leader sequence facilitates the method of the invention. The leader sequence is designed to preferentially thread into the transmembrane pore and thereby facilitate the movement of polynucleotide through the pore. The leader sequence can also be used to link the polynucleotide to the anchor(s) as discussed below.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

Suitable hairpin loop adaptors can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin loop adaptor preferably comprises a selectable binding moiety. This allows the first and/or second polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin loop adaptor and/or the selectable binding moiety may comprise a region that can be cut, nicked, cleaved or hydrolysed. Such a region can be designed to allow the first and/or second polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The Y adaptor and/or the hairpin loop adaptor may be ligated to the polynucleotide using any method known in the art. One or both of the adaptors may be ligated using a ligase, such as T4 DNA ligase, *E. coli* DNA ligase, Taq DNA ligase, Tma DNA ligase and 9° N DNA ligase. Alternatively, the adaptors may be added to the polynucleotide using the methods of the invention discussed below.

In a preferred embodiment, step a) of the method comprises modifying the target double stranded polynucleotide so that it comprises the Y adaptor at one end and the hairpin loop adaptor at the other end. Any manner of modification can be used. The method preferably comprises modifying the target double stranded polynucleotide in accordance with the invention. This is discussed in more detail below. The methods of modification and characterisation may be combined in any way.

Membrane

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

In a preferred embodiment, the invention provides a method of characterising a target double stranded polynucleotide using a transmembrane pore in a membrane comprising a triblock copolymer, optionally wherein the membrane is modified to facilitate the coupling.

The membrane is most preferably one of the membranes disclosed in International Application No. PCT/GB2013/052766 or PCT/GB2013/052767.

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s$^{-1}$. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in W02009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In another preferred embodiment, the membrane is a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Coupling

The polynucleotide may be coupled to the membrane using any known method. The polynucleotide is coupled to the membrane using at least two anchors.

The Y adaptor comprises one or more first anchors. The hairpin loop adaptor comprises one or more second adaptors. Each anchor comprises a group which couples (or binds) to the adaptor and a group which couples (or binds) to the membrane. Each anchor may covalently couple (or bind) to the adaptor and/or the membrane.

The Y adaptor may contain any number of first anchors, such as 2, 3, 4 or more anchors. The hairpin loop adaptor may contain any number of second anchors, such as 2, 3, 4 or more anchors. For instance, one or both adaptors may comprise two anchors each of which separately couples (or binds) to both the adaptor(s) and membrane.

The one or more first anchors and/or the one or more second anchors may comprise one or more polynucleotide binding proteins. Each anchor may comprise one or more polynucleotide binding proteins. The polynucleotide binding protein(s) may be any of those discussed above.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the detector.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalized, for example at least 0.01%, at least 0.1%, at least 1%, at least 10%, at least 25%, at least 50% or 100%.

The Y adaptor and/or the hairpin loop adaptor may be coupled directly to the membrane. The one or more first anchors and/or the one or more second anchors preferably comprise a linker. The one or more first anchors and/or the one or more second anchors may comprise one or more, such as 2, 3, 4 or more, linkers. One linker may be used to couple more than one, such as 2, 3, 4 or more, polynucleotides or adaptors to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide to be characterised may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane or may be used to couple (or bind) to the polynucleotide. This is discussed in more detail below. Crosslinkage of polynucleotides can be avoided using a "lock and key" arrangement.

Only one end of each linker may react together to form a longer linker and the other ends of the linker each react with the polynucleotide or membrane respectively. Such linkers are described in International Application No. PCT/GB10/000132 (published as WO 2010/086602).

The use of a linker is preferred in the sequencing embodiments discussed below. If a polynucleotide is permanently coupled directly to the membrane in the sense that it does not uncouple when interacting with the pore, then some sequence data will be lost as the sequencing run cannot continue to the end of the polynucleotide due to the distance between the membrane and the detector. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 1 below.

TABLE 1

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase."*Anal Biochem* 169(2): 376-82). *Streptavidin*/biotin and/or streptavidin/desthiobiotin coupling may be used for polynucleotide. It may also be possible that anchors may be directly added to polynucleotides using terminal transferase with suitably modified nucleotides (e.g. cholesterol or palmitate).

The one or more first anchors and/or the one or more second anchors preferably couple the target double stranded polynucleotide to the membrane via hybridisation. The hybridisation may be present in any part of the one or more anchors, such as between the one or more anchors and the polynucleotide, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. The one or more first anchors and/or the one or more second anchors may hybridise to the target double stranded polynucleotide. The one or more first anchors may hybridise directly to the target double stranded polynucleotide or directly to the Y adaptor and/or leader sequence. The one or more second anchors may hybridise directly to the target double stranded polynucleotide or directly to the hairpin adaptor. Alternatively, the one or more first anchors may be hybridised to one or more, such as 2 or 3, intermediate polynucleotides (or "splints") which are hybridised to the target double stranded polynucleotide or to the Y adaptor and/or leader sequence. Alternatively, the one or more second anchors may be hybridised to one or more, such as 2 or 3, intermediate polynucleotides (or "splints") which are hybridised to the target double stranded polynucleotide or to the hairpin loop adaptor. The hybridisation of the one or more anchors to one or more splints may form one or more rigid double stranded polynucleotide linkers as discussed in more detail below.

The one or more first anchors and/or the one or more second anchors may comprise a single stranded or double stranded polynucleotide. One part of the anchor may be ligated to the double stranded polynucleotide. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci U S A 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the a double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the target and added polynucleotides respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the adaptors and anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible.

It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting dATP in the reaction for a modified nucleotide triphosphate then anchors, such as cholesterol, thiol, amine, azide, biotin or lipid, can be incorporated into double stranded polynucleotides. Therefore, each copy of the amplified polynucleotide will contain an anchor.

The anchor can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable polynucleotide binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more first anchors and/or the one or more second anchors can comprise any group which binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalized.

Where the one or more first anchors and/or the one or more second anchors comprise a protein, it may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

In another aspect the Y adaptor and/or the hairpin loop adaptor may be functionalised, using methods described above, so that it/they can be recognised by a specific binding group. Specifically the adaptor(s) may be functionalised with a ligand such as biotin (for binding to streptavidin), amylose (for binding to maltose binding protein or a fusion protein), Ni-NTA (for binding to poly-histidine or poly-histidine tagged proteins) or peptides (such as an antigen).

An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Strength of Coupling

The strength of coupling (or binding) of the hairpin loop adaptor to the membrane is greater than the strength of coupling (or binding) of the Y adaptor to the membrane. This can be measured in any way. A suitable method for measuring the strength of coupling (or binding) is disclosed in the Examples.

The strength of coupling (or binding) of the hairpin loop adaptor is preferably at least 1.5 times the strength of coupling (or binding) of the Y-adaptor, such as at least twice, at least three times, at least four times, at least five or at least ten times the strength of coupling (or binding) of the Y-adaptor. The affinity constant (Kd) of the hairpin loop adaptor for the membrane is preferably at least 1.5 times the affinity constant of the Y adaptor, such as at least twice, at least three times, at least four times, at least five or at least ten times the strength of coupling of the Y adaptor.

There are several ways in which the hairpin loop adaptor couples (or binds) more strongly to the membrane than the Y adaptor. For instance, the hairpin loop adaptor may comprise more anchors than the Y adaptor. For instance, the hairpin loop adaptor may comprise 2, 3 or more second anchors whereas the Y adaptor may comprise one first anchor. The strength of coupling (or binding) of the one or more second anchors to the membrane may be greater than the strength of coupling (or binding) of the one or more first anchors to the membrane. The strength of coupling (or binding) of the one or more second anchors to the hairpin loop adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used in the invention. Strength of coupling (or binding) may be measure using known techniques in the art.

The one or more second anchors preferably comprise one or more groups which couples(s) (or bind(s)) to the membrane with a greater strength than the one or more groups in the one or more first anchors which couple(s) (or bind(s)) to the membrane. In preferred embodiments, the hairpin loop adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the hairpin loop adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine. Other factors which may affect the ability of the one or more groups to couple (or bind) to the membrane include, but are not limited to, the charge or hydrophobicity of the one or more anchors or one or more linkers or the entropic cost. For instance, the one or more first and second anchors may comprise cholesterol, but the charge of the one or more second anchors may increase the ability of their cholesterol to couple (or bind) to the membrane or the charge of the one or more first anchors may decrease the ability of their cholesterol to couple (or bind) to the membrane.

The one or more first anchors may comprise one or more rigid linkers and the one or more second anchors may comprise one or more flexible linkers. Flexible linkers may allow the one or more groups which couple (or bind) to the membrane to move relative to the target double stranded polynucleotide and thereby increase the likelihood of coupling. In this embodiment, the one or more groups which couple (or bind) to the membrane may be the same in the first and second anchors. For instance, the one or more first anchors may comprise one or more rigid linkers and cholesterol and the one or more second anchors may comprise one or more flexible linkers and cholesterol. Suitable linkers are discussed above. Rigid linkers are those which do not substantially bend or flex and do not allow substantial rotation either along their length or at their attachments points. Rigid linkers are those which do not permit substantial movement of the one or more groups which couple (or bind) to the membrane relative to the target double stranded polynucleotide. In the case where a rigid linker comprises a polymeric or oligomeric section, the polymeric or oligomeric section is shorter than the persistence length, a measure of rigidity, of the corresponding polymer or oligomer. Persistence length can be measured or calculated using methods known in the art. For instance, the persistence length of double-stranded DNA is approximately 50 nm or 500 Angstroms or 147 nucleotide pairs. A stretch of double-stranded DNA of DNA less than 147 nucleotide pairs in length is considered to be rigid. Rigid linkers include, but are not limited to, those comprising double stranded polynucleotides, including DNA, conjugated organic moieties or organic moieties with bulky side chains that restrict conformational freedom. The one or more rigid linkers preferably comprise one or more double stranded polynucleotides. Any of the polynucleotides discussed above may be used. The preferred length of the one or more rigid linkers is 5, 10, 15, 20, 25, 27, 30, 35, 40 or more nucleotide pairs.

Flexible linkers are those which substantially bend or flex or rotate. Flexible linkers may bend or flex along their length or at one or both of their attachment points. Flexible linkers permit substantial movement of the one or more groups which couple (or bind) to the membrane relative to the target double stranded polynucleotide. Flexible linkers are those which permit substantial variation of the orientation of the target double stranded polynucleotide. Flexible linkers may allow movement of the one or more groups by flexing in one or two dimensions. Alternatively or in addition, flexible linkers may allow movement of the one or more groups that is a rotation about an axis. In the case where a flexible linker comprises a polymeric or oligomeric section, the polymeric or oligomeric section contributes significant flexibility if it is similar to or longer than the persistence length of the corresponding polymer or oligomer. Flexible linkers include, but are not limited to, those comprising a single-stranded oligonucleotide or polynucleotide, a short carbon spacer (e.g. alkanes and alkenes), a polypeptide, a polyhistidine tag, nucleoside derivatives, a short polysaccharide or combinations thereof. Flexible linkers typically also allow rotation of the one or more groups which couple (or bind) to the membrane. Flexible linkers may permit rotation in at least one axis. The axis is preferably the longitudinal axis of the linker. The one or more flexible linkers preferably comprise one or more spacer 9 (iSp9) groups or one or more spacer 18 (iSp18) groups. The one or more flexible linkers preferably comprise 1, 2, 3, 4, 5, 6, 7, 8, 9, 10 or more spacer 9 (iSp9) groups and/or 1, 2, 3, 4, 5, 6, 7, 8, 9, 10 or more spacer 18 (iSp18) groups. Preferably (a) the hairpin loop adaptor comprises more anchors than the Y adaptor, (b) the strength of coupling of one or more second anchors to the membrane is greater than the strength of coupling of the one or more first anchors to the membrane, (c) the strength of coupling of the one or more second anchors to the hairpin loop adaptor is greater than the strength of coupling of the one or more first anchors to the Y adaptor, (d) the one or more first anchors and one or more second anchors couple their respective adaptors to the membrane via hybridisation and the strength of hybridisation is greater in the one or more second anchors than in the one or more first anchors, (e) the one or more first anchors comprise one or more rigid linkers and the one or more second anchors comprise one or more flexible linkers or (f) any combination of (a) to (e). In other words, the invention preferably comprises a combination of (a) and (b), a combination of (b) and (c), a combination of (c) and (d), a combination (a) and (c), a combination of (b) and (d), a combination of (a) and (d), a combination of (a) and (e), a combination of (b) and (e), a combination of (c) and (e), a combination of (d) and (e), a combination of (a), (b) and (c), a combination of (b), (c) and (d), a combination of (a), (b) and (d), a combination of (a), (c) and (d), a combination of (a), (b) and (e), a combination of (a), (c) and (e), a combination of (a), (d) and (e), a combination of (b), (c) and (e), a combination of (b), (d) and (e), a combination of (c), (d) and (e), a combination of (a), (b), (c) and (d), a combination of (a), (b), (c) and (e), a combination of (a), (b), (d) and (e), a combination of (a), (c), (d) and (e), a combination of (b), (c), (d) and (e) or a combination of (a), (b), (c), (d) and (e).

Transmembrane Pore

The method comprises taking one or more measurements as at least one strand of the polynucleotide moves with respect to the transmembrane pore. A variety of different types of measurements may be made using the pore. This includes without limitation: electrical measurements and optical measurements. Possible electrical measurements include: current measurements, impedance measurements, tunnelling measurements (Ivanov AP et al., Nano Lett. 2011 Jan. 12;11(1): 279-85), and FET measurements (International Application WO 2005/124888). Optical measurements may be combined with electrical measurements (Soni GV et al., Rev Sci Instrum. 2010 January;81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12;106(19): 7702-7, Lieberman KR et al, J Am Chem Soc. 2010;132(50): 17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27): 8650-5. In some instances, the current passing through the detector (or pore) as a polynucleotide moves with respect to the pore is used to estimate or determine the sequence of the polynucleotide. This is strand sequencing.

The method comprises contacting the polynucleotide with a transmembrane pore. A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Step (c) preferably comprises taking one or more measurements of the current passing through the pore as the at least one strand moves with respect to the pore wherein the one or more current measurements are indicative of one or more characteristics of the at least one strand.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as an analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 3, at least 4, at least 5, at least 6, at least 7, at least 8, at least 9, at least 10, at least 11, at least 12, at least 13 or at least 14 subunits, such as 3, 4, 5, 6, 7, 8, 9, 10, 11, 12, 13 or 14 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, lysenin, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215: 403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, DβG, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its a-helices and/or loop regions.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Polynucleotide Characterisation

The method of the invention involves measuring one or more characteristics of the target double stranded polynucleotide.

Any number of polynucleotides can be investigated. For instance, the method of the invention may concern characterising 2, 3, 4, 5, 6, 7, 8, 9, 10, 20, 30, 50, 100 or more polynucleotides.

The polynucleotides can be naturally occurring or artificial. For instance, the method may be used to verify the sequence of two or more manufactured oligonucleotides. The methods are typically carried out in vitro.

The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12;106(19): 7702-7, Lieberman K R et al, J Am Chem Soc. 2010;132(50): 17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric ac across the membrane. The type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Step (b) preferably comprises contacting the polynucleotide provided in step a) with a polynucleotide binding protein such that the protein controls the movement of the at least one strand of the polynucleotide through the pore.

More preferably, the method comprises b) contacting the polynucleotide provided in step a) with a transmembrane pore and a polynucleotide binding protein such that at least one strand of the polynucleotide moves through the pore and the protein controls the movement of the at least one strand of the polynucleotide through the pore; and c) measuring the current passing through the pore as the at least one strand of the polynucleotide moves with respect to the pore wherein the current is indicative of one or more characteristics of the at least one strand of the polynucleotide and thereby characterising the double stranded target polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: β), RecJ from *T. thermophilus* (SEQ ID NO: 15) and bacteriophage lambda exonuclease (SEQ ID NO: 17) and variants thereof. Three subunits comprising the sequence shown in SEQ ID NO: 15 or a variant thereof interact to form a trimer exonuclease. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Mhu (SEQ ID NO: 21), TraI Eco (SEQ ID NO: 22), XPD Mbu (SEQ ID NO: 23) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736.

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24

(Dda) or a variant thereof. Variants may differ from the native sequences in any of the ways discussed below for transmembrane pores. A preferred variant of SEQ ID NO: 24 comprises E94C/A360C and then (ΔM1)G1G2 (i.e. deletion of M1 and then addition G1 and G2) or E94C/A360C/C109A/C136A and then (ΔM1)G1G2.

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the target double stranded polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes.

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Helicase(s) and Molecular Brake(s)

In a preferred embodiment, the invention provides a method of controlling the movement of a double stranded polynucleotide through a transmembrane pore, comprising:

(a) providing the double stranded polynucleotide with a Y adaptor at one end and a hairpin loop adaptor at the other end, wherein the Y adaptor comprises the one or more helicases and one or more first anchors for coupling the polynucleotide to the membrane, wherein the hairpin loop adaptor comprises the one or more molecular brakes and one or more second anchors for coupling the polynucleotide to the membrane and wherein the strength of coupling of the hairpin loop adaptor to the membrane is greater than the strength of coupling of the Y adaptor to the membrane;

(b) contacting the target polynucleotide provided in step (a) with the pore; and (c) applying a potential across the pore such that the one or more helicases and the one or more molecular brakes are brought together and both control the movement of the target polynucleotide through the pore.

This type of method is discussed in detail in the International Application PCT/GB2014/052737.

The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 8) which act as molecular brakes are disclosed in U.S. Pat. No. 5,576,204. The one or more molecular brakes are preferably derived from a helicase.

Spacers in the Y Adaptor

The one or more helicases attached to the Y adaptor may be stalled at one or more spacers as discussed in International Application No. PCT/GB2014/050175 (published as WO 2014/135838). Any configuration of one or more helicases and one or more spacers disclosed in the International Application may be used in this invention.

RTC Sequencing In a preferred embodiment, step b) comprises contacting the polynucleotide provided in step a) with a transmembrane pore such that both strands of the polynucleotide move through the pore and step c) comprises taking one or more measurements as the both strands of the polynucleotide move with respect to the pore wherein the measurements are indicative of one or more characteristics of the strands of the polynucleotide and thereby characterising the target polynucleotide. Any of the embodiments discussed above equally apply to this embodiment.

Uncoupling

The method of the invention may involve characterising multiple target double stranded polynucleotides and uncoupling of the first target double stranded polynucleotide.

In a preferred embodiment, the invention involves characterising two or more target double stranded polynucleotides. The method preferably comprises:

(a) providing a first target double stranded polynucleotide in a first sample with a first Y adaptor at one end and a first hairpin loop adaptor at the other end, wherein the first Y adaptor comprises one or more first anchors for coupling the polynucleotide to the membrane, wherein the first hairpin loop adaptor comprises one or more second anchors for coupling the polynucleotide to the membrane and wherein the strength of coupling of the first hairpin loop adaptor to the membrane is greater than the strength of coupling of the first Y adaptor to the membrane;

(b) providing a second target double stranded polynucleotide in a second sample with a second Y adaptor at one end and a second hairpin loop adaptor at the other end, wherein the second Y adaptor comprises one or more third anchors for coupling the polynucleotide to the membrane, wherein the second hairpin loop adaptor comprises one or more fourth anchors for coupling the polynucleotide to the membrane and wherein the strength of coupling of the second hairpin loop adaptor to the membrane is greater than the strength of coupling of the second Y adaptor to the membrane;

(c) coupling the first polynucleotide provided in step (a) to a membrane;

(d) contacting the first polynucleotide coupled in step (c) with a transmembrane pore such that at least one strand of the first polynucleotide moves through the pore;

(e) taking one or more measurements as the at least one strand of the first polynucleotide moves with respect to the pore wherein the measurements are indicative of one or more characteristics of the at least one strand of the first polynucleotide and thereby characterising the first polynucleotide;

(f) uncoupling the first polynucleotide from the membrane;

(g) coupling the second polynucleotide provided in step (b) to the membrane;

(h) contacting the second polynucleotide coupled in step (g) with a transmembrane pore such that at least one strand of the second polynucleotide moves through the pore; and (i) taking one or more measurements as the at least one strand of the second polynucleotide moves with respect to the pore wherein the measurements are indicative of one or more characteristics of the at least one strand of the second polynucleotide and thereby characterising the first polynucleotide.

This type of method is discussed in detail in the UK Application 1406155.0 and in the International application being filed concurrently with this application (ONT IP 055). Any of the embodiments discussed therein are applicable to this method.

Step (f) (i.e. uncoupling of the first polynucleotide) may be performed before step (g) (i.e. before coupling the second polynucleotide to the membrane). Step (g) may be performed before step (f). If the second polynucleotide is coupled to the membrane before the first polynucleotide is uncoupled, step (f) preferably comprises selectively uncoupling the first polynucleotide from the membrane (i.e. uncoupling the first polynucleotide but not the second polynucleotide from the membrane). A skilled person can design a system in which selective uncoupling is achieved. Steps (f) and (g) may be performed at the same time. This is discussed in more detail below.

Removal or Washing

Although the first polynucleotide is uncoupled from the membrane in step (f), it is not necessarily removed or washed away. If the second polynucleotide can be easily distinguished from the first polynucleotide, there is no need to remove the first polynucleotide.

Between steps (f) and (g), the method preferably further comprises removing at least some of the first sample from the membrane. At least 10% of the first sample may be removed, such as at least 20%, at least 30%, at least 40%, at least 50%, at least 60%, at least 70%, at least 80% or at least 90% of the first sample may be removed.

The method more preferably further comprises removing all of the first sample from the membrane. This can be done in any way. For instance, the membrane can be washed with a buffer after the first polynucleotide has been uncoupled. Suitable buffers are discussed below.

Modified Target Double Stranded Polynucleotide

Before step a), a target double stranded polynucleotide may be contacted with a polymerase and a population of free nucleotides under conditions in which the polymerase forms a modified target double stranded polynucleotide using the target double stranded polynucleotide as a template, wherein the polymerase replaces one or more of the nucleotide species in the target polynucleotide with a different nucleotide species when forming the modified polynucleotide. The modified target double stranded polynucleotide may then be provided as in step a). This type of modification is described in the International Application No. PCT/GB2015/050483. Any of the polymerases discussed above may be used. The polymerase is preferably Klenow or 9° North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 9° North. A primer or a 3' hairpin is typically used as the nucleation point for polymerase extension.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the target polynucleotide with different nucleotide species in the modified nucleotide, the modified polynucleotide contains k-mers which differ from those in the target polynucleotide. The different k-mers in the modified polynucleotide are capable of producing different current measurements from the k-mers in the target polynucleotide and so the modified polynucleotide provides different information from the target polynucleotide. The additional information from the modified polynucleotide can make it easier to characterise the target polynucleotide. In some instances, the modified polynucleotide itself may be easier to characterise. For instance, the modified polynucleotide may be designed to include k-mers with an increased separation or a clear separation between their current measurements or k-mers which have a decreased noise.

Other Characterisation Method

In another embodiment, the polynucleotide is characterised by detecting labelled species that are released as a polymerase incorporates nucleotides into the polynucleotide. The polymerase uses the polynucleotide as a target. Each labelled species is specific for each nucleotide. In step a) the target double stranded polynucleotide is provided as discussed above. In step b), the polynucleotide provided in step a) is contacted with the transmembrane pore, a polymerase and labelled nucleotides such that phosphate labelled species are sequentially released when nucleotides are added to the polynucleotide by the polymerase, wherein the phosphate species contain a label specific for each nucleotide. The polymerase may be any of those discussed above. In step c), the phosphate labelled species are detected using the pore and thereby characterising the double stranded target polynucleotide. Steps b) and c) are disclosed in European Application No. 13187149.3 (published as EP 2682460). Any of the embodiments discussed above equally apply to this method.

Modification Methods of the Invention

The invention also provides methods of producing the modified target polynucleotide provided in step a) of the characterisation method.

The invention provides a method for modifying a target double stranded polynucleotide for characterisation using a transmembrane pore in a membrane. The method involves ligating a Y adaptor to one end of the polynucleotide and ligating a hairpin loop adaptor to the other end of the polynucleotide. As above, the Y adaptor comprises one or more first anchors for coupling the polynucleotide to the membrane, the hairpin loop adaptor comprises one or more second anchors for coupling the polynucleotide to the membrane and the strength of coupling of the hairpin loop adaptor to the membrane is greater than the strength of coupling of the Y adaptor to the membrane.

The invention provides an alternative method in which the anchors are attached to the adaptors after the adaptors have been ligated to the target double stranded polynucleotide. The method involves ligating a Y adaptor to one end of the polynucleotide and ligating a hairpin loop adaptor to the other end of the polynucleotide. One or more first anchors are then attached to the Y adaptor and one or more second anchors are attached to the hairpin loop adaptor. As above, the strength of coupling of the hairpin loop adaptor to the membrane is greater than the strength of coupling of the Y adaptor to the membrane. The one or more anchors may be attached to the adaptor is any way, including any of those discussed above. The one or more anchors are preferably attached to the adaptor via hybridisation.

Any methods of ligation may be used. Suitable methods are disclosed above.

The Y adaptor and hairpin loop adaptor may be any of those discussed above.

MuA-Based Methods

The invention also provides a method for modifying a target double stranded polynucleotide for characterisation using a transmembrane pore in a membrane, comprising contacting the target polynucleotide with a MuA transposase and a population of double stranded MuA substrates, wherein a proportion of the substrates in the population are Y adaptors comprising one or more first anchors for coupling the polynucleotide to the membrane, wherein a proportion of the substrates in the population are hairpin loop adaptors comprising one or more second anchors for coupling the polynucleotide to the membrane and wherein the strength of coupling of the hairpin loop adaptor to the membrane is greater than the strength of coupling of the Y adaptor to the membrane, and thereby producing a plurality of modified double stranded polynucleotides.

The invention provides an alternative method in which the anchors are attached to the substrates after the target double stranded polynucleotide has been fragmented by the MuA transposase and the substrates have been ligated to the fragments. The method involves contacting the target polynucleotide with a MuA transposase and a population of double stranded MuA substrates, wherein a proportion of the substrates in the population are Y adaptors and wherein a proportion of the substrates in the population are hairpin loop adaptors. The transposase fragments the target polynucleotide and ligates a substrate to one or both ends of the double stranded fragments and thereby produces a plurality of fragment/substrate constructs. The transposase preferably fragments the target polynucleotide and ligates a substrate to both ends of the double stranded fragments and thereby produces a plurality of fragment/substrate constructs. The transposase preferably produces a plurality of fragment/substrate constructs each comprising a Y adaptor at one end and a hairpin loop adaptor at the other end. The method also involves attaching to the Y adaptors in the plurality of fragment/substrate constructs one or more first anchors and attaching to the hairpin loop adaptors in the plurality of fragment/substrate constructs one or more second anchors and thereby producing a plurality of modified double stranded polynucleotides. The strength of coupling of each hairpin loop adaptor to the membrane is greater than the strength of coupling of each Y adaptor to the membrane.

The Y adaptor and hairpin loop adaptor may be any of those discussed above.

MuA-based fragmentation a target double stranded polynucleotide is disclosed in International Application No. PCT/GB2014/052505 (published as WO 2015/022544).

The target polynucleotide is contacted with a MuA transposase. This contacting occurs under conditions which allow the transposase to function, i.e. to fragment the target polynucleotide and to ligate MuA substrates to the one or both ends of the fragments. MuA transposase is commercially available, for instance from Thermo Scientific (Catalogue Number F-750C, 20 μL (1.1 μg/μL)). Conditions under which MuA transposase will function are known in the art.

The target polynucleotide is contacted with a population of double stranded MuA substrates. The double stranded substrates are polynucleotide substrates and may be formed from any of the nucleotides, polynucleotides or nucleic acids discussed above.

Each substrate typically comprises a double stranded portion which provides its activity as a substrate for MuA transposase. The double stranded portion is typically the same in each substrate. The population of substrates may comprise different double stranded portions. Each substrate preferably comprises a double stranded portion which comprises the sequence shown in SEQ ID NO: 26 hybridised to a sequence which is complementary to the sequence shown in SEQ ID NO: 26. The at least one overhang is preferably at the 5' end of the sequence which is complementary to the sequence shown in SEQ ID NO: 26.

In a preferred embodiment, each substrate in the population comprises at least one overhang of universal nucleotides such that the transposase fragments the target polynucleotide and ligates a substrate to one or both ends, preferably both ends, of the double stranded fragments and thereby produces a plurality of fragment/substrate constructs and wherein the method further comprises ligating the overhangs to the fragments in the constructs and thereby producing a plurality of modified double stranded polynucleotides. The transposase preferably produces a plurality of fragment/substrate constructs each comprising a Y adaptor at one end and a hairpin loop adaptor at the other end.

Each substrate preferably comprises only one overhang. The only one overhang is preferably at the 5' end of one strand of the double stranded portion.

The overhang may be at least 3, at least 4, at least 5, at least 6 or at least 7 nucleotides in length. The overhang is preferably 5 nucleotides in length.

A universal nucleotide is one which will hybridise to some degree to all of the nucleotides in the target polynucleotide. Suitable universal nucleotides are described in International Application No. PCT/GB2014/052505 (published as WO 2015/022544).

The overhang(s) of universal nucleotides may further comprise a reactive group, preferably at the 5' end. The reactive group may be used to ligate the overhangs to the fragments in the constructs as discussed below. The reactive group may be used to ligate the fragments to the overhangs using click chemistry. Suitable reactive groups are disclosed in International Application No. PCT/GB2014/052505 (published as WO 2015/022544).

In a further embodiment, the modification method uses a MuA transposase and a population of MuA substrates each comprising at least one overhang comprising a reactive group. The overhang(s) may be any length and may comprise any combination of any nucleotide(s). Suitable lengths and nucleotides are disclosed above. Suitable reactive groups are discussed above.

In another embodiment, the method comprises contacting the target polynucleotide with a population of double stranded MuA substrates each comprising (i) at least one overhang and (ii) at least one nucleotide in the same strand as the at least one overhang which comprises a nucleoside that is not present in the target polynucleotide such that the transposase fragments the target polynucleotide and ligates a substrate to one or both ends of the double stranded fragments and thereby produces a plurality of fragment/substrate constructs. A skilled person can identify nucleosides not present in the target polynucleotide as described in International Application No. PCT/GB2014/052505 (published as WO 2015/022544). The transposase preferably fragments the target polynucleotide and ligates a substrate to both ends of the double stranded fragments and thereby produces a plurality of fragment/substrate constructs. The transposase preferably produces a plurality of fragment/substrate constructs each comprising a Y adaptor at one end and a hairpin loop adaptor at the other end. The overhangs can be removed from the constructs by selectively removing the at least one nucleotide to produce a plurality of double stranded constructs comprising single stranded gaps. The single stranded gaps in the constructs can be repaired to produce a plurality of modified double stranded polynucleotides.

One strand of the double stranded portion preferably comprises the sequence shown in SEQ ID NO: 26 and the other strand of the double stranded portion preferably comprises a sequence which is complementary to the sequence shown in SEQ ID NO: 26 and which is modified to include at least one nucleotide that is not present in the target polynucleotide. This "other strand" further comprises the overhang. In a more preferred embodiment, one strand of the double stranded portion comprises the sequence shown in SEQ ID NO: 26 and the other strand of the double stranded portion comprises the sequence shown in SEQ ID NO: 27 (see below). In SEQ ID NO: 27, the dA in the dC and dA dinucleotide at the 3' end had been replaced with dU. This double stranded portion (shown below) may be used when the target polynucleotide comprises deoxyadenosine (dA), thymidine (dT), deoxyguanosine (dG) and deoxycytidine (dC), but not deoxyuridine (dU).

```
                                                    (SEQ 26)
5'-GTTTTCGCATTTATCGTGAAACGCTTTCGCGTTTTTCGTGCGCCGC
TTCA-3'

(SEQ 27)
3'-CAAAAGCGTAAATAGCACTTTGCGAAAGCGCAAAAAGCACGCGGCG
AAGU-5'
```

In a most preferred embodiment, one strand of the substrate comprises the sequence shown in SEQ ID NO: 26 and the other strand of the substrate comprises the sequence shown in SEQ ID NO: 28 (see below). This substrate (shown below) may be used when the target polynucleotide comprises deoxyadenosine (dA), thymidine (dT), deoxyguanosine (dG) and deoxycytidine (dC), but not deoxyuridine (dU).

```
                                                    (SEQ 26)
5'-GTTTTCGCATTTATCGTGAAACGCTTTCGCGTTTTTCGTGCGCCGCT
TCA-3'
                                                    (SEQ 28)
3'-CAAAAGCGTAAATAGCACTTTGCGAAAGCGCAAAAAGCACGCGGCGA
AGUCTAG-5'
```

In all of the embodiments above, the proportion of one type of substrate may be any proportion, such as at least about 5%, at least about 10%, at least about 20%, at least about 30%, at least about 40%, at least about 50%, at least about 60%, at least about 70%, at least about 80%, at least about 90% or at least about 95%. The remaining proportion of substrates in the population is typically the other type of substrate. For instance, the population may comprise about 40% of the substrates comprising a hairpin loop and about 60% of the Y substrates. The proportion of both types of substrate is preferably about 50%.

Methods for ligating the overhangs to the fragments, selectively removing the nucleotide(s) which comprise(s) a nucleoside that is not present in the target polynucleotide from the ligated constructs and repairing the single stranded gaps in the double stranded constructs are disclosed in International Application No. PCT/GB2014/052505 (published as WO 2015/022544).

Products of the Invention

The invention also provides a target double stranded polynucleotide modified using a method of the invention. The modified polynucleotide comprises a Y adaptor attached at one end of the polynucleotide and a hairpin loop adaptor attached at the other end, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane, and thereby providing a modified target double stranded polynucleotide.

The invention also provides a plurality of polynucleotides modified using the MuA-based methods of the invention. These modified polynucleotides preferably comprise a Y adaptor attached at one end and a hairpin loop adaptor attached at the other end, wherein the Y adaptor comprises one or more first anchor for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane, and thereby providing a modified target double stranded polynucleotide. Some of the polynucleotides may have Y adaptors as defined above at both ends or hairpin loop adaptors as defined above at both ends.

The invention also provides a pair of adaptors for modifying a target double stranded polynucleotide for characterisation using a transmembrane pore in a membrane, wherein one adaptor is a Y adaptor comprising one or more first anchors for coupling the polynucleotide to the membrane, wherein the other adaptor is a hairpin loop adaptor comprising one or more second anchors for coupling the polynucleotide to the membrane and wherein the strength of coupling of the hairpin loop adaptors to the membrane is greater than the strength of coupling of the Y adaptor to the membrane.

The invention also provides population of adaptors for modifying a target polynucleotide for characterisation using a transmembrane pore in a membrane, wherein a proportion of the adaptors are Y adaptors comprising one or more first anchors for coupling the polynucleotide to the membrane, wherein a proportion of the adaptors are hairpin loop adaptors comprising one or more second anchors for coupling the polynucleotide to the membrane and wherein the strength of coupling of the hairpin loop adaptor to the membrane is greater than the strength of coupling of the Y adaptor to the membrane.

Each adaptor in the pair or population of the invention preferably comprises a double stranded MuA substrate. The substrates may be any of those described above. The substrates preferably comprise a double stranded portion as defined above. The double stranded portion preferably comprises SEQ ID NOs: 26 and 27 as discussed above. The double stranded portion more preferably comprises SEQ ID NOs: 26 and 28 as discussed above.

The proportion values given above in connection with the method of the invention are equally applicable to the populations of the invention.

Any of the embodiments discussed above with reference to the methods of the invention are equally applicable to the polynucleotides, pairs and populations of the invention.

The population or plurality may be isolated, substantially isolated, purified or substantially purified. A population or plurality is isolated or purified if it is completely free of any other components, such as the target polynucleotide, lipids or pores. A population or plurality is substantially isolated if it is mixed with carriers or diluents which will not interfere with its intended use. For instance, a population or plurality is substantially isolated or substantially purified if it is present in a form that comprises less than 10%, less than 5%, less than 2% or less than 1% of other components, such as lipids or pores.

Kits

The present invention also provides a kit for modifying a target polynucleotide comprising (a) a pair of adaptors of the invention or a population of adaptors of the invention and (b) a MuA transposase. Each adaptor in the pair or population preferably comprises a double stranded MuA substrate.

Any of the embodiments discussed above with reference to the methods and products of the invention equally apply to the kits.

The kit may further comprise the components of a membrane, such as the components of an amphiphilic layer or a triblock copolymer membrane. The kit may further comprise a transmembrane pore or the components of a transmembrane pore. The kit may further comprise a polynucleotide binding protein. Suitable membranes, pores and polynucleotide binding proteins are discussed above.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention.

EXAMPLE 1

Figure 1:
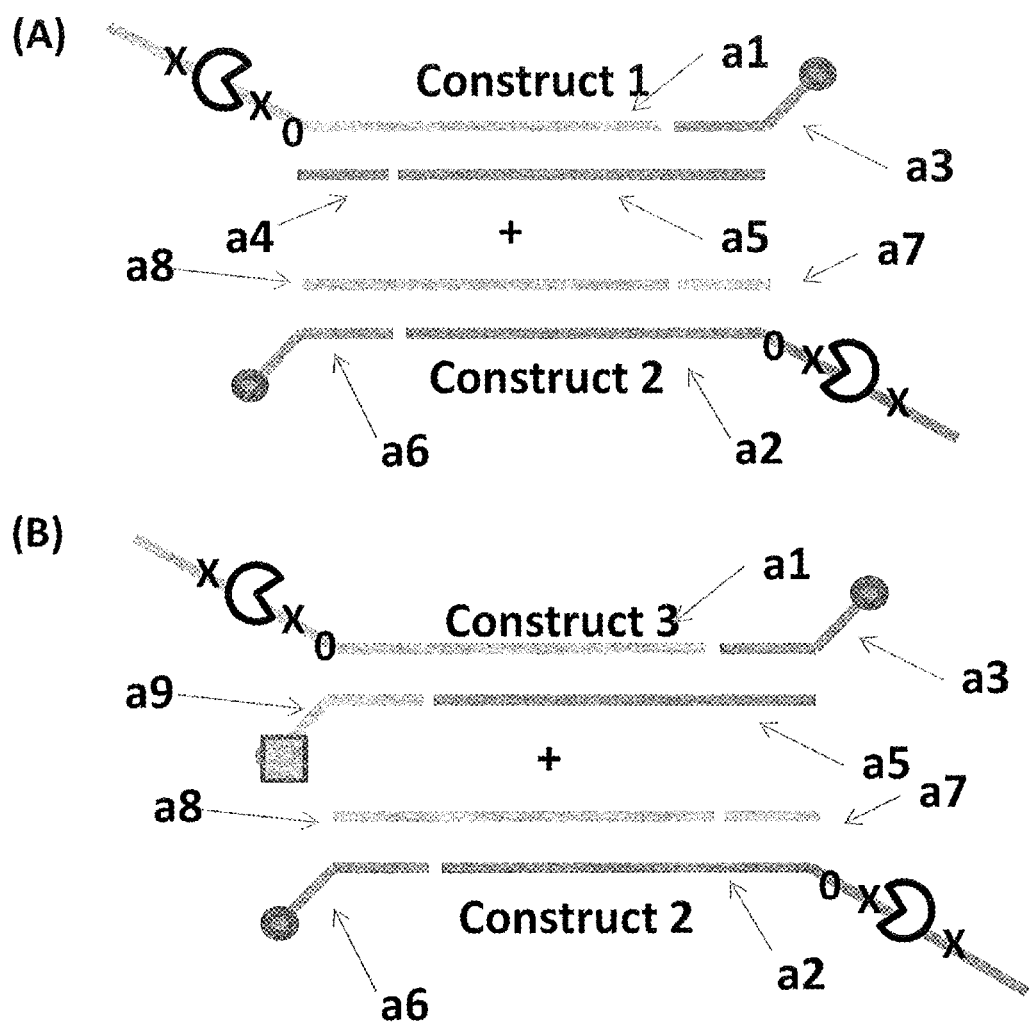
FIG. 1 shows in sections (A) and (B) cartoon representations of the DNA constructs used in Example 2—four iSpC3 spacers are shown as a cross and four 5-nitroindoles as a black 0, the cholesterol coupling agent as a grey oval and the palmitate coupling agent as a grey square; labels al-10 are described in full in Example 1.
Figure 2:
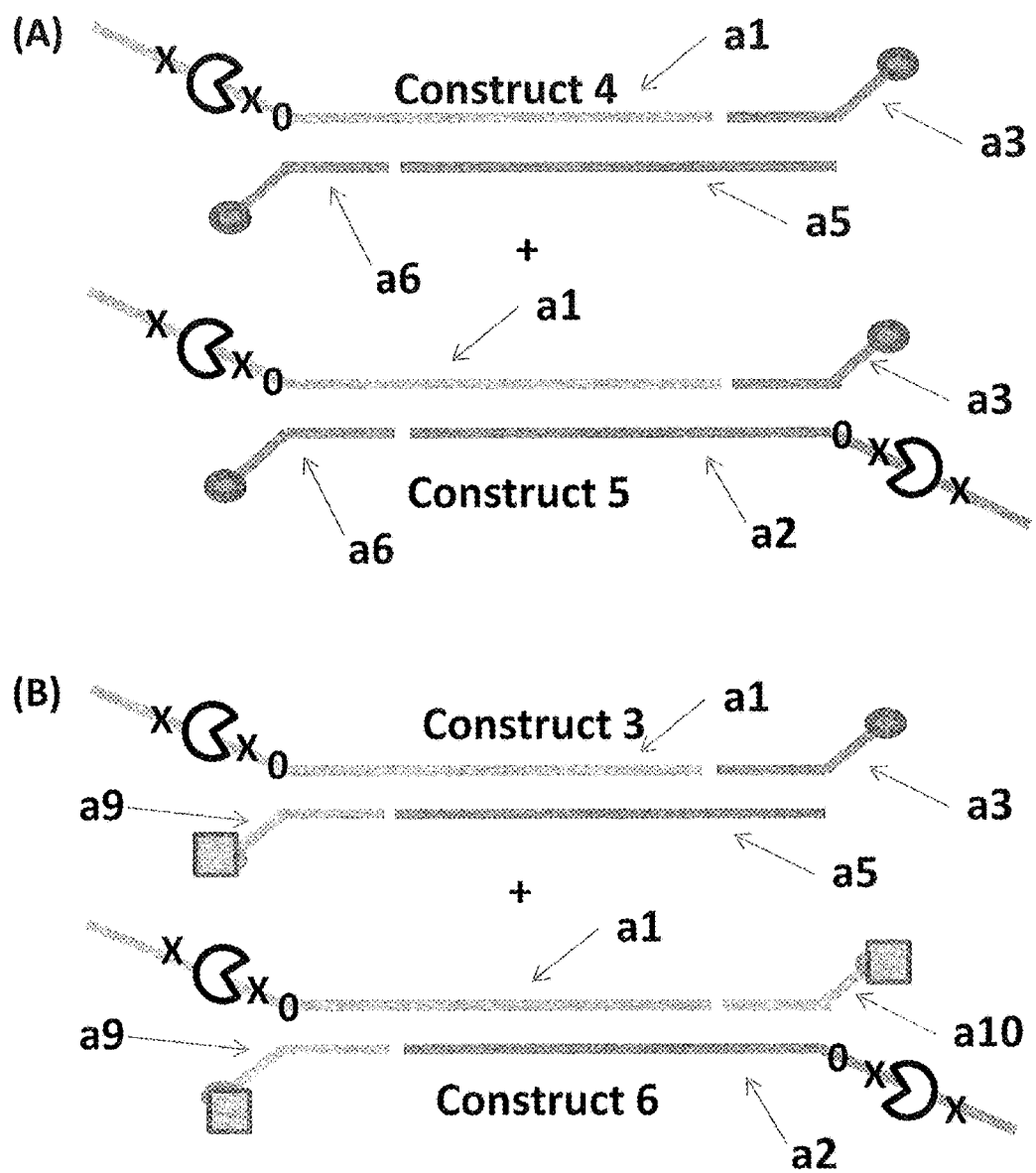
FIG. 2 shows in sections (A) and (B) cartoon representations of the DNA constructs used in Example 3—four iSpC3 spacers are shown as a cross and four 5-nitroindoles as a black 0, the cholesterol coupling agent as a grey oval and the palmitate anchor as a grey square; labels al-9 are described in full in Example 1.

This example describes the sample preparation procedure for the DNA constructs 1-6 shown in FIGS. 1 and 2 and used in Examples 2 and 3.

Materials and Methods

The strands used in this study are from a region of the lambda genome, between 45,042 bp and 48,487 bp. Analytes were made by the polymerase PCR method to include hybridisation sites at defined ends of each of the template and template complement strands as desired. PCR was carried out from lambda genomic DNA.

This template (SEQ ID NO: 29 hybridised to 30) was made using KAPA HiFi 2× Master mix, lambda DNA (NEB) and primers SEQ ID NO: 31 and SEQ ID NO: 32. Reactions were cycled 20 times and product of the correct size was purified by Gel Filtration on Sephacryl S1000 column and concentrated to 0.25 mg/ml using Millipore Ultracel 15 50 kDa concentrators.

DNA constructs (1, 2, 3, 4, 5 and 6) for electrophysiology experiments were all made according to the same reaction mix; 2× LongAmp Taq master mix, 300 nM of primers 1 and 2 or 3 and 4 (strand labelled a1 in FIGS. 1 and 2 was produced using primer 1=SEQ ID NO: 33 attached at its 3' end to four iSpC3 spacers which are attached at the opposite end to the 5' end of SEQ ID NO: 34 which is attached at its 3' end to four iSpC3 spacers which are attached to four 5-nitroindoles which are attached at the opposite end to the 5' end of SEQ ID NO: 36 and primer 2=SEQ ID NO: 37 attached at the 3' end to four 5-nitroindoles which are attached at the opposite end to the 5' end of SEQ ID NO: 38, strand labelled a2 in FIGS. 1 and 2 was produced using primer 3=SEQ ID NO: 33 attached at its 3' end to four iSpC3 spacers which are attached at the opposite end to the 5' end of SEQ ID NO: 37 which is attached at its 3' end to four iSpC3 spacers which are attached to four 5-nitroindoles which are attached at the opposite end to the 5' end of SEQ ID NO: 38 and primer 4=SEQ ID NO: 34 attached at the 3' end to four 5-nitroindoles which are attached at the opposite end to the 5' end of SEQ ID NO: 36) and 1.2 ng ul$^{-1}$ DNA template (SEQ ID NO: 29 hybridised to 30). DNA constructs were all amplified according to the same cycling program; 94° C. for 2 mins, [94° C. for 15 secs, 58° C. for 30 secs, 65° C. for 2 mins]$_{12}$ and 65° C. for 5 mins. DNA constructs were all purified from a 0.8% agarose gel according to manufacturer's instructions (Qiagen Gel Extraction kit) and then SPRI purified (Agencourt AMPure beads) according to manufacturer's instructions.

Finally, the DNA strands produced were hybridised to complementary strands of DNA, some of which contained anchors e.g. cholesterol or palmitate. The complementary strands SEQ ID NO: 39 and 40 (with and without attached anchors) were annealed at a five-fold excess at room temperature for ten minutes in 25 mM potassium phosphate buffer, 151 mM potassium chloride, pH 8.0.

DNA construct 1 was made up of four different strands hybridised together as shown in FIG. 1(A)—a1=SEQ ID NO: 33 attached at its 3' end to four iSpC3 spacers which are attached at the opposite end to the 5' end of SEQ ID NO: 34; SEQ ID NO: 34 is attached at the 3' end to four iSpC3 spacers which are attached at the opposite end to four 5-nitroindoles which are attached to the 5' end of SEQ ID NO: 35, a3=SEQ ID NO: 40 which is attached at its 3' end to six iSp18 spacers which are attached at the opposite end to two thymines which are attached at the opposite end to a 3' cholesterol TEG, a4=SEQ ID NO: 39 and a5=complementary sequence to a3 and part of a1.

DNA construct 2 was made up of four different strands hybridised together as shown in FIG. 1(A) and (B)—a2=SEQ ID NO: 33 attached at its 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 41, a6=SEQ ID NO: 39 which is attached at its 3' end to six iSp18 spacers which are attached at the opposite end to two thymines which are attached at the opposite end to a 3' cholesterol TEG, a7=SEQ ID NO: 40 and a8=complementary sequence to a6 and part of a2.

DNA construct 3 was made up of four different strands hybridised together as shown in FIG. 1(B) and 2(B)—a2=SEQ ID NO: 33 attached at its 3' end to four iSpC3 spacers which are attached at the opposite end to the 5' end of SEQ ID NO: 34; SEQ ID NO: 34 is attached at the 3' end to four iSpC3 spacers which are attached at the opposite end to four 5-nitroindoles which are attached to the 5' end of SEQ ID NO: 35, a3=SEQ ID NO: 40 which is attached at its 3' end to six iSp18 spacers which are attached at the opposite end to two thymines which are attached at the opposite end to a 3' cholesterol TEG, a9=SEQ ID NO: 39 which is attached at its 3' end to six iSp18 spacers which are attached at the opposite end to two thymines which are attached at the opposite end to a 3' palmitate and a5=complementary sequence to a3 and part of a1.

DNA construct 4 was made up of four different strands hybridised together as shown in FIG. 2(A)—a1=SEQ ID NO: 33 attached at its 3' end to four iSpC3 spacers which are attached at the opposite end to the 5' end of SEQ ID NO: 34; SEQ ID NO: 34 is attached at the 3' end to four iSpC3 spacers which are attached at the opposite end to four 5-nitroindoles which are attached to the 5' end of SEQ ID NO: 35, a3=SEQ ID NO: 40 which is attached at its 3' end to six iSp18 spacers which are attached at the opposite end to two thymines which are attached at the opposite end to a 3' cholesterol TEG, a6=SEQ ID NO: 39 which is attached at its 3' end to six iSp18 spacers which are attached at the opposite end to two thymines which are attached at the opposite end to a 3' cholesterol TEG and a5=complementary sequence to a3 and part of a1.

DNA construct 5 was made up of four different strands hybridised together as shown in FIG. 2(A)—a1=SEQ ID NO: 33 attached at its 3' end to four iSpC3 spacers which are attached at the opposite end to the 5' end of SEQ ID NO: 34; SEQ ID NO: 34 is attached at the 3' end to four iSpC3 spacers which are attached at the opposite end to four 5-nitroindoles which are attached to the 5' end of SEQ ID NO: 35, a3=SEQ ID NO: 40 which is attached at its 3' end to six iSp18 spacers which are attached at the opposite end to two thymines which are attached at the opposite end to a 3' cholesterol TEG, a2=SEQ ID NO: 33 attached at its 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 41 and a6=SEQ ID NO: 39 which is attached at its 3' end to six iSp18 spacers which are attached at the opposite end to two thymines which are attached at the opposite end to a 3' cholesterol TEG.

DNA construct 6 was made up of four different strands hybridised together as shown in FIG. 2(B)—a1=SEQ ID NO: 33 attached at its 3' end to four iSpC3 spacers which are attached at the opposite end to the 5' end of SEQ ID NO: 34; SEQ ID NO: 34 is attached at the 3' end to four iSpC3 spacers which are attached at the opposite end to four 5-nitroindoles which are attached to the 5' end of SEQ ID NO: 35, a10=SEQ ID NO: 40 which is attached at its 3' end to six iSp18 spacers which are attached at the opposite end to two thymines which are attached at the opposite end to a 3' palmitate, a2=SEQ ID NO: 33 attached at its 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 41 and a9=SEQ ID NO: 39 which is attached at its 3' end to six iSp18 spacers which are attached at the opposite end to two thymines which are attached at the opposite end to a 3' cholesterol TEG.

EXAMPLE 2

This example compares the use of a single anchor to couple constructs to a membrane to that of two anchors of differing strengths again used to couple constructs to a membrane. Two anchors were employed in order to bias, the helicase-controlled DNA movements detected by the nanopore system, towards the construct which was doubly coupled to the membrane.

Materials and Methods

Prior to setting up the experiment, the DNA constructs either 1 and 2 or 2 and 3 (stock concentration 20 nM, final concentration added to nanopore system 0.1 nM) were separately pre-incubated at room temperature for five minutes with T4 Dda-E94C/A360C (stock concentration 250 nM, final concentration added to nanopore system 1 nM, SEQ ID NO: 24 with mutations E94C/A360C) in buffer (151 mM KCl, 25 mM phosphate, 2 mM EDTA, pH8.0). After five minutes, TMAD (500 µM) was added to the pre-mix and the mixture incubated for a further 5 minutes. Finally, MgCl2 (10 mM final concentration), ATP (2.5 mM final concentration) and buffer (150 mM potassium ferrocyanide (II), 150 mM potassium ferricyanide and 25 mM potassium phosphate pH 8.0) were added to the pre-mix.

Electrical measurements were acquired from single MspA nanopores (MspA-B2C) inserted in block co-polymer in buffer (25 mM potassium phosphate, 150 mM potassium ferrocyanide (II), 150 mM potassium ferricyanide (III), pH 8.0). After achieving a single pore inserted in the block co-polymer, then buffer (2 mL, 25 mM potassium phosphate pH 8.0, 150 mM potassium ferrocyanide (II) and 150 mM potassium ferricyanide (III)) was flowed through the system to remove any excess MspA nanopores. The enzyme (T4 Dda-E94C/A360C, 1 nM final concentration), DNA construct either 1 and 2 or 2 and 3 (0.1 nM final concentration), fuel (MgCl2 10 mM final concentration, ATP 2.5 mM final concentration) pre-mix (150 µL total) was then added to the single nanopore experimental system and the experiment run at a holding potential of 120 mV for 2 hours and helicase-controlled DNA movement monitored.

Results and Discussion

Figure 3:
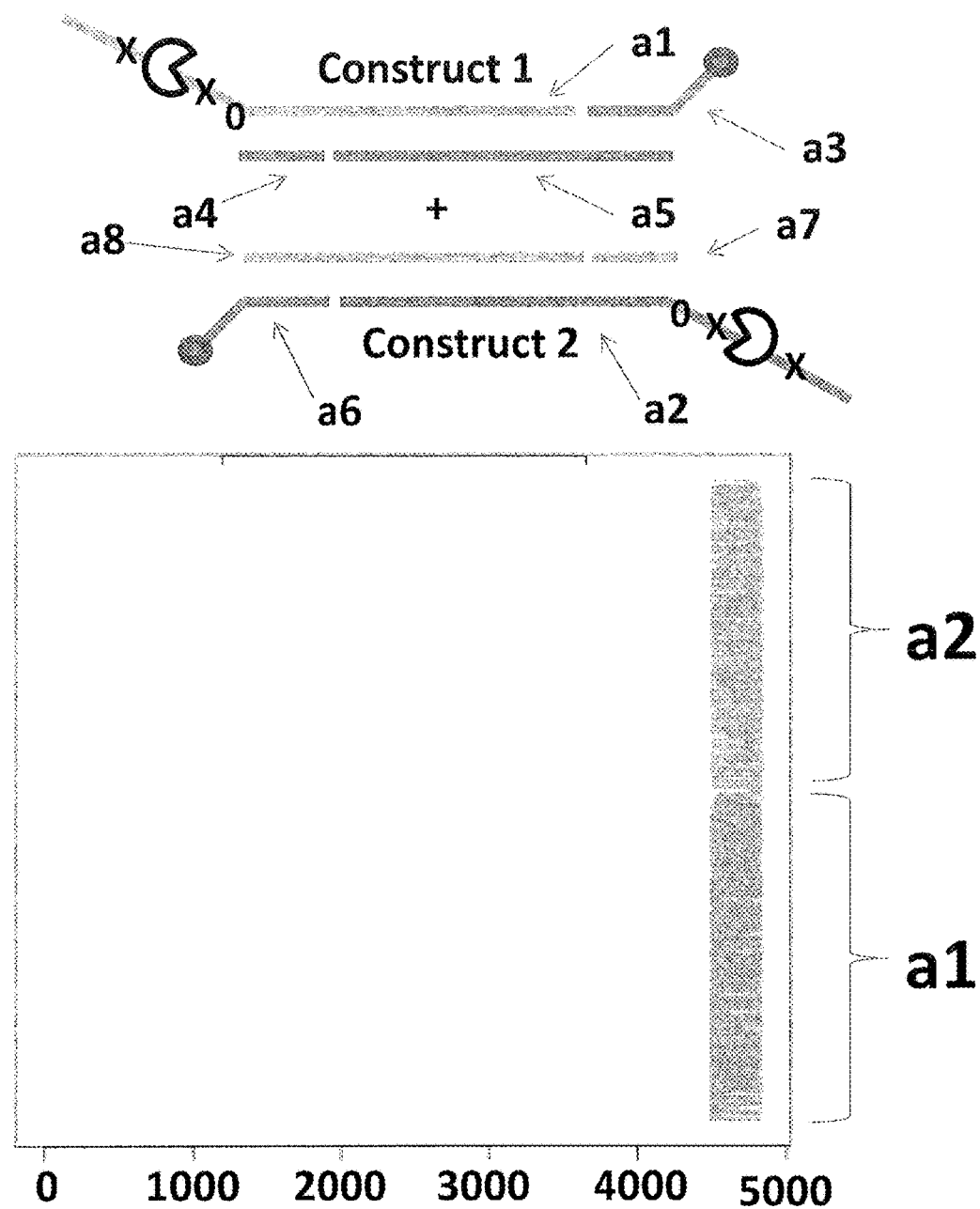
FIG. 3 shows the proportion of helicase-controlled DNA movements detected for construct 1 where strand a2 translocated through the nanopore and construct 2 where strand a2 translocated through the nanopore. The x-axis shows the position along the lambda DNA sequence to which that the helicase-controlled DNA movements mapped (they were all concentrated in the same region as strands a1 and a2 corresponded to the template and template complement of the region of lambda between 45,042 bp and 48,487 bp). The Y-axis shows the proportion of strand a1 (construct 1) helicase-controlled DNA movements (labelled a1) to strand a2 (construct 2) helicase controlled DNA movements (labelled a2). This was observed to be approximately 50:50 when a single cholesterol was used to couple the constructs to the membrane. This control showed that if the same coupling agent was used to couple different constructs to the membrane, the number of helicase controlled DNA movements would have been approximately equal for each construct e.g. no bias was observed.

For the control experiment, helicase-controlled DNA movement of constructs 1 and 2 was monitored. The cartoon at the top of FIG. 3 shows where the helicase can bind to constructs 1 and 2. Helicase controlled DNA movements corresponding to each construct were identified and the proportion of movements corresponding to strand a1 (construct 1) and strand a2 (construct 2) were compared (see the bottom half of FIG. 3). As each construct was coupled to the membrane using the same anchor (a cholesterol anchor) then, of the helicase-controlled DNA movements observed, approximately 50% corresponded to strand a1 and 50% to strand a2. This illustrated that by using the same single anchor, there was no bias towards helicase-controlled translocation movements for one construct over the other.

Figure 4:
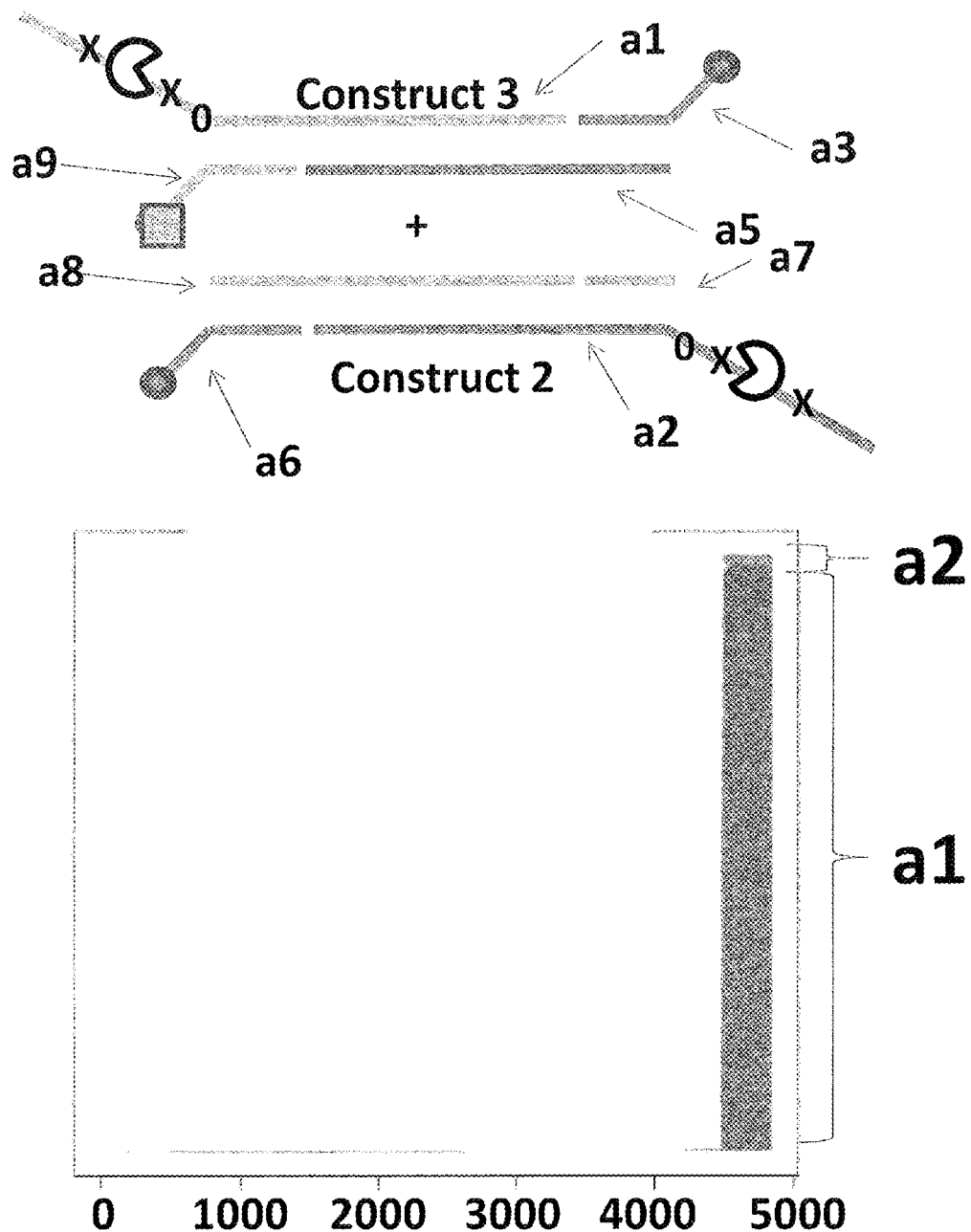
FIG. 4 shows the proportion of helicase-controlled DNA movements detected for construct 2 where strand a2 translocated through the nanopore and construct 3 where strand a1 translocated through the nanopore. The x-axis shows the position along the lambda DNA sequence to which that the helicase-controlled DNA movements mapped (they were all concentrated in the same region as strands a1 and a2 corresponded to the template and template complement of the region of lambda between 45,042 bp and 48,487 bp). The Y-axis shows the proportion of strand a2 (construct 2) helicase-controlled DNA movements (labelled a2) to strand a1 (construct 3) helicase controlled DNA movements (labelled a1). This was observed to be approximately 5:95 when a single cholesterol was used to couple construct 2 to the membrane in comparison to when a cholesterol and a palmitate were used to couple construct 3 to the membrane. This experiment showed that when two coupling agents were used to couple a construct to the membrane (where one was a stronger coupling agent than the other e.g. cholesterol was stronger than palmitate) in comparison to a single coupling agent (cholesterol) the number of helicase-controlled DNA movements was strongly biased towards the doubly coupled construct over the singly coupled construct.

The experiment also compared the use of a single anchor (cholesterol) to couple construct 2 to the membrane, to the use of two different anchors (of differing strength—cholesterol and palmitate) to couple construct 3 to the membrane. The cartoon at the top of FIG. 4 shows where the helicase can bind to strand a1 (constructs 3) and strand a2 (construct 2). Helicase controlled DNA movements corresponding to each construct were identified and the proportion of movements corresponding to a1 and a2 (construct 3 and 2 respectively) were compared (see the bottom half of FIG. 4). In this case more than 95% of the helicase-controlled DNA movements detected corresponded to strand a1 (construct 3), which was coupled to the membrane using a cholesterol and a palmitate. Less than 5% of the helicase-controlled DNA movements corresponded to strand a2 (construct 2). This experiment illustrated that by using two different anchors it was possible to strongly bias the helicase-controlled DNA movements detected by the nanopore system towards the doubly coupled construct over the singly coupled construct.

EXAMPLE 3

This example compares the use of two anchors of equal strength (double cholesterol constructs 4 and 5 or double palmitate construct 6) to two anchors of differing strengths (palmitate and cholesterol construct 3).

Materials and Methods

DNA constructs 4 and 5 or 3 and 6 were pre-incubated with T4 Dda-E94C/A360C helicase as described in Example 2 above.

Electrical measurements were acquired from single MspA nanopores (MspA-B2C) inserted in block co-polymer in buffer as described in Example 2 and helicase-controlled DNA movements for constructs 4 and 5 or 3 and 6 were monitored.

Results and Discussion

Figure 5:
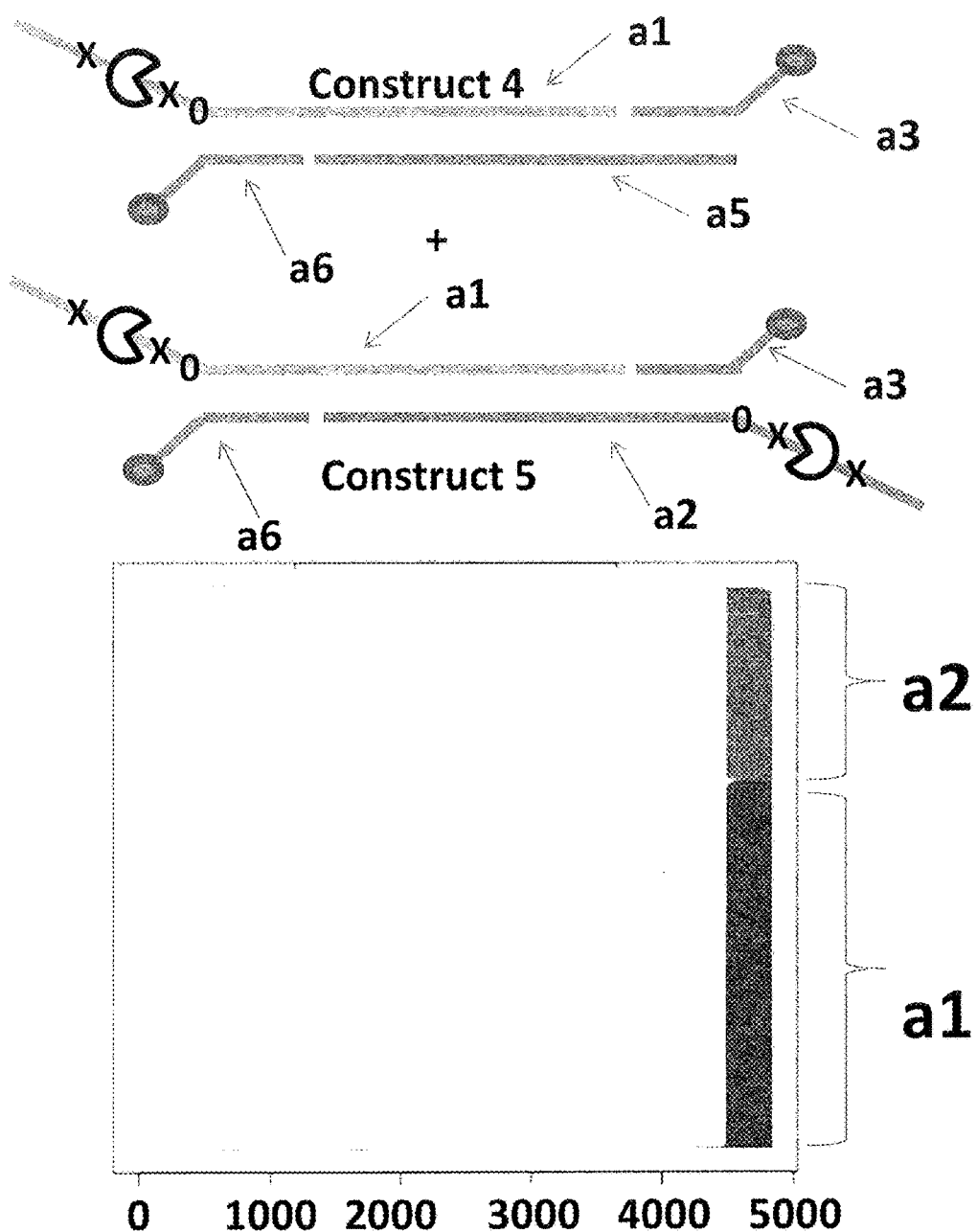
FIG. 5 shows the proportion of helicase-controlled DNA movements detected for construct 4 where strand a2 translocated through the nanopore and construct 5 where strand a1 or a2 translocated through the nanopore. The x-axis shows the position along the lambda DNA sequence to which that the helicase-controlled DNA movements mapped (they were all concentrated in the same region as strands a1 and a2 corresponded to the template and template complement of the region of lambda between 45,042 bp and 48,487 bp). The Y-axis shows the proportion of strand a1 (construct 4 or 5) helicase-controlled DNA movements (labelled a1) to strand a2 (construct 5 only) helicase controlled DNA movements (labelled a2). This was observed to be approximately 33:66 (a2:a1 helicase controlled DNA movements) when two cholesterols were used to couple both constructs to the membrane. The 2:1 bias towards a1 helicase controlled DNA movements was predicted because a2 movements would only be detected if construct 4 was captured by the nanopore, whereas a1 movements would be detected from construct 4 and 5, therefore, twice as many a1 movements were expected.

For the control experiment, helicase-controlled DNA movement of constructs 4 and 5 was monitored. The cartoon at the top of FIG. 5 shows where the helicase can bind to constructs 4 (only on a1) and 5 (on a1 and a2). Strand a1 of construct 4 was capable of being captured by the nanopore, whereas, strand a1 or strand a2 of construct 5 were capable of being captured by the nanopore. Helicase controlled DNA movements corresponding to each construct were identified and the proportion of movements corresponding to strand a1 (construct 4 and 5) and strand a2 (construct 5 only) were compared (see the bottom half of FIG. 5). As each construct was coupled to the membrane using the same anchor (two cholesterol anchors) then of the helicase-controlled DNA movements observed, approximately 66% corresponded to strand a1 (construct 4 and 5) and 33% to strand a2 (construct 5 only). The 2:1 bias towards the detection of a1 helicase controlled DNA movements was expected because a2 movements would only be detected if construct 4 was captured by the nanopore, whereas a1 movements would be detected from capture of both construct 4 and 5, therefore, twice as many a1 movements were expected (as equivalent concentrations of constructs 4 and 5 were added to the nanopore experimental system).

Figure 6:
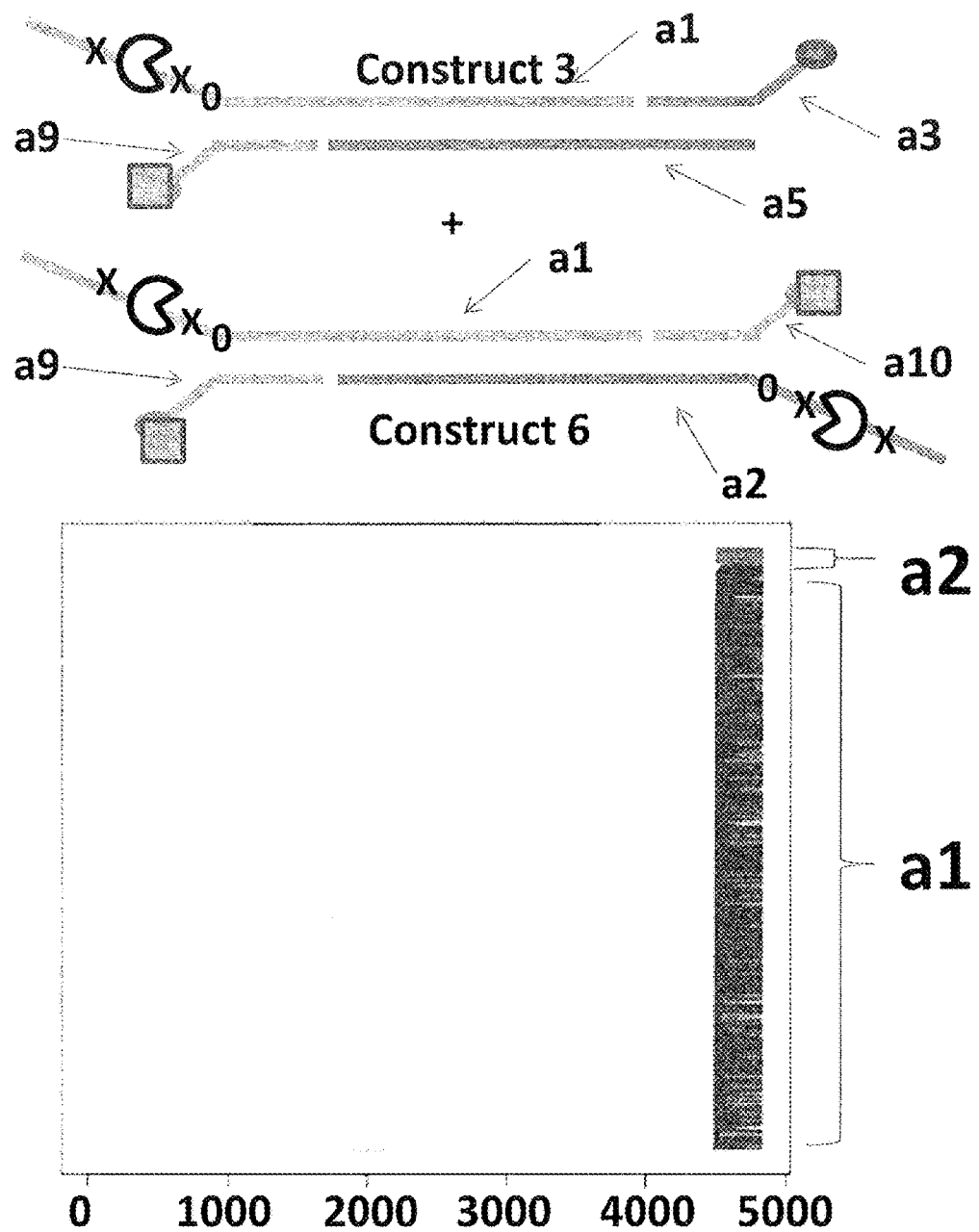
FIG. 6 shows the proportion of helicase-controlled DNA movements detected for construct 3 where strand a2 translocated through the nanopore and construct 6 where strand a1 or a2 translocated through the nanopore. The x-axis shows the position along the lambda DNA sequence to which that the helicase-controlled DNA movements mapped (they were all concentrated in the same region as strands a 1 and a2 corresponded to the template and template complement of the region of lambda between 45,042 bp and 48,487 bp). The Y-axis shows the proportion of strand a1 (construct 3 or 6) helicase-controlled DNA movements (labelled a1) to strand a2 (construct 6 only) helicase controlled DNA movements (labelled a2). This was observed to be approximately 5:95 (a2:a1 helicase controlled DNA movements) when the combination of a cholesterol and a palmitate were used to couple construct 3 to the membrane and two palmitates were used to couple construct 6 to the membrane. The bias towards a1 helicase controlled DNA movements in comparison to the control experiment shown in FIG. 5 illustrated that by using the combination of two different coupling agents of differing strength it was possible to select for this construct over the construct which contained two coupling agents of similar strength.

The experiment also compared the use of two coupling agents of differing strengths (cholesterol and palmitate) to couple construct 3 to the membrane, to the use of two identical coupling agents (both palmitate) to couple construct 6 to the membrane. The cartoon at the top of FIG. 6 shows where the helicase can bind to strand a1 (constructs 3 and 6) and strand a2 (construct 6 only). Strand a1 of construct 3 was capable of being captured by the nanopore, whereas strand a1 or strand a2 of construct 6 were capable of being captured by the nanopore. Helicase controlled DNA movements corresponding to each construct were identified and the proportion of movements corresponding to a1 (construct 2 and 3) and a2 (construct 2 only) were compared (see the bottom half of FIG. 6). In this case more than 95% of the helicase-controlled DNA movements detected corresponded to strand a2 (construct 3 and 6), which were coupled to the membrane using either a cholesterol and a palmitate or two palmitates. Less than 5% of the helicase-controlled DNA movements corresponded to strand a2 (construct 6 only). This experiment illustrated that by using two different coupling agents it was possible to strongly bias the helicase-controlled DNA movements detected by the nanopore system towards the construct coupled by coupling agents of differing strength rather than the construct coupled by two identical coupling agents of equal strength. This also shows that by using the combination of a stronger and weaker anchor on a construct that can only be captured by the nanopore at one end it was possible to bias towards this construct over a construct that has two weaker anchors on a construct that can be captured by the nanopore at either end.

EXAMPLE 4

This example shows how the relative strengths of a number of coupling agents can be compared. This would allow selection of appropriate strength coupling agents for coupling of a construct to a membrane.
Materials and Methods
DNA constructs 1, 2 and 7(a-c) were produced using the method described in Example 1. Constructs 1 and 2 are described in detail above and constructs 7(a-c) are described below.

Figure 7:
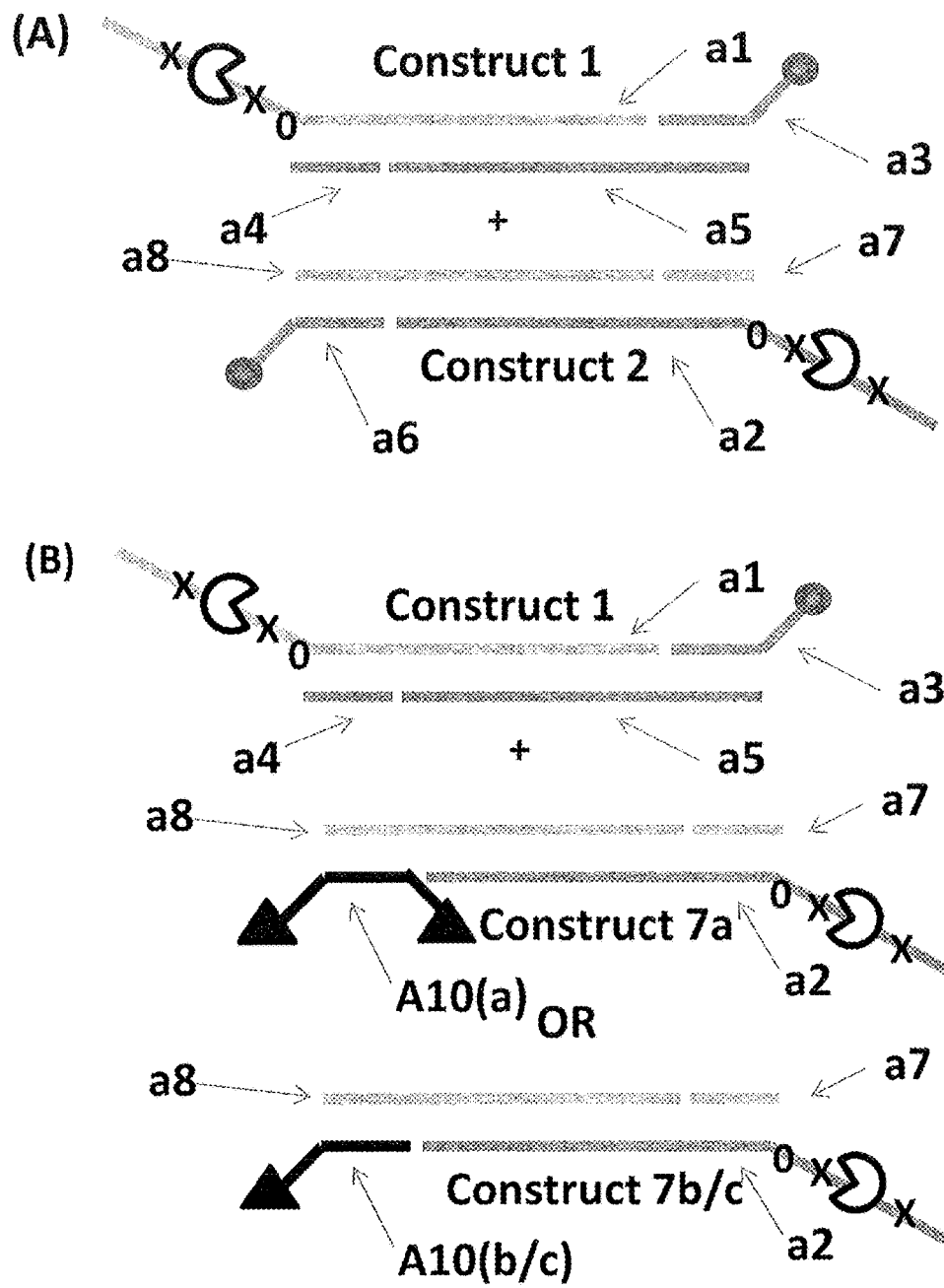
FIG. 7 shows in sections (A) and (B) cartoon representations of the DNA constructs used in Example 4—four iSpC3 spacers are shown as a cross and four 5-nitroindoles as a black 0, the cholesterol coupling agent as a grey oval and the alternative coupling agents investigated in this example as a black triangle; labels a1-10(a-c) are described in full in Example 1 and 4.

DNA construct 7a was made up of four different strands hybridised together as shown in FIG. 7(B)—a2=SEQ ID NO: 33 attached at its 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 41, a10(a)=SEQ ID NO: 42 which has six iSp18 spacers attached to its 5' end which are attached at the opposite end to two thymines and a 5' cholesterol TEG; SEQ ID NO: 42 has a further six iSp18 spacers attached to its 3' end which are attached at the opposite end to two thymines and a 3' cholesterol TEG, a7=SEQ ID NO: 40 and a8=complementary sequence to A10a and part of a2.

DNA construct 7b was made up of four different strands hybridised together as shown in FIG. 7(B)—a2=SEQ ID NO: 33 attached at its 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 41, a10(b)=SEQ ID NO: 39 which is attached at its 3' end to six iSp18 spacers which are attached at the opposite end to two thymines which are attached at the opposite end to a 3' tocopherol, a7=SEQ ID NO: 40 and a8=complementary sequence to A10b and part of a2.

DNA construct 7c was made up of four different strands hybridised together as shown in FIG. 7(B)—a2=SEQ ID NO: 33 attached at its 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 41, a10(c)=SEQ ID NO: 39 which is attached at its 3' end to six iSp18 spacers which are attached at the opposite end to two thymines which are attached at the opposite end to a 3' palmitate, a7=SEQ ID NO: 40 and a8=complementary sequence to A10c and part of a2.

DNA constructs 1, 2 and 7(a-c) were pre-incubated with T4 Dda -E94C/A360C helicase as described in Example 2 above.

Figure 8:
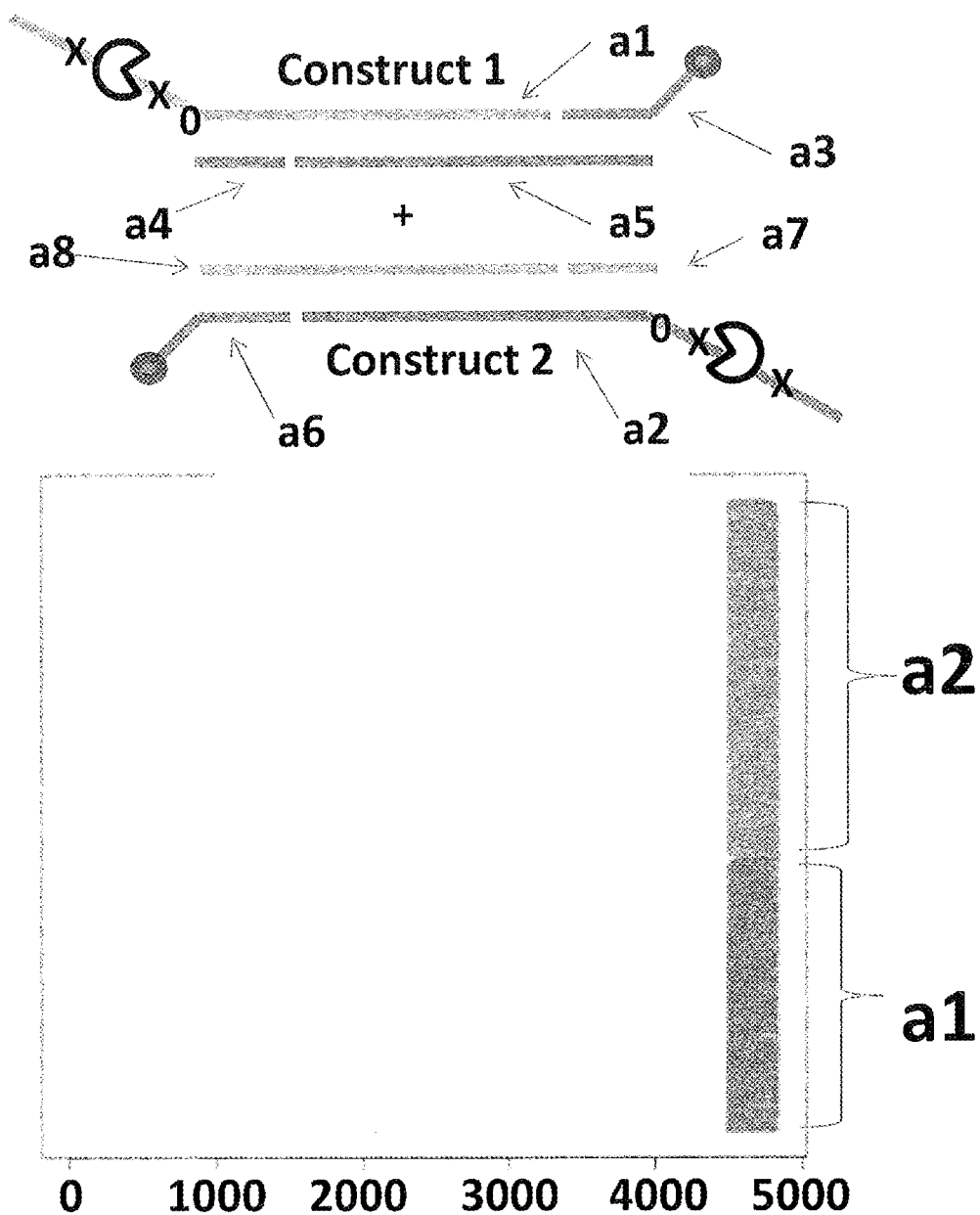
FIG. 8 shows the proportion of helicase-controlled DNA movements detected for construct 1 (coupled to the membrane using a single cholesterol) where strand a 1 translocated through the nanopore and construct 2 (also coupled to the membrane using a single cholesterol) where strand a2 translocated through the nanopore. The x-axis shows the position along the lambda DNA sequence to which that the helicase-controlled DNA movements mapped (they were all concentrated in the same region as strands a1 and a2 corresponded to the template and template complement of the region of lambda between 45,042 bp and 48,487 bp). The Y-axis shows the proportion of strand a1 (construct 1) helicase-controlled DNA movements (labelled a1) to strand a2 (construct 2) helicase controlled DNA movements (labelled a2). This was observed to be approximately 50:50 when a single cholesterol was used to couple each construct to the membrane. This control showed that if the same coupling agent was used to couple different constructs to the membrane, the number of helicase controlled DNA movements would have been approximately equal for each construct e.g. no bias was observed.

Electrical measurements were acquired from single MspA nanopores (MspA −B2C) inserted in block co-polymer in buffer as described in Example 2 and helicase-controlled DNA movements for constructs 1, 2 and 7(a-c) were monitored.
Results and Discussion
For the control experiment, helicase-controlled DNA movement of constructs 1 and 2 was monitored. The cartoon at the top of FIG. 8 shows where the helicase can bind to constructs 1 and 2. Helicase controlled DNA movements corresponding to each construct were identified and the proportion of movements corresponding to strand a1 (construct 1) and strand a2 (construct 2) were compared (see the bottom half of FIG. 8). As each construct was coupled to the membrane using the same coupling agent cholesterol) then, of the helicase-controlled DNA movements observed, approximately 50% corresponded to strand a1 and 50% to strand a2 This illustrated that by using the same single coupling agent, there was no bias towards helicase-controlled translocation movements for one construct over the other.

Figure 9:
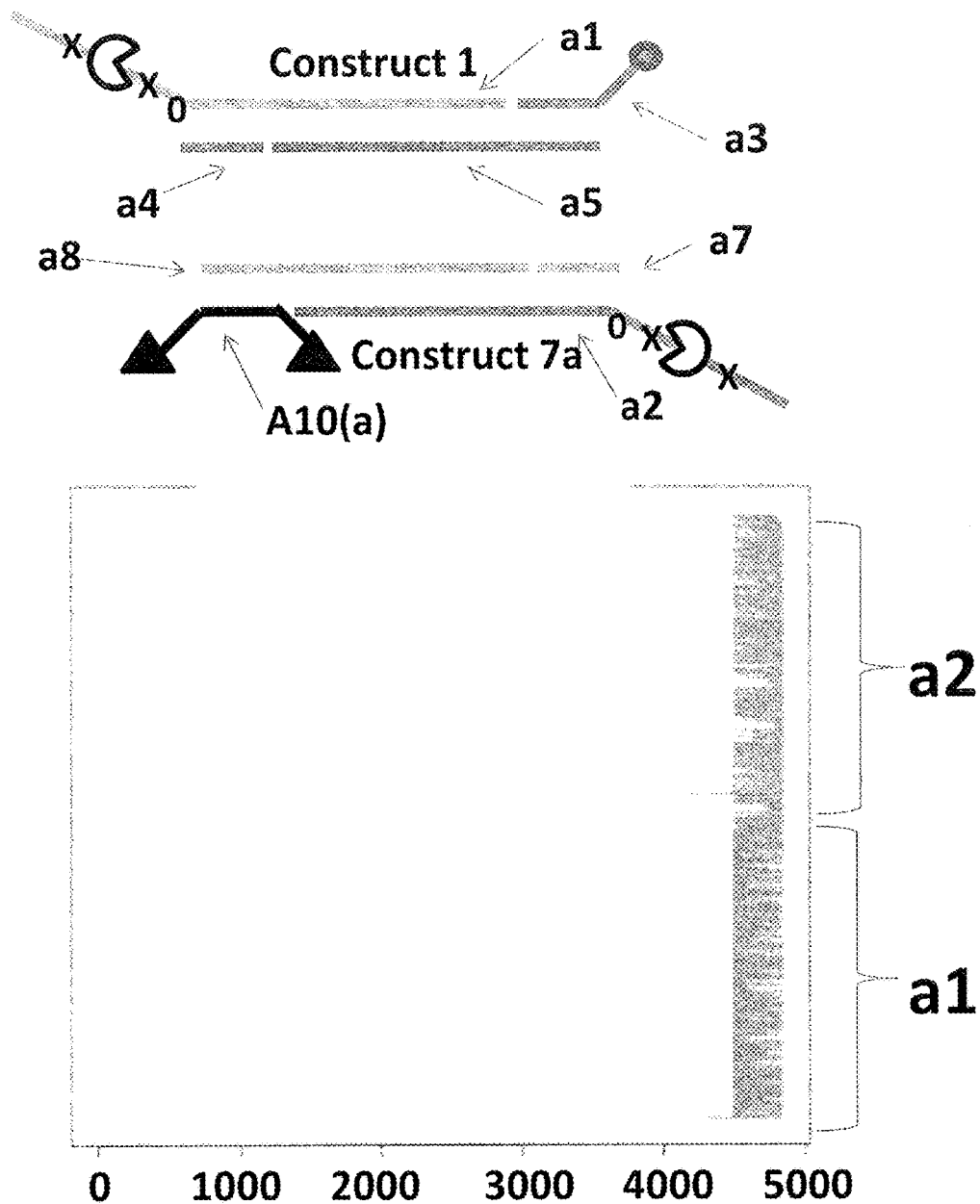
FIG. 9 shows the proportion of helicase-controlled DNA movements detected for construct 1 (coupled to the membrane using a single cholesterol) where strand a 1 translocated through the nanopore and construct 7 a (coupled to the membrane using a fragment of DNA which had two cholesterol TEG's attached, each shown as a black triangle) where strand a 2 translocated through the nanopore. The x-axis shows the position along the lambda DNA sequence to which that the helicase-controlled DNA movements mapped (they were all concentrated in the same region as strands a 1 and a 2 corresponded to the template and template complement of the region of lambda between 45,042 bp and 48,487 bp). The Y-axis shows the proportion of strand a1 (construct 1) helicase-controlled DNA movements (labelled a1) to strand a2 (construct 7a) helicase controlled DNA movements (labelled a2). This was observed to be approximately 50:50 when a single cholesterol was used to couple construct 1 to the membrane in comparison to when two cholesterols were used to couple construct 7a to the membrane. This experiment showed that when two cholesterols attached to the same fragment of DNA were used to couple construct 7a to the membrane, in comparison to a single cholesterol, the number of helicase-controlled DNA movements detected showed no bias towards either construct. Therefore, the strength of coupling observed for two cholesterols in the same DNA fragment was similar to a single cholesterol.
Figure 10:
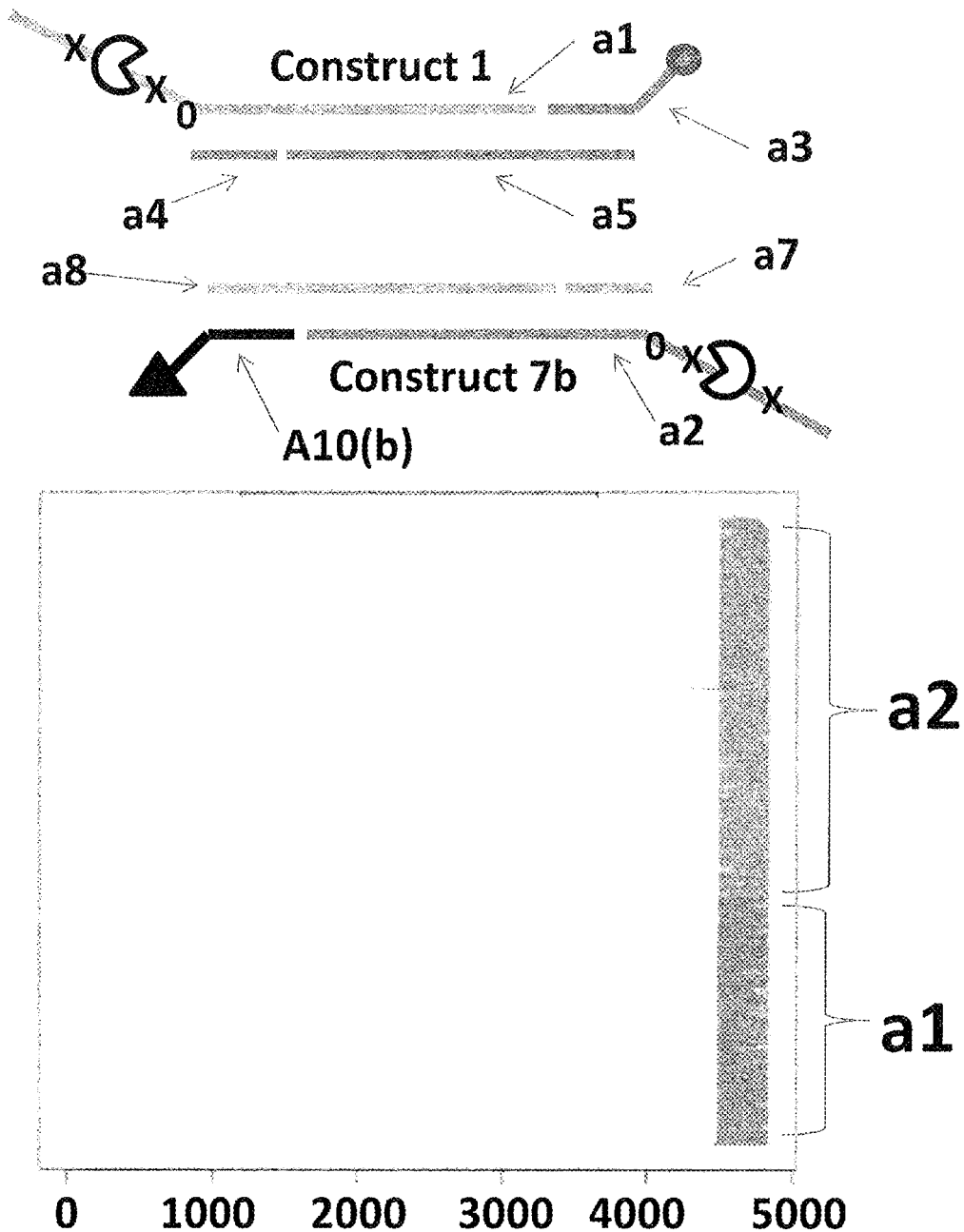
FIG. 10 shows the proportion of helicase-controlled DNA movements detected for construct 1 (coupled to the membrane using a single cholesterol) where strand a1 translocated through the nanopore and construct 7b (coupled to the membrane using a tocopherol, shown as a black triangle) where strand a2 translocated through the nanopore. The x-axis shows the position along the lambda DNA sequence to which that the helicase-controlled DNA movements mapped (they were all concentrated in the same region as strands a1 and a2 corresponded to the template and template complement of the region of lambda between 45,042 bp and 48,487 bp). The Y-axis shows the proportion of strand a1

The experiment also compared the use of a variety of different coupling agents to couple constructs 7(a-c) to the membrane to that of cholesterol which was used to couple construct 1 to the membrane. The cartoons at the top of FIGS. 9-11 show where the helicase could bind to strand a1 (constructs 1) and strand a2 (construct 7(a-c)). Helicase controlled DNA movements corresponding to each construct were identified and the proportion of movements corresponding to a1 and a2 (construct 1 and 7(a-c) respectively) were compared (see the bottom half of FIGS. 9-11). The use of two cholesterols in the same strand of DNA (A10a) was observed to have an equivalent coupling strength to that of the single cholesterol (see FIG. 9). Whereas, the use of a tocopherol was observed to be a stronger coupling agent than cholesterol (see FIG. 10), as a greater number of DNA controlled helicase movements were observed for the construct anchored by tocopherol than cholesterol. Furthermore, palmitate was observed to be a weaker coupling agent than cholesterol because fewer helicase controlled DNA movements were observed for the construct anchored by palmitate than cholesterol (see FIG. 11). Therefore, by comparing the coupling strengths of various coupling agents using this method it would be possible to select two different strength coupling agents and bias the system towards selection of a desired construct (see example 6 for further details).

EXAMPLE 5

This example describes the sample preparation procedure for the DNA constructs 8 and 9 shown in FIG. 12 and used in Examples 6.
Materials and Methods
Lambda DNA (1 μg, SEQ ID NO: 43) was restriction enzyme digested for 1 hour at 37° C. in 1× NEBuffer 4, with 5 U of SnaBI and 20 U of BamHI-HF. Following digestion, the DNA was purified using 1.5× Agencourt AMPure beads, according to the manufacturer's protocol. The sample was then eluted in 50 uL of nuclease free water. The DNA was then end-repaired using NEB's NEBNext End-repair system, following the manufacturer's protocol. The sample was again purified using 1.5× Agencourt AMPure beads and the DNA eluted in 42 uL of nuclease free water. Following the end-repair step, the purified DNA was dA-tailed using NEB's NEBNext dA-tailing system, according to the manufacturer's protocol. The DNA was again purified using 1.5× Agencourt AMPure beads, eluting in 20 uL of nuclease free water. The DNA was quantified at A260 nm and adapters ligated at a 25-fold excess per 5' end, using NEB's NEBNext quick ligase module following the manufacturer's protocol. Construct 8 was produced by ligating the following adapters to the fragments of DNA (labelled as a12 in FIG. 12) (adapter 1 (labelled a11 in FIG. 12)=25 iSpC3 spacers attached at to the 5' to SEQ ID NO: 44 which is attached at its 3' end to four iSp18 spacers which are attached at the opposite end to the 5' end of SEQ ID NO: 45 which is attached at the 3' end to the sequence AACCT (which are joined together by phosphorothioate bonds) where the final T in the sequence is attached to a further non-modified T; adapter 2 (labelled as a14 in FIG. 12)=has a phosphate group at the 5' end of sequence GGTT (which are joined together by phosphorothioate bonds), this sequence is attached at its 3' end to the 5' end of SEQ ID NO: 46 which is attached at the 3' end to six iSp18 spacers which are attached at the opposite end to two thymines which are attached at the opposite end to a 3' cholesterol TEG and adapter 3 (labelled as a13 in FIG. 12)=has a phosphate group at the 5' end of SEQ ID NO: 47 and which has an internal cholesterol TEG attached to the 3' end of SEQ ID NO: 47, the internal cholesterol is also attached to the 5' end of SEQ ID NO: 48 which is attached at its 3' end to a G with a phosphorothioate bond and a non-modified T). Construct 9 was produced by ligating the following adapters to the fragments of DNA (labelled as a12 in FIG. 12) (adapter 1 (labelled as a11 in FIG. 12)=25 iSpC3 spacers attached at to the 5' to SEQ ID NO: 44 which is attached at its 3' end to four iSp18 spacers which are attached at the opposite end to the 5' end of SEQ ID NO: 45 which is attached at the 3' end to the sequence AACCT (which are joined together by phosphorothioate bonds) where the final T in the sequence is attached to a further non-modified T; adapter 4 (labelled as a15 in FIG. 12)=has a phosphate group at the 5' end of sequence GGTT (which are joined together by phosphorothioate bonds), this sequence is attached at its 3' end to the 5' end of SEQ ID NO: 46 which is attached at the 3' end to six iSp18 spacers which are attached at the opposite end to two thymines which are attached at the opposite end to a 3' palmitate and adapter 3 (labelled as a13 in FIG. 12)=has a phosphate group at the 5' end of SEQ ID NO: 47 and which has an internal cholesterol TEG attached to the 3' end of SEQ ID NO: 47, the internal cholesterol is also attached to the 5' end of SEQ ID NO: 48 which is attached at its 3' end to a G with a phosphorothioate bond and a non-modified T). Following digestion, the ligated DNA was purified using 0.4× Agencourt AMPure beads, eluting in 16 uL of nuclease free water. The DNA was quantified at A260 nm and 4 uL of 757.5 mM KCl, 125 mM potassium phosphate buffer (pH 7) and 5 mM EDTA was added.

EXAMPLE 6

This example compares the helicase controlled DNA movements detected for constructs 8 and 9. Construct 8 was coupled to the membrane using two cholesterols (both strong coupling agents). Construct 9 was coupled to the membrane using cholesterol in the hairpin and a palmitate in the Y-adaptor. The constructs both contained lambda DNA which had been fragmented by the process described above.
Materials and Methods
DNA constructs 8 and 9 were each separately pre-incubated with T4 Dda—E94C/A360C/C109A/C136A helicase using a similar procedure to that described in Example 2 above.

Electrical measurements were acquired from single MspA nanopores (MspA-B2C) inserted in block co-polymer in buffer as described in Example 2 and helicase-controlled DNA movements for constructs 8 and 9 were monitored.
Results and Discussion
During the fragmentation and adapter attachment process (described in Example 5) the desired constructs shown in FIG. 12 were produced. However, other constructs were also produced during that process which had either two Y-adapters attached (constructs 11 and 12) or two hairpin adapters attached (construct 10) (see FIGS. 13 and 14). In order for the nanopore to be able to capture DNA, the DNA must have had at least one Y-adapter so that there was a free end to be captured by the pore. Therefore, the DNA constructs with two hairpins attached (construct 10) were not be observed in the nanopore experiments. The constructs which had a Y-adapter on both ends of the lambda DNA fragments could be captured by the nanopore by either end of the DNA (constructs 11 and 12). However, as there was no hairpin attached to the DNA, then only strand x or strand y was translocated through the nanopore. However, if constructs 8 or 9 were captured by the nanopore (via the Y-adapter end) then both strand X and strand Y translocated through the nanopore owing to the hairpin attached at the opposite end. Therefore, it was desired that the constructs which contained a Y adapter and a hairpin were preferentially captured by the nanopore. It was not possible to separate out the various constructs (10, 8 and 11 or 10, 9 and 12) in order to isolate just the desired constructs 8 and 9.

It was investigated as to whether constructs which contained a Y-adapter and a hairpin adapter could be preferentially selected and captured by the nanopore by utilising different combinations of coupling agents. In this example coupling of two cholesterols (construct 8) was compared to coupling of cholesterol and a palmitate (construct 9). Both of the constructs tested exhibited high numbers of helicase controlled DNA movements of either the hairpin/Y-adapter constructs (8 and 9) or the double Y-adapter constructs (11 and 12). When the same coupling agent (cholesterol) was used in both the Y-adapter and the hairpin (construct 8) then 25% of the helicase-controlled DNA movements detected corresponded to construct 8 and 75% to construct 11. Therefore, only a quarter of the movements detected corresponded to the desired construct. When a strong coupling agent (cholesterol in this case) was used in the hairpin and a weaker coupling agent was used in the Y-adapter (palmitate in this case) 46% of the helicase-controlled DNA movements detected corresponded to construct 9 and 56% to construct 12. This is a significant improvement towards selection of the desired construct 9. This improvement in detection of the desired construct was owing to the use of two coupling agents of differing strengths. The double Y-adapter construct 12 was coupled to the membrane using two weaker coupling agents in comparison to the Y-adapter/hairpin construct 9 which was coupled to the membrane using one weak and one strong anchor. As the desired construct employed one anchor which was stronger than those used in the double Y-adapter construct this was preferentially coupled to the membrane and therefore a larger proportion of the helicase-controlled DNA movements detected corresponded to desired construct 9.

EXAMPLE 7

This example compares the coupling efficiency of a number of different DNA constructs 13, 14, 15 and 16 which were coupled to the membrane by a number of means.

Construct 13 was coupled to the membrane using cholesterol in the hairpin region and a palmitate hybridised by a rigid DNA linker in the Y-adaptor region. Construct 14 was coupled to the membrane using cholesterol in the hairpin region and a palmitate hybridised by a flexible DNA linker in the Y-adaptor region. Construct 15 was coupled to the membrane using cholesterol in the hairpin region and a cholesterol hybridised by a rigid DNA linker in the Y-adaptor region. Construct 16 was coupled to the membrane using cholesterol in the hairpin region and a cholesterol hybridised by a flexible DNA linker in the Y-adaptor region.

Materials and Methods

The constructs all contained lambda DNA fragments (labelled in FIGS. 15 and 16 as a12) which had been fragmented by the process described above in Example 5, however, different adapters were then ligated to the DNA constructs. The adapters ligated to form DNA constructs 13-16 (shown in FIGS. 15 and 16) are described in detail below—

Constructs 13, 14, 15 and 16 were produced by ligating the following adapters to the fragments of lambda DNA (labelled as a12 in FIGS. 15 and 16) (adapter 1 (labelled a16 in FIG. 15)=30 iSpC3 spacers attached to the 5' to SEQ ID NO: 51 which is attached at its 3' end to four iSp18 spacers which are attached at the opposite end to the 5' end of SEQ ID NO: 52; adapter 2 (labelled as a17 in FIG. 15)=has a phosphate group at the 5' end of SEQ ID NO: 49, this sequence is attached at its 3' end to four iSpC3 spacer which are attached at the opposite end to the 5' end of SEQ ID NO: 50 which is attached at the 3' end to a Thymine via a phosphothioate bond; and adapter 3 (labelled as a18 in FIG. 15)=has a phosphate group at the 5' end of SEQ ID NO: 53.

After purification of the above constructs as described in Example 5 then either rigid or flexible DNA linkers with either palmitate or cholesterol attached at the 5' end were then hybridised to the constructs under the following conditions—0.2ul of each DNA linker (10 uM) was added to 13 ul of ligated DNA (stock conc. approximately 20-30 nM) and incubated at room temperature for 10 mins.

Construct 13 was hybridised to the adaptor 4 (labelled in FIG. 15 as a20)=SEQ ID NO: 40 is attached at its 5' end to six iSp18 spacers which are attached at the opposite end to two thymines and a 5' cholesterol TEG and adaptor 5 (labelled in FIG. 15 as a19)=SEQ ID NO: 54 which is attached at the 5' end to a palmitate.

Construct 14 was hybridised to the adaptor 4 (labelled in FIG. 15 as a20)=SEQ ID NO: 40 is attached at its 5' end to six iSp18 spacers which are attached at the opposite end to two thymines and a 5' cholesterol TEG and adaptor 6 (labelled in FIG. 15 as a21)=SEQ ID NO: 54 which is attached at its 5' end to six iSp18 spacers which are attached at the opposite end to two thymines and a palmitate.

Construct 15 was hybridised to the adaptor 4 (labelled in FIG. 15 as a20)=SEQ ID NO: 40 is attached at its 5' end to six iSp18 spacers which are attached at the opposite end to two thymines and a 5' cholesterol TEG and adaptor 5 (labelled in FIG. 15 as a22)=SEQ ID NO: 54 which is attached at the 5' end to a cholesterol TEG.

Construct 16 was hybridised to the adaptor 4 (labelled in FIG. 15 as a20)=SEQ ID NO: 40 is attached at its 5' end to six iSp18 spacers which are attached at the opposite end to two thymines and a 5' cholesterol TEG and adaptor 6 (labelled in FIG. 15 as a23)=SEQ ID NO: 54 which is attached at its 5' end to six iSp18 spacers which are attached at the opposite end to two thymines and a cholesterol TEG.

Prior to setting up the experiment, the DNA constructs 13-16 (final concentration added to nanopore system 0.2 nM) were separately pre-incubated at room temperature for five minutes with T4 Dda-E94C/A360C/C109A/C136A (final concentration added to nanopore system 10 nM) in buffer (151 mM KCl, 25 mM phosphate, 5% glycerol, pH7.0). After five minutes, TMAD (500 μM) was added to the pre-mix and the mixture incubated for a further 5 minutes. Finally, MgCl2 (2 mM final concentration), ATP (2.5 mM final concentration) and buffer (500 mM KCl and 25 mM potassium phosphate pH 8.0) were added to the pre-mix.

Electrical measurements were acquired from MspA nanopores (MspA-B2C) inserted in block co-polymer in buffer as described in Example 2 and helicase-controlled DNA movements for constructs 13-16 were monitored.

Results and Discussion

This example compares the coupling efficiency of a number of different DNA constructs 13, 14, 15 and 16 by investigating the number of helicase controlled DNA movements which were observed for each nanopore over the course of an experiment and the percentage of these helicase-controlled movements which corresponded to translocation of both region R1 and R2 when compared to all other helicase-controlled DNA movements detected.

For all four of the different constructs tested, helicase controlled DNA movements were observed. In this experiment we have compared the strengths of two different types of anchor—palmitate and cholesterol. It was also possible to compare how the flexibility of two different types of double-stranded polynucleotide linkers affected the strength of the coupling. In all four constructs, the coupling agent in the hairpin a20 (flexible cholesterol tether) remained constant and the coupling agent used in the Y-adapter was varied between palmitate/cholesterol and flexible/rigid linkers. The constructs used in this experiment were made by the same fragmentation and adapter attachment process described in Example 5. This produced the desired constructs shown in FIGS. 15 and 16 as well as constructs analogous to those shown in FIGS. 13 and 14 which had either two Y-adapters attached or two hairpin adapters attached. As described in more detail in example 6 above, in order for the nanopore to be able to capture DNA, the DNA must have had at least one Y-adapter so that there was a free end which was able to be captured by the pore. Therefore, DNA constructs with two hairpins attached were not observed in the nanopore experiments. The constructs which had a Y-adapter on both ends of the DNA fragments were captured by the nanopore by either end of the DNA. However, as there was no hairpin attached to the DNA, then only R1 or R2 would have been translocated through the nanopore. However, if the desired constructs β-16 were captured by the nanopore (via the Y-adapter end) then regions R1 and R2 would have both translocated through the nanopore. Therefore, it was desired that the constructs which contained a Y adapter and a hairpin were preferentially captured by the nanopore.

The data shown in FIG. 17 illustrates the % of the total number of helicase controlled DNA movements detected which corresponded to the translocation of both R1 and R2 regions through the nanopore (which are produced from the desired constructs which contained a Y-adapter and a hairpin adapter). Other helicase-controlled DNA movements which were observed corresponded to translocation of constructs which had two Y-adapters attached to the fragments of lambda DNA rather than a Y-adapter and a hairpin adapter. The highest percentage of helicase-controlled DNA movements of both R1 and R2 regions through the nanopore (and corresponded to the desired construct) was observed when a palmitate was used with either a rigid or flexible linker (constructs 13 and 14). The cholesterol with the rigid tether had a higher percentage of helicase-controlled DNA movements which corresponded to translocation of both R1 and R2 through the nanopore than the cholesterol with the flexible tether.

It is also clear from the data shown in FIG. 18 that for both palmitate (constructs 13 and 14) and cholesterol (constructs 15 and 16) the rigid arrangement was a slightly weaker coupling arrangement than the flexible arrangement as constructs 13 and 15 resulted in fewer helicase-controlled DNA movements detected per nanopore. The weakest coupling arrangement tested was in construct 15 where a rigid linker attached to a palmitate was used.

The preferred coupling system would be one which resulted in a high number of helicase-controlled DNA movements per nanopore which also had the highest percentage of helicase-controlled DNA movements which corresponded to translocation of regions R1 and R2. The experiments showed that the highest % of helicase controlled DNA movements for R1 and R2 resulted in the lowest number of helicase-controlled DNA movements per nanopore and vice versa. Therefore, the preferred construct design for optimum overall throughput of the desired helicase controlled DNA movements was construct 15 which had a high number of helicase-controlled DNA movements per nanopore with a percentage of helicase-controlled DNA movements which corresponded to translocation of regions R1 and R2 of just under 50%.

The invention claimed is:

1. A method of characterising a target double stranded polynucleotide using a transmembrane pore in a membrane, comprising:
   a) providing the target double stranded polynucleotide with a Y adaptor at one end and a hairpin loop adaptor at the other end, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane;
   b) contacting the polynucleotide provided in step a) with the transmembrane pore such that at least one strand of the polynucleotide moves through the pore; and
   c) taking one or more measurements as the at least one strand of the polynucleotide moves with respect to the pore wherein the measurements are indicative of one or more characteristics of the at least one strand of the polynucleotide and thereby characterising the double stranded target polynucleotide.

2. A method according to claim 1, wherein (a) the hairpin loop adaptor comprises more anchors than the Y adaptor, (b) the strength of coupling of one or more second anchors to the membrane is greater than the strength of coupling of the one or more first anchors to the membrane (c) the strength of coupling of the one or more second anchors to the hairpin loop adaptor is greater than the strength of coupling of the one or more first anchors to the Y adaptor, (d) the one or more first anchors and one or more second anchors couple their respective adaptors to the membrane via hybridisation and the strength of hybridisation is greater in the one or more second anchors than in the one or more first anchors, (e) the one or more first anchors comprise one or more rigid linkers and the one or more second anchors comprise one or more flexible linkers or (f) any combination of (a) to (e).

3. A method according to claim 2, wherein (i) the one or more second anchors couple to the membrane using cholesterol and the one or more first anchors couple to the membrane using palmitate, (ii) the one or more second anchors couple to the membrane using a mono-acyl species and the one or more first anchors couple to the membrane using a diacyl species, (iii) the one or more first anchors comprise one or more polynucleotide linkers and the one or more second anchors comprise one or more flexible linkers comprising one or more one or more spacer 9 (iSp9) groups or one or more spacer 18 (iSp18), (iv) a combination of (i) and (iii) or (v) a combination of (ii) and (iii).

4. A method according to claim 1, wherein step a) comprises modifying the target double stranded polynucleotide so that it comprises the Y adaptor at one end and the hairpin loop adaptor at the other end.

5. A method according to claim 1, wherein step b) comprises contacting the polynucleotide provided in step a) with a transmembrane pore such that both strands of the polynucleotide move through the pore and step c) comprises taking one or more measurements as the both strands of the polynucleotide move with respect to the pore wherein the measurements are indicative of one or more characteristics of the strands of the polynucleotide and thereby characterising the target polynucleotide.

6. A method according to claim 1, wherein the one or more characteristics are selected from (i) the length of the polynucleotide, (ii) the identity of the polynucleotide, (iii) the sequence of the polynucleotide, (iv) the secondary structure of the polynucleotide and (v) whether or not the polynucleotide is modified.

7. A method according to claim 1, wherein the one or more characteristics of the polynucleotide are measured by electrical measurement and/or optical measurement.

8. A method according to claim 7, wherein the electrical measurement is a current measurement, an impedance measurement, a tunnelling measurement or a field effect transistor (FET) measurement.

9. A method according to claim 1, wherein step b) further comprises contacting the polynucleotide provided in step a) with a polynucleotide binding protein such that the protein controls the movement of the at least one strand of the polynucleotide through the pore.

10. A method according to claim 9, wherein the method comprises:
   b) contacting the polynucleotide provided in step a) with a transmembrane pore and a polynucleotide binding protein such that at least one strand of the polynucleotide moves through the pore and the protein controls the movement of the at least one strand of the polynucleotide through the pore; and
   c) measuring the current passing through the pore as the at least one strand of the polynucleotide moves with respect to the pore wherein the current is indicative of one or more characteristics of the at least one strand of the polynucleotide and thereby characterising the double stranded target polynucleotide.

11. A method according to claim 9, wherein the polynucleotide binding protein is derived from a helicase.

12. A method according to claim 1, wherein the membrane is an amphiphilic layer or a solid state layer.

13. A method according to claim 1, wherein the transmembrane pore is a transmembrane protein pore.

14. A method according to claim 13, wherein the transmembrane protein pore is derived from *Mycobacterium smegmatis porin* (Msp), α-hemolysin (α-HL) or lysenin.

15. A method for modifying a target double stranded polynucleotide for characterisation using a transmembrane pore in a membrane, comprising
   (a) ligating a Y adaptor to one end of the polynucleotide and ligating a hairpin loop adaptor to the other end of the polynucleotide; and
   (b) attaching to the Y adaptor one or more first anchors for coupling the polynucleotide to the membrane, attaching to the hairpin loop adaptor one or more second anchors for coupling the polynucleotide to the membrane and thereby providing a modified target double stranded polynucleotide;
   wherein the strength of coupling of the hairpin loop adaptor to the membrane is greater than the strength of coupling of the Y adaptor to the membrane.

16. A method according to claim 15, wherein (a) the hairpin loop adaptor comprises more anchors than the Y adaptor, (b) the strength of coupling of one or more second anchors to the membrane is greater than the strength of coupling of the one or more first anchors to the membrane, (c) the strength of coupling of the one or more second anchors to the hairpin loop adaptor is greater than the strength of coupling of the one or more first anchors to the Y adaptor, (d) the one or more first anchors and one or more second anchors couple their respective adaptors to the membrane via hybridisation and the strength of hybridisation is greater in the one or more second anchors than in the one or more first anchors, (e) the one or more first anchors comprise one or more rigid linkers and the one or more second anchors comprise one or more flexible linkers, or (f) any combination of (a) to (e).

17. A method according to claim 10, wherein the polynucleotide binding protein is derived from a helicase.

* * * * *